United States Patent
Macdonald et al.

(10) Patent No.: US 10,881,085 B2
(45) Date of Patent: Jan. 5, 2021

(54) NON-HUMAN ANIMALS THAT MAKE SINGLE DOMAIN BINDING PROTEINS

(71) Applicant: Regeneron Pharmaceuticals, Inc., Tarrytown, NY (US)

(72) Inventors: Lynn Macdonald, Harrison, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/664,765

(22) Filed: Mar. 20, 2015

(65) Prior Publication Data

US 2015/0289489 A1    Oct. 15, 2015

Related U.S. Application Data

(60) Provisional application No. 61/968,986, filed on Mar. 21, 2014, provisional application No. 61/968,905, filed on Mar. 21, 2014.

(51) Int. Cl.
*A01K 67/027* (2006.01)
*C12N 15/85* (2006.01)
*C07K 16/00* (2006.01)

(52) U.S. Cl.
CPC ...... *A01K 67/0278* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/01* (2013.01); *C07K 16/00* (2013.01); *C07K 2317/515* (2013.01); *C07K 2317/52* (2013.01); *C07K 2317/569* (2013.01); *C07K 2317/64* (2013.01)

(58) Field of Classification Search
USPC .................................... 800/8, 18, 3
See application file for complete search history.

(56) References Cited

U.S. PATENT DOCUMENTS

| | | | |
|---|---|---|---|
| 4,977,081 A | 12/1990 | Raybould et al. | |
| 5,545,806 A | 8/1996 | Lonberg et al. | |
| 5,545,807 A | 8/1996 | Surani et al. | |
| 5,574,205 A | 11/1996 | Kucherlapati et al. | |
| 5,667,988 A | 9/1997 | Barbas et al. | |
| 5,759,808 A | 6/1998 | Casterman | |
| 5,770,429 A | 6/1998 | Lonberg et al. | |
| 5,789,208 A | 8/1998 | Sharon | |
| 5,800,988 A | 9/1998 | Casterman et al. | |
| 5,840,526 A | 11/1998 | Casterman et al. | |
| 5,874,541 A | 2/1999 | Casterman et al. | |
| 5,888,789 A | 3/1999 | Rodriguez | |
| 5,939,598 A | 8/1999 | Kucherlapati et al. | |
| 5,942,435 A | 8/1999 | Wheeler | |
| 6,005,079 A | 12/1999 | Casterman et al. | |
| 6,015,695 A | 1/2000 | Casterman et al. | |
| 6,075,181 A | 6/2000 | Kucherlapati et al. | |
| 6,080,560 A | 6/2000 | Russell et al. | |
| 6,080,910 A | 6/2000 | Schreiber et al. | |
| 6,096,551 A | 8/2000 | Barbas et al. | |
| 6,114,598 A | 9/2000 | Kucherlapati et al. | |
| 6,139,835 A | 10/2000 | Kucherlapati et al. | |
| 6,150,584 A | 11/2000 | Kucherlapati et al. | |

(Continued)

FOREIGN PATENT DOCUMENTS

| | | |
|---|---|---|
| CN | 1203922 A | 1/1999 |
| CN | 1560081 A | 1/2005 |

(Continued)

OTHER PUBLICATIONS

International Search Report & Written Opinion with respect to PCT/US2015/021892, dated Nov. 4, 2015.

(Continued)

*Primary Examiner* — Michael C Wilson
(74) *Attorney, Agent, or Firm* — Rita S. Wu; Margarita Zippin; FisherBroyles, LLP

(57) ABSTRACT

Genetically modified non-human animals and methods and compositions for making and using them are provided, wherein the genetic modification comprises (a) a deletion in an immunoglobulin constant region $C_H 1$ gene (optionally a deletion in a hinge region) of a heavy chain constant region gene sequence, and (b) replacement of one or all endogenous $V_H$, $D_H$ and $J_H$ gene segments with at least one unrearranged light chain variable ($V_L$) gene segment and at least one unrearranged light chain joining ($J_L$) gene segment capable of recombining to form a rearranged light chain variable region ($V_L/J_L$) nucleotide sequence operably linked to the heavy chain constant region gene sequence comprising a deletion in the $C_H 1$ gene and/or insertion of a genetically engineered single rearranged light chain, wherein the mouse is capable of expressing a functional IgM, single domain antigen binding proteins, e.g., $V_L$-single domain binding proteins, and a genetically engineered rearranged light chain.

3 Claims, 21 Drawing Sheets

Specification includes a Sequence Listing.

(56) References Cited

U.S. PATENT DOCUMENTS

| | | |
|---|---|---|
| 6,162,963 A | 12/2000 | Kucherlapati et al. |
| 6,461,818 B1 | 10/2002 | Bradley et al. |
| 6,514,752 B1 | 2/2003 | Kucherlapati et al. |
| 6,551,592 B2 | 4/2003 | Lindhofer et al. |
| 6,586,251 B2 | 7/2003 | Economides et al. |
| 6,596,541 B2 | 7/2003 | Murphy et al. |
| 6,632,976 B1 | 10/2003 | Tomizuka et al. |
| 6,657,103 B1 | 12/2003 | Kucherlapati et al. |
| 6,673,986 B1 | 1/2004 | Kucherlapati et al. |
| 6,713,610 B1 | 3/2004 | Kucherlapati et al. |
| 6,765,087 B1 | 7/2004 | Casterman et al. |
| 6,774,279 B2 | 8/2004 | Dymecki |
| 6,838,254 B1 | 1/2005 | Hamers |
| 6,914,128 B1 | 7/2005 | Salfeld et al. |
| 6,998,514 B2 | 2/2006 | Bruggemann |
| 7,052,873 B2 | 5/2006 | Tsuchiya |
| 7,064,244 B2 | 6/2006 | Jakobovits et al. |
| 7,067,284 B1 | 6/2006 | Barbas et al. |
| 7,084,260 B1 | 8/2006 | Lonberg et al. |
| 7,105,348 B2 | 9/2006 | Murphy et al. |
| 7,119,248 B1 | 10/2006 | Rajewsky et al. |
| 7,129,084 B2 | 10/2006 | Buelow et al. |
| 7,183,076 B2 | 2/2007 | Arathoon et al. |
| 7,241,733 B2 | 7/2007 | Heavner |
| 7,262,028 B2 | 8/2007 | Van Berkel et al. |
| 7,294,754 B2 | 11/2007 | Poueymirou et al. |
| 7,435,871 B2 | 10/2008 | Green et al. |
| 7,501,552 B2 | 3/2009 | Lonberg et al. |
| 7,534,604 B2 | 5/2009 | Fandl et al. |
| 7,541,513 B2 | 6/2009 | Bruggermann |
| 7,582,298 B2 | 9/2009 | Stevens et al. |
| 7,585,668 B2 | 9/2009 | Buelow et al. |
| 7,605,237 B2 | 10/2009 | Stevens et al. |
| 7,642,228 B2 | 1/2010 | Carter et al. |
| 7,704,498 B2 | 4/2010 | Gerritsen et al. |
| 7,722,871 B2 | 5/2010 | Casterman |
| 7,786,047 B2 | 8/2010 | Casterman |
| 7,790,367 B2 | 9/2010 | Casterman |
| 7,794,981 B2 | 9/2010 | Hamers |
| 7,879,985 B2 | 2/2011 | Urso et al. |
| 7,910,798 B2 | 3/2011 | Tanamachi et al. |
| 7,919,257 B2 | 4/2011 | Hoogenboom et al. |
| 7,932,431 B2 | 4/2011 | Bruggemann |
| 8,158,419 B2 | 4/2012 | Lonberg et al. |
| 8,293,500 B2 | 10/2012 | Wiley et al. |
| 8,502,018 B2 | 8/2013 | Murphy et al. |
| 8,568,992 B2 | 10/2013 | Walker et al. |
| 8,586,713 B2 | 11/2013 | Davis et al. |
| 8,592,562 B2 | 11/2013 | Kannan et al. |
| 8,629,317 B2 | 1/2014 | Cogne et al. |
| 8,642,835 B2 * | 2/2014 | MacDonald ....... A01K 67/0278 435/326 |
| 8,697,940 B2 | 4/2014 | Macdonald et al. |
| 8,754,287 B2 | 6/2014 | Macdonald et al. |
| 9,248,182 B2 | 2/2016 | De Kruif et al. |
| 9,315,824 B2 | 4/2016 | Kuroiwa et al. |
| 9,365,655 B2 | 6/2016 | Craig et al. |
| 9,516,868 B2 | 12/2016 | Macdonald et al. |
| 9,686,970 B2 | 6/2017 | Macdonald et al. |
| 10,251,377 B2 | 4/2019 | Clube |
| 2002/0026036 A1 | 2/2002 | Shitara et al. |
| 2002/0088016 A1 | 7/2002 | Bruggemann |
| 2002/0106628 A1 | 8/2002 | Economides et al. |
| 2002/0106629 A1 | 8/2002 | Economides et al. |
| 2003/0017534 A1 | 1/2003 | Buelow et al. |
| 2003/0078385 A1 | 4/2003 | Arathoon et al. |
| 2003/0103970 A1 | 6/2003 | Tsuchiya |
| 2003/0108925 A1 | 6/2003 | Dix et al. |
| 2003/0109021 A1 | 6/2003 | Wu et al. |
| 2003/0118592 A1 | 6/2003 | Ledbetter |
| 2003/0138440 A1 | 7/2003 | Fang et al. |
| 2003/0217373 A1 | 11/2003 | Green et al. |
| 2004/0015880 A1 | 1/2004 | Floyd et al. |
| 2004/0018626 A1 | 1/2004 | Murphy et al. |
| 2004/0052773 A1 | 3/2004 | Bogen et al. |
| 2004/0101920 A1 | 5/2004 | Radziejewski et al. |
| 2004/0137570 A1 | 7/2004 | Grosveld |
| 2004/0142432 A1 | 7/2004 | Grosveld |
| 2004/0146991 A1 | 7/2004 | Tsuji et al. |
| 2005/0059082 A1 | 3/2005 | Breitling et al. |
| 2005/0060763 A1 | 3/2005 | Bruggeman et al. |
| 2005/0153392 A1 | 7/2005 | Buelow et al. |
| 2005/0170398 A1 | 8/2005 | Van Berkel et al. |
| 2005/0229263 A1 | 10/2005 | Buelow |
| 2005/0246782 A1 | 11/2005 | Etches et al. |
| 2006/0015949 A1 | 1/2006 | Lonberg et al. |
| 2006/0015957 A1 | 1/2006 | Lonberg et al. |
| 2006/0015958 A1 | 1/2006 | Kuroiwa et al. |
| 2006/0021074 A1 | 1/2006 | Kellermann et al. |
| 2006/0026696 A1 | 2/2006 | Buelow et al. |
| 2006/0083747 A1 | 4/2006 | Winter |
| 2006/0099207 A1 | 5/2006 | Wu et al. |
| 2006/0106203 A1 | 5/2006 | Winter |
| 2006/0117398 A1 | 6/2006 | Buelow et al. |
| 2006/0153826 A1 | 7/2006 | Arnould et al. |
| 2006/0199204 A1 | 9/2006 | Dix et al. |
| 2006/0257406 A1 | 11/2006 | Winter |
| 2006/0280734 A1 | 12/2006 | Winter |
| 2007/0009957 A1 | 1/2007 | Bowdish et al. |
| 2007/0196363 A1 | 8/2007 | Arathoon et al. |
| 2007/0209083 A1 | 9/2007 | Thiam et al. |
| 2007/0275466 A1 | 11/2007 | Economides et al. |
| 2007/0280945 A1 | 12/2007 | Stevens et al. |
| 2008/0069822 A1 | 3/2008 | Jensen et al. |
| 2008/0196112 A1 | 8/2008 | Romagne |
| 2008/0267982 A1 | 10/2008 | Kiselev et al. |
| 2009/0042254 A1 | 2/2009 | Retallack |
| 2009/0083879 A1 | 3/2009 | Dhugga |
| 2009/0092582 A1 | 4/2009 | Bogin et al. |
| 2009/0093059 A1 | 4/2009 | Baszczynski et al. |
| 2009/0181855 A1 | 7/2009 | Vasquez et al. |
| 2009/0258392 A1 | 10/2009 | Gallo et al. |
| 2009/0271880 A1 | 10/2009 | Grosveld et al. |
| 2009/0285805 A1 | 11/2009 | Grosveld |
| 2009/0307787 A1 | 12/2009 | Grosveld |
| 2010/0069614 A1 | 3/2010 | Houtzager et al. |
| 2010/0122358 A1 | 5/2010 | Bruggemann et al. |
| 2010/0146647 A1 | 6/2010 | Logtenberg et al. |
| 2010/0196367 A1 | 8/2010 | Day |
| 2010/0197897 A1 | 8/2010 | Grosveld |
| 2010/0216974 A1 | 8/2010 | Grosveld |
| 2010/0254988 A1 | 10/2010 | Bossenmaier et al. |
| 2010/0254989 A1 | 10/2010 | Bossenmaier et al. |
| 2010/0286374 A1 | 11/2010 | Kannan et al. |
| 2010/0298542 A1 | 11/2010 | Igawa et al. |
| 2010/0310586 A1 | 12/2010 | Dolcetti et al. |
| 2010/0331527 A1 | 12/2010 | Davis et al. |
| 2011/0004948 A1 | 1/2011 | Grosveld |
| 2011/0004949 A1 | 1/2011 | Grosveld |
| 2011/0123527 A1 | 5/2011 | Shizuya et al. |
| 2011/0138489 A1 | 6/2011 | Tanamachi et al. |
| 2011/0145937 A1 * | 6/2011 | MacDonald ....... A01K 67/0275 800/6 |
| 2011/0195454 A1 * | 8/2011 | McWhirter ........ A01K 67/0278 435/69.6 |
| 2011/0236378 A1 | 9/2011 | Green et al. |
| 2011/0283376 A1 | 11/2011 | Murphy et al. |
| 2011/0314563 A1 | 12/2011 | Craig et al. |
| 2012/0021409 A1 * | 1/2012 | McWhirter ........ A01K 67/0278 435/6.1 |
| 2012/0047585 A1 | 2/2012 | Rohrer et al. |
| 2012/0070861 A1 | 3/2012 | Macdonald et al. |
| 2012/0073004 A1 | 3/2012 | Macdonald et al. |
| 2012/0096572 A1 | 4/2012 | Macdonald et al. |
| 2012/0167237 A1 | 6/2012 | Bradley et al. |
| 2012/0192300 A1 * | 7/2012 | Babb .................. A01K 67/0278 800/18 |
| 2012/0204278 A1 | 8/2012 | Bradley et al. |
| 2012/0222140 A1 | 8/2012 | Kuroiwa et al. |
| 2012/0272344 A1 | 10/2012 | Tanamachi et al. |
| 2012/0322108 A1 | 12/2012 | Macdonald et al. |
| 2013/0045492 A1 * | 2/2013 | Babb .................. A01K 67/0278 435/7.92 |
| 2013/0096020 A1 | 4/2013 | Throsby et al. |

(56) References Cited

U.S. PATENT DOCUMENTS

| | | |
|---|---|---|
| 2013/0096287 A1 | 4/2013 | Macdonald et al. |
| 2013/0145484 A1 | 6/2013 | Logtenberg et al. |
| 2013/0185821 A1* | 7/2013 | Babb .................. A01K 67/0278 800/18 |
| 2013/0198879 A1 | 8/2013 | McWhirter et al. |
| 2013/0198880 A1 | 8/2013 | Babb et al. |
| 2013/0212719 A1 | 8/2013 | Macdonald et al. |
| 2013/0243759 A1 | 9/2013 | Friedrich et al. |
| 2013/0243773 A1 | 9/2013 | Van Berkel et al. |
| 2013/0263292 A1 | 10/2013 | Liang et al. |
| 2013/0263293 A1 | 10/2013 | Bradley et al. |
| 2013/0302836 A1* | 11/2013 | McWhirter ........ A01K 67/0278 435/7.92 |
| 2013/0318643 A1 | 11/2013 | Bradley et al. |
| 2013/0323235 A1 | 12/2013 | Craig et al. |
| 2014/0243504 A1 | 8/2014 | Davis et al. |
| 2014/0283150 A1 | 9/2014 | Bradley et al. |
| 2014/0289876 A1 | 9/2014 | Macdonald et al. |
| 2014/0310828 A1 | 10/2014 | Lee et al. |
| 2014/0322756 A1 | 10/2014 | Arathoon et al. |
| 2015/0059009 A1 | 2/2015 | McWhirter et al. |
| 2015/0133641 A1 | 5/2015 | Germaschewski et al. |
| 2015/0196015 A1 | 7/2015 | Macdonald et al. |
| 2015/0197553 A1 | 7/2015 | Macdonald et al. |
| 2015/0197554 A1 | 7/2015 | Macdonald et al. |
| 2015/0197555 A1 | 7/2015 | Macdonald et al. |
| 2015/0197556 A1 | 7/2015 | Macdonald et al. |
| 2015/0197557 A1 | 7/2015 | Macdonald et al. |
| 2015/0201589 A1 | 7/2015 | Macdonald et al. |
| 2015/0210776 A1 | 7/2015 | Macdonald et al. |
| 2015/0250152 A1 | 9/2015 | Jakobovits et al. |
| 2015/0266976 A1 | 9/2015 | Babb et al. |
| 2015/0313193 A1 | 11/2015 | McWhirter et al. |
| 2016/0219847 A1 | 8/2016 | McWhirter et al. |
| 2016/0238600 A1 | 8/2016 | Hoogenboom et al. |
| 2017/0094955 A1 | 4/2017 | Macdonald et al. |
| 2017/0223939 A1 | 8/2017 | Macdonald et al. |
| 2017/0226231 A1 | 8/2017 | Macdonald et al. |
| 2017/0369593 A1 | 12/2017 | McWhirter et al. |
| 2018/0244804 A1 | 8/2018 | Macdonald et al. |
| 2018/0273641 A1 | 9/2018 | Babb et al. |
| 2019/0021295 A1 | 1/2019 | Babb et al. |
| 2019/0040123 A1 | 2/2019 | McWhirter et al. |
| 2019/0071519 A1 | 3/2019 | McWhirter et al. |
| 2019/0077884 A1 | 3/2019 | McWhirter et al. |
| 2019/0090462 A1 | 3/2019 | Babb et al. |

FOREIGN PATENT DOCUMENTS

| | | |
|---|---|---|
| CN | 101962408 A | 2/2011 |
| EP | 0364096 A2 | 4/1990 |
| EP | 0583980 A1 | 2/1994 |
| EP | 0491057 B1 | 12/1998 |
| EP | 1439234 A1 | 7/2004 |
| EP | 1505148 B1 | 4/2009 |
| EP | 2050764 A1 | 4/2009 |
| EP | 1605058 B1 | 5/2009 |
| EP | 1589107 B1 | 12/2009 |
| EP | 2147594 A1 | 1/2010 |
| EP | 2505654 A1 | 10/2012 |
| EP | 2517556 A2 | 10/2012 |
| EP | 2517557 A2 | 10/2012 |
| EP | 2556747 A2 | 2/2013 |
| EP | 2564695 A1 | 3/2013 |
| WO | 1989/007142 A1 | 8/1989 |
| WO | 1990/004036 A1 | 4/1990 |
| WO | 1991/000906 A1 | 1/1991 |
| WO | 1991/008216 A1 | 6/1991 |
| WO | 1992/003918 A1 | 3/1992 |
| WO | 1994/002602 A1 | 2/1994 |
| WO | 1994/004690 A1 | 3/1994 |
| WO | 1994/012215 A1 | 9/1994 |
| WO | 1994/025585 A1 | 11/1994 |
| WO | 1995/017085 A1 | 6/1995 |
| WO | 1995/017500 A1 | 6/1995 |
| WO | 1996034103 A1 | 10/1996 |
| WO | 1997/013852 A1 | 4/1997 |
| WO | 1997016537 A1 | 5/1997 |
| WO | 1997/042313 A1 | 11/1997 |
| WO | 1998/024893 A2 | 6/1998 |
| WO | 1998/039416 A1 | 9/1998 |
| WO | 1998/046645 A2 | 10/1998 |
| WO | 1998/050431 A2 | 11/1998 |
| WO | 1999/018212 A1 | 4/1999 |
| WO | 1999/045962 A1 | 9/1999 |
| WO | 2000/026373 A1 | 5/2000 |
| WO | 2000/063403 A2 | 10/2000 |
| WO | 2000/073323 A2 | 12/2000 |
| WO | 2001/053353 A2 | 7/2001 |
| WO | 2001/064929 A1 | 9/2001 |
| WO | 2002/008409 A2 | 1/2002 |
| WO | 2002/012437 A2 | 2/2002 |
| WO | 2002/018948 A2 | 3/2002 |
| WO | 2002/020767 A2 | 3/2002 |
| WO | 2002/036789 A2 | 5/2002 |
| WO | 2002/046237 A2 | 6/2002 |
| WO | 2002/053596 A2 | 7/2002 |
| WO | 2002/066630 A1 | 8/2002 |
| WO | 2002085944 A2 | 10/2002 |
| WO | 2002085945 A2 | 10/2002 |
| WO | 2003/002609 A2 | 1/2003 |
| WO | 2003/029458 A2 | 4/2003 |
| WO | 2003/047336 A1 | 6/2003 |
| WO | 2003/052416 A2 | 6/2003 |
| WO | 2003/061363 A2 | 7/2003 |
| WO | 2003/106495 A2 | 12/2003 |
| WO | 2004/006955 A1 | 1/2004 |
| WO | 2004/009618 A2 | 1/2004 |
| WO | 2004/049794 A2 | 6/2004 |
| WO | 2004/050838 A2 | 6/2004 |
| WO | 2004/058822 A2 | 7/2004 |
| WO | 2004/063381 A2 | 7/2004 |
| WO | 2004058820 A2 | 7/2004 |
| WO | 2004/106375 A1 | 12/2004 |
| WO | 2005/007696 A2 | 1/2005 |
| WO | 2005/019463 A1 | 3/2005 |
| WO | 2005/028510 A2 | 3/2005 |
| WO | 2005/038001 A2 | 4/2005 |
| WO | 2006008548 A2 | 1/2006 |
| WO | 2006/047367 A2 | 5/2006 |
| WO | 2006/117699 A2 | 11/2006 |
| WO | 2006/122442 A1 | 11/2006 |
| WO | 2007/012614 A2 | 2/2007 |
| WO | 2007/059782 A1 | 5/2007 |
| WO | 2007096779 A2 | 8/2007 |
| WO | 2007/117410 A2 | 10/2007 |
| WO | 2008/022391 A1 | 2/2008 |
| WO | 2008/027986 A2 | 3/2008 |
| WO | 2008/035216 A2 | 3/2008 |
| WO | 2008/054606 A2 | 5/2008 |
| WO | 2008/076379 A2 | 6/2008 |
| WO | 2008/081197 A1 | 7/2008 |
| WO | 2008/112922 A2 | 9/2008 |
| WO | 2008/122886 A2 | 10/2008 |
| WO | 2008/151081 A1 | 12/2008 |
| WO | 2009013620 A1 | 1/2009 |
| WO | 2009/018386 A1 | 2/2009 |
| WO | 2009/026660 A1 | 3/2009 |
| WO | 2009/051974 A1 | 4/2009 |
| WO | 2009/052081 A2 | 4/2009 |
| WO | 2009/089004 A1 | 7/2009 |
| WO | 2009/097006 A2 | 8/2009 |
| WO | 2009/129247 A2 | 10/2009 |
| WO | 2009143472 A2 | 11/2009 |
| WO | 2009/157771 A2 | 12/2009 |
| WO | 2010/039900 A2 | 4/2010 |
| WO | 2010/053751 A1 | 5/2010 |
| WO | 2010/054007 A1 | 5/2010 |
| WO | 2010/070263 A1 | 6/2010 |
| WO | 2010/097385 A1 | 9/2010 |
| WO | 2010/109165 A2 | 9/2010 |
| WO | 2010/136598 A1 | 12/2010 |
| WO | 2010/151792 A1 | 12/2010 |

(56) References Cited

FOREIGN PATENT DOCUMENTS

| | | |
|---|---|---|
| WO | 2011/004192 A1 | 1/2011 |
| WO | 2011072204 A1 | 6/2011 |
| WO | 2011/097603 A1 | 8/2011 |
| WO | 2011/143545 A1 | 11/2011 |
| WO | 2011/158009 A1 | 12/2011 |
| WO | 2011/163311 A1 | 12/2011 |
| WO | 2011/163314 A1 | 12/2011 |
| WO | 2012018764 A1 | 2/2012 |
| WO | 2012/063048 A1 | 5/2012 |
| WO | 2012/116926 A1 | 9/2012 |
| WO | 2012/116927 A1 | 9/2012 |
| WO | 2012141798 A1 | 10/2012 |
| WO | 2012/148873 A2 | 11/2012 |
| WO | 2013022782 A1 | 2/2013 |
| WO | 2013/041844 A2 | 3/2013 |
| WO | 2013/041845 A2 | 3/2013 |
| WO | 2013/041846 A2 | 3/2013 |
| WO | 2013/045916 A1 | 4/2013 |
| WO | 2013/059230 A1 | 4/2013 |
| WO | 2013/061078 A1 | 5/2013 |
| WO | 2013/061098 A2 | 5/2013 |
| WO | 2013/079953 A1 | 6/2013 |
| WO | 2013/096142 A1 | 6/2013 |
| WO | 2013/116609 A1 | 8/2013 |
| WO | 2013/134263 A1 | 9/2013 |
| WO | 2014/160179 A1 | 10/2014 |
| WO | 2014/160202 A1 | 10/2014 |
| WO | 2015/143406 A2 | 9/2015 |

OTHER PUBLICATIONS

Andris-Widhopf et al. (2000) "Methods for the generation of chicken monoclonal antibody fragments by phage display," J. Immunol. Methods 242:159-181.
Auerbach et al. (2000) "Establishment and Chimera Analysis of 129/SvEv- and C57BL/6-Derived Mouse Embryonic Stem Cell Lines," BioTechniques, 29(5):1024-1032.
Burton (1995) "Phage display," Immunotechnology 1:87-94.
Festing et al. (1999) "Revised nomenclature for strain 129 mice," Mamm. Genome 10:836.
Gonnet et al. (1992) "Exhaustive Matching of the Entire Protein Sequence Database," Science 256:1443-1445.
Janssens et al. (2006) "Generation of heavy-chain-only antibodies in mice," PNAS 103(41):15130-15135.
Valenzuela et al. (2003) "High-throughput engineering of the mouse genome coupled with high-resolution expression analysis," Nat. Biotech. 21(6):652-659.
Zou et al. (2007) "Heavy chain-only antibodies are spontaneously produced in light chain-deficient mice," J. Exp. Med. 204(13):3271-3283.
PCT Invitation to Pay Fees with respect to PCT/US2015/021892 dated Aug. 10, 2015.
Adams et al. (2005) "A genome-wide, end-sequenced 129Sv BAC library resource for targeting vector construction," Genomics, 86(6):753-758.
Adderson et al. (1991) "Restricted Ig H Chain V Gene Usage in the Human Antibody Response to Haemophilus influenzae Type b Capsular Polysaccharide," The Journal of Immunology, 147:1667-1674.
Adderson et al. (1993) "Restricted Immunoglobulin VH Usage and VDJ Combinations in the Human Response to Haemophilus influenzae Type b Capsular Polysaccharide," J. Clin. Invest., 91:2734-2743.
Al-Lazikani, B. et al., (1997) "Standard conformations for the canonical structures of immunoglobulins," J. Mol. Biol., 273(4):927-48.
Almagro et al. (2004) "Identification of differences in the specificity-determining residues of antibodies that recognize antigens of different size: implications for the rational design of antibody repertoires," Journal of Molecular Recognition, 17(2):132-143.

Alt et al. (1982) "Joining of immunoglobulin heavy chain gene segments: Implications from a chromosome with evidence of three D-$J_H$ fusions," PNAS, 79:4118-4122.
Altschul et al. (1990) "Basic local alignment search tool," J. Mol. Biol., 215(3): 403-410.
Altschul et al. (1997) "Gapped BLAST and PSI-BLAST: a new generation of protein database search programs," Nucleic Acids Res. 25:3389-3402.
Altschul et al. Methods in Enzymology.
Amit and Itskovitz-Eldor (2009) "Embryonic Stem Cells: Isolation, Characterization and Culture," Adv. Biochem. Eng. Biotechnol, 114:173-184.
Arnaout, R. et al., High-resolution description of antibody heavy-chain repertoires in; humans PLoS One, 6(8):e22365 (2011).
Arnold, L. et al., Development of B-1 cells: segregation of phosphatidyl choline-specific B cells to the B-1 population occurs after immunoglobulin gene expression, J. Exp. Med., 179:1585-1595 (1994).
Askew, G.R. et al., Site-directed point mutations in embryonic stem cells: a gene-targeting tag-and-exchange strategy, Mol. Cell Biol., 13(7):4115-24 (1993).
Astellas Negotiates $295M License Extension to Regeneron's VelocImmune mAb Platform, Genetic Engineering & Biotechnology News, Jul. 28, 2010, 2 pages.
Aucouturier, P.et al., Monoclonal Ig L chain and L chain V domain fragment crystallization in myeloma-associated Fanconi's syndrome, J. Immunol., 150( 8):3561-3568 (1993).
Author Not Known (2007) "Breeding Strategies for Maintaining Colonies of Laboratory Mice," A Jackson Laboratory Resource Manual, pp. 1-29.
Author Not Known, Additional post-filing data and letter filed by the Applicant/Patentee for corresponding European application 09075279.1, now opposed patent EP 2147594 B1, 4 pages (Jun. 13, 2013).
Author Not Known, Chapter 6: The Development of B Lymphocytes, Immuno Biology: The Immune System in Health and Disease, 4th Edition, Janeway et al. ed., pp. 195-208 (1999).
Author Not Known, Chapter 8: The Development and Survival of Lymphocytes, Janeway's Immunobiology, 8th Edition, Eds. Kenneth Murphy et al, Garland Science (ISBN: 9780815342434), whole document, in particular p. 279 and Figure 8.4, (2011).
Author Not Known, Mouse strain, document #3 submitted with Third Party Observation, filed in GB2012052956, 4 pages (Mar. 26, 2014).
Author Not Known, Next generation transgenic mice for therapeutic human antibodies, Description of MeMoTM, filed by the Applicant/Patentee in prosecution for corresponding European application 09075279.1, now opposed patent EP 2147594 B1, 2 pages (Dec. 22, 2011).
Author Not Known, V-BASE Sequence Directory, 6 pages, retrieved on Jun. 6, 2016 <http://www2.mrc-lmb.cam.ac.uk/vbase/list2.php.
Azwai et al. (1996) "Immunonoglobulins of Camel (Camelus dromedarius) Colostrum," J. Comp. Pathol., 114:273-282.
Azzazy and Highsmith (2002) "Phage display technology: clinical applications and recent innovations," Clin. Biochem. 35:425-445.
Baeuerle, P.A. and Reinhardt, C., Bispecific T-cell engaging antibodies for cancer; therapy, Cancer Res., 69(12):4941-4 (2009).
Baird and Myszka (2001) "Current and emerging commercial optical biosensors," J. Molecular Recognition, 14:261-268.
Bando et al. (2004) "Characterization of VH gene expressed in PBL from children with atopic diseases: detection of homologous VH1-69 derived transcripts from three unrelated patients," Immunology Letters, 94:99-106.
Bankovich et al. (2007) "Structural Insight into Pre-B Cell Receptor Function," Science, 316(5822):291-294.
Barthelemy et al. (2008) "Comprehensive Analysis of the Factors Contributing to the Stability and Solubility of Autonomous Human VH Domains," J. Bio. Chem., 283(6):3639-3654.
Baseggio et al. (2010) "CD5 expression identifies a subset of splenic marginal zone lymphomas with higher lymphocytosis: a clinico-pathological, cytogenetic and molecular study of 24 cases," Haematologica, 95(4):604-612.

(56) References Cited

OTHER PUBLICATIONS

Bates et al. (2007) "Chromosomal position of a VH gene segment determines its activation and inactivation as a substrate for V(D)J recombination," Journal of Experimental Medicine, 204(13):3247-3256.

Bauer, S. et al., Structure and pre-B lymphocyte restricted expression of the VpreB gene in humans and conservation of its structure in other mammalian species,The EMBO Journal, 7(1):111-116 (1988).

Berberian et al. (1991) "A VH Clonal Deficit in Human Immunodeficiency VirUS Positive Individuals Reflects a B-Cell Maturational Arrest," Blood, 78(1):175-179.

Berman et al (1988) "Content and organization of the human Ig $V_H$ locus: definition of three new $V_H$ families and linkage to the Ig $C_H$ locus," EMBO 7(3) 727-738.

Billiard, F. et al., Ongoing Dll4-Notch signaling is required for T-cell homeostasis in the adult thymus, Eur. J. Immunol., 41(8):2207-16 (2011).

Blaas, L. et al., Bacterial artificial chromosomes improve recombinant protein production in mammalian cells, BMC Biotechnol., 9:3 (2009).

Blankenstein et al. (1987) "Immunoglobulin $V_H$ region genes of the mouse are oranized in overlapping clusters," Eur. J. Immunol., 17:1351-1357.

Bode, J. et al., The transgeneticist's toolbox: novel methods for the targeted modification of eukaryotic genomes, Biol. Chem., 381(9-10):801-13 (2000).

Bot, A. et al., V2-Light Chain Genes Reconstitute Immune Responses to Defined Carbohydrate Antigens or Haptens by Utilizing Different VH Genes, Molecular Immunology, 33(17/18):1359-1368 (1996).

Brevini et al. (2010) "No shortcuts to pig embryonic stem cells," Theriogenology 74(4):544-550.

Brezinschek et al. (1995) "Analysis of the Heavy Chain Repertoire of Human Peripheral B Cells Using Single-Cell Polymerase Chain Reaction," Journal of Immunology, 155:190-202.

Brezinschek, H. et al., Pairing of variable heavy and variable kappa chains in individual naïve and memory B cells, J. Immunol., 160(10):4762-4767 (1998).

Brezinschek, H.P. et al., Analysis of the human VH gene repertoire. Differential effects of selection and somatic hypermutation on human peripheral CD5(+)/IgM+ and CD5(−)/IgM+ B; Cells, J. Clin. Invest., 99(10):2488-501 (1997).

Brodeur et al. (1984) "The immunoglobulin heavy chain variable region (Igh-V) locus in the mouse I. One hundred IgH-V genes comprise seven families of homologous genes," Eur. J. Immunol., 14:922-930.

Brouwers et al. (2015) "Unexpected Phenotypes in Mouse Models Carrying the Human Growth Hormone Minigene to Enhance Transgene Expression," Journal of Steroids & Hormonal Science, 6(2):1-2.

Bruchez et al. (1998) "Semiconductor Nanocrystals as Fluorescent Biological Labels," Science 281: 2013-2016.

Brüggemann et al. (1989) "A repertoire of monoclonal antibodies with human heavy chains from transgenic mice," Proceedings of the National of Academy of Science USA, 86:6709-6713.

Brüggemann and Neuberger (1996) "Strategies for expressing human antibody repertoires in transgenic mice," Review Immunology Today, 192(17):391-397.

Brüggemann (2001) "Human Antibody Expression in Transgenic Mice," Archivum Immunologiae et Therapiae Experimentalis, 49:203-208.

Brüggemann (2004) "Human Monoclonal Antibodies from Translocus Mice," Molecular Biology of B Cells, Eds. Honjo, T. and Neuberger, M.S., New York, NY: Academic Press, pp. 547-561.

Bruggemann et al. (2006) "Heavy-Chain-Only Antibody Expression and B-Cell Development in the Mouse," Crit. Rev. Immunol., 26(5):377-390.

Butler, (1998) "Immunoglobulin diversity, B-cell and antibody repertoire development in large farm animals," Rev. Sco. Tech. Off. Int. Epiz., 17(1):43-70.

Campbell, K.H. et al., Sheep cloned by nuclear transfer from a cultured cell line, Nature, 380(6569):64-6 (1996).

Carbonari et al. (2005) "Hepatitis C Virus Drives the Unconstrained Monoclonal Expansion of VH1-69-Expressing Memory B Cells in Type II Cryoglobulinemia: A Model of Infection-Driven Lymphomagenesis," The Journal of Immunology, 174:6532-6539.

Carmack, C. et al., Influence of a V kappa 8 L chain transgene on endogenous rearrangements and the immune response to the HA(Sb) determinant of influenza virus, J. Immunol., 147(6):2024-2033 (1991).

Carter, P., Bispecific human IgG by design, Journal of Immunological Methods, 248(1-2):7-15 (2001).

Cascalho, M. et al., A quasi-monoclonal mouse, Science, 272(5268):1649-1652 (1996).

Casellas, R. et al., Contribution of receptor editing to the antibody repertoire, Science, 291(5508):1541-4 (2001).

Cavelier et al. (1997) "B lineage-restricted rearrangement of a human Ig kappa transgene," Eur J. Immunol. 27(7):1626-1631.

Chan et al. (2001) "VH1-69 gene is preferentially used by hepatitis C virUS associated B cell lymphomas and by normal B cells responding to the E2 viral antigen," Blood, 97(4):1023-1026.

Chang et al. (1984) "Immunologic memory to phosphocholine. IV. Hybridomas representative of Group I (T15-like) and Group II (non-T15-like) antibodies utilize distinct VH genes," J. Immunol., 132(3):1550-1555.

Charles et al. (2011) "A flow cytometry-based strategy to identify and express IgM from VH1-69+ clonal peripheral B cells," Journal of Immunological Methods, 363:210-220.

Chen, C. et al., Deletion and Editing of B Cells that Express Antibodies to DNA, Journal of Immunology, 152(4):1970-1982 (1994).

Cheval et al. (2012) Of Mice and Men: Divergence of Gene Expression Patterns in Kidney, PLoS One, 7(10):e46876 (12 pages).

Cho, Chunghee, (2012) "Testicular and epididymal ADAMs: experssion and function during fertilization," Nature Reviews Urology, 9:550-560.

Choi et al. (2004) "Characterization and comparative genomic analysis of intronless Adams with testicular gene expression," Genomics, 83(4):636-646.

Choi et al. (2011) "Expression of the metabotropic glutamate receptor 5 (mGluR5) induces melanoma in transgenic mice," PNAS, 108(37):15219-15224.

Choi et al. (2013) "Identification and characterizaion of promoter and regulatory regions for mouse Adam2 gene expression," Molecular Biology Reports, 40:787-796.

Chothia, C. and Lesk, A.M., Canonical structures for the hypervariable regions of; Immunoglobulins, J. Mol. Biol., 196(4):901-17 (1987).

Choulika, A. et al., Induction of homologous recombination in mammalian chromosomes by using the I-SceI system of Saccharomyces cerevisiae, Mol. Cell. Biol., 15:4 1968-73 (1995).

Clark and Whitelaw, (2003) "A future for transgenic livestock, National Reviews Genetics," 4(10):825-833.

Cocea et al. (1999) "A targeted deletion of a region upstream from the Jkppa cluster impairs kappa chain rearrangement in cis in mice and in the 103/bcl2 cell line," J. Exp. Med., 189(9):1443-1450.

Cohen-Tannoudji, M. et al., I-SceI-induced gene replacement at a natural locus in; embryonic stem cells, Mol. Cell. Biol., 18(3):1444-8 (1998).

Collins, A. et al., The reported germline repertoire of human immunoglobulin kappa chain genes is relatively complete and accurate, Immunogenetics, 60:669-676 (2008).

Combriato et al. (2002) "Regulation of Human Igl Light Chain Gene Expression," The Journal of Immunology, 168:1259-1266.

Conrath et al. (2001) "β-Lactamase Inhibitors Derived from Single-Domain Antibody Fragments Elicited in the Camelidae," Antimicrob. Agents Chemother., 45(10):2807-2812.

Corcos, D. et al, Pre-B-cell development in the absence of lambda 5 in transgenic mice expressing a heavy-chain disease protein, Curr. Biol., 5(10):1140-8 (1995).

Cowen, N.J. et al., Purification and Sequence Analysis of the mRNA Coding for an Immunoglobulin Heavy Chain, European J. of Biochem., 61(2): 355-368 (1976).

(56) References Cited

OTHER PUBLICATIONS

Dalton (2009) "When a Llama Is Laid Back, It's Not the Only Beneficiary," The Wall Street Journal, published online at http://www.wsj.com, 3 pages.
Davidkova et al. (1997) "Selective Usage of VH Genes in Adult Human B Lymphocyte Repertoires," Scand. J. Immunol., 45:62-73.
Davies, N. et al., Creation of Mice Expressing Human Antibody Light Chains by Introduction of a Yeast Artificial Chromosome Containing the Core Region of the Human Immunoglobulin ? Locus, Nature Biotechnology 11:911-914, (1993).
Davies et al. (1996) "Single antibody domains as small recognition units: design and in vitro antigen selection of camelized, human VH domains with improved protein stability," Protein Eng., 9(6):531-537.
De Gensst et al. (2006) Antibody repertoire development in camelids. Dev. Comp. Immunol, 30:187-198.
De Haard et al. (2005) "Llama Antibodies against a Laclococcal Protein Located at the Tip of the Phage Tail Prevent Phage Infecton," J. Bacteriol., 187(13):4531-4541.
De Kruif, J. et al., Human Immunoglobulin Repertoires against Tetanus Toxoid Contain a Large and Diverse Fraction of High-Affinity Promiscuous VH Genes, Journal of Molecular Biology, 387:548-558 (2009).
De Kruif, J. et al., Rapid selection of cell subpopulation-specific human monoclonal antibodies from a synthetic phage antibody library, Proc. Natl. Acad. Sci. U S A, 92(9):3938-42 (1995).
De Wildt, R. et al., Analysis of heavy and light chain pairings indicates that receptor editing shapes the human antibody repertoire, J. Mol. Biol., 285(3):895-901 (1999).
Dechiara, T.M. et al., Chapter 16: VelociMouse: Fully ES Cell-Derived F0 Generation Mice Obtained from the Injection of ES Cells into 8-Cell Stage Embryos, Gene Knockout Protocols: Second Edition, vol. 530, Humana Press (2009).
Deegan (1976) "Bence Jones Proteins: Nature, Metabolism, Detection and Significance," Annals of Clinical and Laboratory Science, 6(1):38-46.
Deisenhofer, J., Crystallographic Refinement and Atomic Models of a Human Fc Fragment and Its Complex with Fragment B of Protein A from *Staphylococcus aureus* at 2.9- and 2.8-? Resolution, Biochemistry, 20(9):2361-2370 (1981).
Desmyter, A. et al., Crystal structure of a camel single-domain VH antibody fragment in complex with lysozyme, Nat. Struct. Biol., 3(9):803-11 (1996).
Dinnyés, A. et al., Somatic cell nuclear transfer: recent progress and challenges, Cloning Stem Cells, 4(1):81-90 (2002).
Donoho, G. et al., Analysis of gene targeting and intrachromosomal homologous recombination stimulated by genomic double-strand breaks in mouse embryonic stem cells, Mol. Cell. Biol., 18(7):4070-8 (1998).
Donohoe, M. et al., Transgenic Human Lambda5 Rescues the Murine Lambda5 Nullizygous Phenotype, Journal of Immunology, 164:5269-5276 (2000).
Dumoulin et al. (2002) "Single-domain antibody fragments with high conformational stability," Protein Sci., 11:500-515.
Echelard, Y., Year of the ox, Nat. Biotechnol., 27(2):146-7 (2009).
Edmundson et al. (1993) "Priniciples and Pitfalls in Designing Site-Directed Peptide Ligands," Proteins: Structure, Function, and Genetics, Wiley-Liss, Inc., 16:246-267.
Edwards et al. (2008) "The ADAM metalloproteinases, Molecular Aspects of Medicine," 29(5):258-289.
Els Conrath, K. et al., Camel single-domain antibodies as modular building units in bispecific and bivalent antibody constructs, J. Biol. Chem., 276(10):7346-50 (2001).
Enever et al. (2009) "Next generation immunotherapeutics—honing the magic bullet. Current Opinion in Biotechnology," 20:405-411.
Engel, P. et al., Abnormal B Lymphocyte Development, Activation, and Differentiation in Mice that Lack or Overexpress the CD19 Signal Transduction Molecule, Immunity, 3:39-50 (1995).

Epinat, J.C., et al. A novel engineered meganuclease induces homologous recombination in yeast and mammalian cells, Nucleic Acids Res., 31(11):2952-62 (2003).
Ewert et al. (2002) "Biophysical Properties of Camelid VHH Domains Compared to Those of Human VH3 Domains," Biochem., 41:3628-3636.
Ewert, S. et al., Biophysical properties of human antibody variable domains, J. Mol. Biol., 325(3):531-53 (2003).
Farner, N.L. et al., Molecular mechanisms and selection influence the generation of the human V lambda J lambda repertoire, J. Immunol., 162(4):2137-45 (1999).
Featherstone, K et al. (2010) "The mouse immunoglobulin heavy chain V-D intergenic sequence contains insulators that may regulate ordered V(D)J recombination," J. Biol. Chem., 285(13): 9327-9338.
Fell, H.P. et al., Homologous recombination in hybridoma cells: heavy chain chimeric antibody produced by gene targeting, Proc. Natl. Acad. Sci. U S A., 86(21):8507-11 (1989).
Fischer, N. and Léger, O., Bispecific antibodies: molecules that enable noveltherapeutic strategies, Pathobiology, 74(1):3-14 (2007).
Flavell, D.J., et al., Therapy of human T-cell acute lymphoblastic leukaemia with a combination of anti-CD7 and anti-CD38-SAPORIN immunotoxins is significantly better than therapy with each individual immunotoxin, Br. J. Cancer., 84(4):571-8 (2001).
Fraenkel, S. et al., Allelic 'choice' governs somatic hypermutation in vivo at the immunoglobulin kappa-chain locus, Nat. Immunol., 8(7):715-722 (2007).
Fussenegger, M. et al., Genetic optimization of recombinant glycoprotein production by mammalian cells, Tibtech, 17:35-42 (1999).
Gallo et al. (2000) "The human immunoglobulin loci introduced into mice: V (D) and J gene segment usage similar to that of adult humans," Eur. J. Immunol., 30(2):534-540.
Gama Sosa et al. (2010)"Animal transgenesis: an overview," Brain Structure & Function, 214(2-3):91-109.
Gavilondo and Larrick (2002) BioTechniques 29:128-145.
Gavish et al. (1977) "Comparison of the fine specificity of anti-dinitrophenyl-combining site composed of either VL dimer or VL and VH of protein 315," Biochemistry, 16(14):3154-3159.
Gay, D. et al., Receptor editing: an approach by autoreactive B cells to escape tolerance, J. Exp. Med., 177(4):999-1008 (1993).
GenBank accession No. NT_114985, p. 1, first referenced Dec. 1, 2005, last updated Feb. 9, 2015.
GenBank Accession No. X97051, GI:564822, first referenced Jan. 9, 1997, updated Nov. 14, 2006 (29 pages).
GenBank Accession No. ABA26122, immunoglobulin light chain variable region, partial [*Homo sapiens*], Rabquer et al., 2 pages, first referenced Dec. 31, 2005.
GenBank Accession No. M87478, Human rearranged IgK mRNA VJC region, Aucouturier et al., 1 page, first referenced Mar. 3, 1992, first seen at NCBI Apr. 27, 1993.
Geraldes et al. (2007) "Ig heavy chain promotes mature β cell survival in the absence of light chain," J. Immunol., 179:1659-1668.
Ghahroudi et al. (1997) "Selection and identification of single domain antibody fragments from camel heavy chain antibodies," FEBS Letters, 414:521-526.
Giallourakis et al. (2010) "Elements between the IgH variable (V) and diversity (D) clusters influence antisense transcription and lineage-specific V(D)K recombination," PNAS, 107(51):22207-22212.
Giddings, G. et al., Transgenic plants as factories for biopharmaceuticals, Nat. Biotechnol., 18(11):1151-5 (2000).
Giersberg et al. (2010) "Covalent dimerization of camelidae anti-human TNF-alpha single domain antibodies by the constant kappa light chain domain improves neutralizing activity," Biotech and Bioeng., 106(1):161-166, (submitted as preprint publication, pp. 1-20).
Goletz, S. et al., Selection of Large Diversities of Antiidiotypic Antibody Fragments by Phage Display, J. Mol. Biol. 315:1087-97, (2002).
Goni et al. (1985) "Sequence similarities and cross-idiotypic specificity of L chains among human monoclonal IgMk with anti-gamma-globulin activity," J. Immunol, 135(6):4073-9.

(56) References Cited

OTHER PUBLICATIONS

Gonzalez-Fernandez, A. and Milstein, C., Analysis of somatic hypermutation in mouse Peyer's patches using immunoglobulin kappa light-chain transgenes, PNAS USA, 90:9862-9866 (1993).
Goodhardt et al., Rearrangement and Expression of rabbit immunoglobulin K light chain gene in transgenic mice; Jun. 1987; PNAS, 84: 4229-4233.
Gorman et al. (1996) "The Ig(kappa) enhancer influences the ratio of Ig(kappa) versus Ig(lambda) B lymphocytes," Immunity, 5(3):241-252.
Goyenechea, B. and Milstein, C., Modifying the sequence of an immunoglobulin V-gene alters the resulting pattern of hypermutation, PNAS USA, 93:13979-13984 (1996).
Goyenechea, B. et al., Cells strongly expressing Ig(kappa) transgenes show clonal recruitment of hypermutation: a role for both MAR and the enhancers, EMBO J., 16(13):3987-94 (1997).
Grawunder et al. (1995) "Induction of sterile transcription from the kappa L chain gene locus in V(D)J recombinase-deficient progenitor B cells," International Immunology, 7(12):1915-1925.
Green, L. and Jakobovits, A., Regulation of B cell development by variable gene complexity in mice reconstituted with human immunoglobulin yeast artificial chromosomes, J. Exp. Med., 188(3):483-495 (1998).
Green, L.et al. (1994) "Antigen-specific human monoclonal antibodies from mice engineered with human Ig heavy and light chain YACs," Nature Genetics, 7(1):13-21.
Gunther et al. (2007) "SuperHapten: a comprehensive database for small immunogenic compounds," Nucleic Acid Research, 35:D906-D910.
Hagiwara, S., Transgenic expression of VpreB-3 under the control of the immunoglobulin heavy chain enhancer and SV40 promoter, Kobe J. Med. Sci., 42(1):43-59 (1996). Abstract Only.
Haines and Brodeur (1998) Accessibility changes across the mouse Igh-V locus during B cell development, Eur. J. Immunol., 28:4228-4235.
Hamers-Casterman et al. (1993) "Naturally occuring antibodies devoid of light chains," Nature, 363:446-448.
Han et al. (2009) "Comprehensive analysis of reproductive ADAMs: relationship of ADAM4 and ADAM6; with an ADAM complex required for fertilization in mice," Biology of Reproduction, 80(5):1001-1008.
Harding and Lonberg (1995) "Class switching in human immunoglobulin transgenic Mice," Ann. N Y Acad. Sci., 764:536-546.
Hardy, R.R and Hayakawa, K., B cell development pathways, Annu. Rev. Immunol., 19:595-621 (2001).
Harmsen et al. (2000) "Llama heavy-chain V regions consist of at least four distinct subfamilies revealing novel sequence features," Mol. Immunol., 37:579-590.
Harmsen et al (2007) "Properties, production, and applications of camelid single-domain antibody fragments," Appl. Microbiol. Biotech., 77:13-22.
Hartley, S. and Goodnow, C., Censoring of self-reactive B cells with a range of receptor affinities in transgenic mice expressing heavy chains for a lysozyme-specific antibody, International Immunology, 6:1417-1425 (1994).
Helms and Wetzel (1995) "Destabilizing loop swaps in the CDRs of an immunoglobulin $V_L$ domain," Protein Science, 4:2073-2081.
Hendershot et al. (1987) "Assembly and secretion of heavy-chains that do not associate post translationally with immunoglobulin heavy-chain binding-protein," J. Cell Biol., 104(3):761-767.
Hendricks et al. (2010) "Organization of the variable region of the immunoglobulin heavy-chain gene locus of the rat," Immunogenetics, 62(7):479-486.
Hengstschlager, M. et al., A lambdal transgene under the control of a heavy chain promoter and enhancer does not undergo somatic hypermutation, Eur. J. Immunol., 24:1649-1656 (1994).
Hiatt, A. et al. Production of antibodies in transgenic plants, Nature, 342(6245):76-8 (1989).
Hirabayashi et al. (1995) "Kinetic analysis of the interactions of recombinant human VpreB and Ig V domains," J. Immunol., 155:1218-1228.
Hochedlinger, K. and R. Jaenisch, Monoclonal Mice Generated by Nuclear Transfer from Mature B and T Donor Cells, Nature, 415(6875):1035-1038, (2002).
Hoiruchi and Blobel (2005) Studies from Adam Knockout Mice, in Hooper and Lendeckel, The ADAM Family of proteases, Netherlands 2005, Springer (37 pages).
Holt, et al. (2003) "Domain antibodies: proteins for therapy," Trends in Biotech., 21(11):484-490.
Hömig-Hölzel, C. et al., Constitutive CD40 signaling in B cells selectively activates the noncanonical NF-kappaB pathway and promotes lymphomagenesis, J. Exp. Med., 205(6):1317-29 (2008).
Hoogenboom (1997) TIB Tech. 15:62-70.
Hoogenboom and Chames (2000) "Antibodies isolated from an animal (e.g., a mouse) that is transgenic for human immunoglobulin genes," Immunology Today 21:371-378.
Houdebine, L.M. Transgenic Animals: Generation and Use. Amsterdam: Harwood Academic Publishers.pp. 397-403 (1997).
House mouse (*Mus musculus*) Igh locus on chromosome 12 (12F2) strain C57BL/6 pp. 1-5; dowloaded Aug. 26, 2016.
Huang et al. (1993) "A Majority of Ig H Chain cDNA of Normal Human Adult Blood Lymphocytes Resembles cDNA for Fegal Ig and Natural Autoantibodies," The Journal of Immunology, 151(10):5290-5300.
Huls, G. et al., Antitumor immune effector mechanisms recruited by phage display-derived fully human IgG1 and IgA1 monoclonal antibodies, Cancer Res., 59(22):5778-84 (1999).
Hussack et al. (2012) "A VL single-domain antibody library shows a high-propensity to yield non-aggregating binders," Protein Engineering, Design & Selection, 25(6):313-318.
Ill et al. (1997) "Design and construction of a hybrid immunoglobulin domain with properties of both heavy and light chain variable regions," Protein Engineering, 10(8):949-957.
IMGT V-Quest Analysis of Sequence of Gen Bank M87478, 7 pages.
Inlay, M. et al., Essential roles of the kappa light chain intronic enhancer and 3' enhancer in kappa rearrangement and demethylation, Nat. Immunol., 3(5):463-8 (2002).
Irving, R.A. et al., Ribosome display and affinity maturation: from antibodies to single V-domains and steps towards cancer therapeutics, J. Immunol. Methods, 248(1-2):31-45 (2001).
Jakobovits, A. et al., From XenoMouse technology to panitumumab, the first fully human antibody product from transgenic mice, Nature Biotechnology, 25(10):1134-1143 (2007).
Jakobovits, A., Production of fully human antibodies by transgenic mice, Curr. Opin. Biotechnol., 6(5):561-6 (1995).
Jakobovits, Therapeutic Antibodies from XenoMouse Transgenic Mice, Recombinant Antibodies for Immunotherapy, Ed. Little, M., New York, NY: Cambridge University Press, Chapter 7, pp. 89-99 (2009).
Janeway's Immunobiology, Seventh Edition, Murphy, Travers and Walpot, eds., Garland Science, New York and London, Ch. 4, pp. 145-155, and Ch. 7, pp. 266-267 (2008).
JAX Mice Database, Printout from http://jaxmice.jax.org/strain/002288.html, printed Aug. 23, 2013, pp. 1-2.
Jendeberg, L. et al., Engineering of Fc1 and Fc3 from human immunoglobulin G to analyse subclass specificity for staphylococcal protein A1, Journal of Immunological Methods, 201:25-34 (1997).
Jendreyko, N. et al., Intradiabodies, bispecific, tetravalent antibodies for the simultaneous functional knockout of two cell surface receptors, J. Biol. Chem., 278(48):47812-9 (2003).
Johnson et al. (1997) "Ig VH1 Genes Expressed in B Cell Chronic Lymphocytic Leukemia Exhibit Distinctive Molecular Features," The Journal of Immunology, 158:235-246.
Johnston et al. (2006) "Complete Sequence Assembly and Characterization of the C57BL/6 Mouse Ig Heavy Chain V Region[1]," J. Immunol., 176:4221-4234.
Jolly, C. et al., Rapid methods for the analysis of immunoglobulin gene hypermutation: application to transgenic and gene targeted mice, Nucleic Acids Research, 25(10):1913-1919 (1997).

(56) References Cited

OTHER PUBLICATIONS

Jones, D. et al., High-level expression of recombinant IgG in the human cell line per.c6, Biotechnol. Prog., 19(1):163-8 (2003).
Joyner, A.L. ed., Gene Targeting: A Practical Approach, Second Edition, Oxford University Press, entire book, 193 pages. (2000).
Kaartinen et al. (1988) "Combinatorial association of V genes: One VH gene codes for three non-cross-reactive monoclonal antibodies each specific for a different antigen (phOXAZOLONE, NP or GAT)," Mol. Immunol., 25(9):859-865.
Kabat and Wu, (1991) "Identical V region amino acid sequences and segments of sequences in antibodies of different specificities. Relative contributions of VH and VL genes, minigenes, and complementarity-determining regions to binding of antibody-combining sites," J. Immunol., 147(5):1709-1719.
Kantor et al. (1997) "An Unbiased Analysis of VH-D-JH Sequences from B-1a, B-1b, and Conventional B Cells," The Journal of Immunology, 158: 1175-1186.
Kasprzyk, P.G. et al., Therapy of an animal model of human gastric cancer using a combination of anti-erbB-2 monoclonal antibodies, Cancer Res., 52(10):2771-6 (1992).
Kaushik et al, "Stochastic pairing of heavy-chain and k light-chain variable gene families occurs in polyclonally activated B cells," Proc. Natl. Acad. Sci. USA, vol. 87: 4932-4936 (1990).
Kaushik et al. (2002) "Novel insight into antibody diversification from cattle," Veterinary Immunology and Immunopathology, 87(3-4):347-350.
Kellermann and Green (2002) "Antibody discovery: the use of transgenic mice to generate human monoclonal antibodies for therapeutics ," Current Opinion in Biotechnology 13:593-597.
Kim et al. (2006) "Expression and relationship of male reproductive ADAMs in mouse," Biology of Reproduction, 74(4):744-750.
Kingzette et al.(1998) "Trans-chromosomal recombination within the Ig heavy chain switch region in B lymphocytes," PNSA, 95(20):11840-11845.
Kitamura et al. (1991) "A B cell-deficient mouse by targeted disruption of the membrane exon of the immunoglobulin μ chain gene," Nature, 350:423-426.
Klebig, (1995) "Ectopic Expression of the Agouti Gene in Transgenic Mice Causes Obesity, Features fo Type II Diabetes, and Yellow Fur," PNAS 92:4728-4732.
Klöhn, P.C. et al., IBC's 23rd Annual Antibody Engineering, 10th Annual Antibody Therapeutics international conferences and the 2012 Annual Meeting of the Antibody Society: Dec. 3-6, 2012, San Diego, CA, Mabs, 5(2):178-201 (2013).
Klotz, E. et al., Somatic hypermutation of a lambda2 transgene under the control of the lambda enhancer or the heavy chain intron enhancer, J. Immunol., 157:4458-4463 (1996).
Klotz, E. et al., Somatic hypermutation of an artificial test substrate within an Ig kappa transgene, J. Immunol., 161:782-790 (1998).
Knappik, A. et al., Fully synthetic human combinatorial antibody libraries (HuCAL) based on modular consensus frameworks and CDRs randomized with trinucleotides, J. Mol. Biol., 296(1):57-86 (2000).
Kobayashi and Oyama (2011) "Antibody engineering toward high-sensitivity high-throughput immunosensing of small molecules," The Royal Society of Chemistry, Analyst, 136:642-651 (DOI: 10.1039/c0an00603c).
Kong et al. (2009) "Transgene expression is associated with copy number and cytomegalovirus promoter methylation in transgenic pigs," PLoS One 4(8):1-10.
Kong, Q. et al., A lambda 3' enhancer drives active and untemplated somatic hypermutation of a lambda1 transgene, J. Immunol., 161:294-301 (1998).
Kontermann, R.E., Dual targeting strategies with bispecific antibodies, MAbs., 4(2):182-97 (2012).
Kroesen, B.J. et al., Bispecific antibodies for treatment of cancer in experimental animal models and man, Adv. Drug Deliv. Rev., 31(1-2):105-129 (1998).
Kunert et al. (2004) "Characterization of Molecular Features, Antigen-Binding, and in Vitro Properties of IgG and IgM Variants of 4E10, an Anti-HIV Type 1 Neutralizing Monoclonal Antibody," Aids ReSearch and Human Retroviruses, 20(7):755-762.
Kuroiwa et al. (2002) "Cloned transchromosomic calves producing human immunoglobulin," Nat. Biotechnol., 20(9):889-894.
Kuroiwa et al. (2004) "Sequential targeting of the genes encoding immunoglobulin-μ and prion protein in cattle," Nature Genetics, 36:775-780.
Lam, K. et al., In Vivo Ablation of Surface Immunoglobulin on Mature B Cells by Inducible Gene Targeting Results in Rapid Cell Death, Cell, 90:1073-1083 (1997).
Lantto, J. et al., Capturing the natural diversity of the human antibody response against vaccinia virus, J Virol, 85(4):1820-33 (2011).
Larrick, J.W. and Thomas, D.W., Producing proteins in transgenic plants and animals, Curr. Opin. Biotechnol., 12(4):411-8 (2001).
Lavial and Pain, (2010) "Chicken embryonic stem cells as a non-mammalian embryonic stem cell model" Develop. Groth Diff., 52(1):101-114.
Le Gall, F. et al., Effect of linker sequences between the antibody variable domains on the formation, stability and biological activity of a bispecific tandem diabody, Protein Eng. Des. Sel., 17(4):357-66 (2004).
Leclercq et al. (1989) "A novel germ-like JK transcript starting immediately upstream of JK1," Nucleic Acids Research, 17(17):6809-6819.
Lee et al. (1999) "BiP and Immunoglobulin Light Chain Cooperate to Control the Folding of Heavy Chain and Ensure the Fidelity of Immnoglobulin Assembly," Molecular Biology of the Cell, 10:2209-2219.
Lee, H. et al., Human C5aR knock-in mice facilitate the production and assessment of anti-inflammatory monoclonal antibodies, Nat. Biotechnol., 24(10):1279-84 (2006).
Lee et al. (2014) "Complete humanization of the mouse immunoglobulin loci enables efficient therapeutic antibody discovery," Nature Biotechnology, 32(4):356-363.
Lefranc, (2000) "Nomoclature of the Human Immunoglobulin Genes Current Protocols in Immunology," Supplement 40:1.1P.1-A.1P.37.
Lefranc, (2001) "Nomeclature of the human immunoglobulin lambda (IGL) genes," Experimental and Clinical Immunogenetics, S. Karger Basel C.H., 18(4):242-254.
Lefranc, M-P. and Lefranc, G., The Immunoblobulin Facts Books-,San Diego/San Francisco/New York/Boston/London/Sydney/Tokyo: Academic Press, entire book, pp. 1-457 (2001).
Lefranc, M.P. Nomenclature of the human immunoglobulin heavy (IGH) genes, Exp. Clin. Immunogenet., 18(2):100-16 (2001).
Lefranc, M.P., Nomenclature of the human immunoglobulin kappa (IGK) genes, Exp. Clin. Immunogenet., 18(3):161-74 (2001).
Lefranc, (2004) Molecular Biology of B Cells. London: Elsevier Academic Press, Ed. Honjo, Chapter 4 pp. 37-59.
Leitzgen et al. (1997) "Assembly of Immunoglobulin Light Chains as a Prerequisite for Secretion," Journal Biological Chemistry., 272(5):3117-3123.
Liao, M.J. and Van Dyke, T., Critical role for Atm in suppressing V(D)J recombination-driven thymic lymphoma, Genes Dev., 13(10):1246-50 (1999).
Lin et al. (1990) "Research of Immune Globulin in Mice," Guangzhou Medical Journal, 1:49-50 and English translation.
Lindhofer, H. et al., Preferential Species-Restricted Heavy/Light Chain Pairing in Rat/Mouse Quadromas, The Journal of Immunology, 155:219-225 (1995).
Little et al. (2000) "Of mice and men: hybridoma and recombinant antibodies.," Immunology Today 21:364-370.
Liu (2009) "Isolation and characterization of human anti-VEGF (165) monoclonal antibody with anti-tumor efficacy from transgenic mice expressing human immunoglobulin loci," Cancer Letters, 273(1):28-34.
Liu et al. (2014) "Primary Genetic Investigation of a Hyperlipidemia Model: Molecular Characteristics and Variants of the Apolipoprotein E Gene in Mongolian Gerbil," Biomed. Research International, (9 pages).
Logtenberg, T., Antibody cocktails: next-generation biopharmaceuticals with improved potency, Trends Biotechnol., 25(9):390-4 (2007).

(56) References Cited

OTHER PUBLICATIONS

Lonberg, N. et al., Antigen-specific Human Antibodies from Mice Comprising Four Distinct Genetic Modifications, Nature, 368:856-859, (1994).
Lonberg, N., Fully human antibodies from transgenic mouse and phage display platforms, Curr. Opin. Immunol., 20(4):450-9, and supplemental material, 10 pages (2008).
Lonberg, N., Human Monoclonal Antibodies from Transgenic Mice, Therapeutic Antibodies, Handbook of Experimental Pharmacology, Eds. Chernajovsky, Y and Nissim, A., Berlin Heidelberg: Springer-Verlag, 181: 69-97 (2008).
Lovell-Badge (2007) "Many ways to pluripotency," Nature Biotechnology, 25:1114-1116.
Luby, T.M. et al., The mu Switch Region Tandem Repeats Are Important, but Not Required, for Antibody Class Switch Recombination, J. Exp. Med., 193(2):159-168 (2001).
MacDonald et al. (2006) "Velocigene Technology Extended to Humanization of Several Megabases of complex Gene Loci," First International MUGEN Conference of Animal Models for Human Immunological Disease, Sep. 10-13, 2006—Athens, Greece, Abstract 21 and Poster, 2 pages original (pp. 3-11 are p. 2 of the original, enlarged).
MacDonald et al. (2014) "Precise and in situ genetic humanization of 6 Mb of mouse immunoglobulin genes," PNAS, 111(14):5147-5152.
Mageed et al. (2001) "Rearrangement of the human heavy chain variable region gene V3-23 in transgenic mice generates antibodies reactive with a range of antigens on the basis of VhCDR3 and residues intrinsic to the heavy chain variable region," Clin Exp Immunol, 123:1-8.
Mahmoud et al. (2011) "Limiting CDR-H3 Diversity Abrogates the Antibody Response to the Bacterial Polysaccharide α1→3 Dextran," The Journal of Immunology, 187: 879-886.
Mahmoudi et al. "V region gene analysis of human IgM hybridoma monoclonal anti-Sm antibodies," Lupus, 6:578-589, 1997.
Manis et al. (2002) "Mechanism and control of class-switch recombination," Trends in Immunology, 23(1):31-39.
Marasca et al. (2001) "Immunoglobulin Gene Mutations and Frequent Use of VH1-69 and VH4-34 Segments in Hepatitis C VirUS Positive and Hepatitis C VirUS Negative Nodal Marginal Zone B-Cell Lymphoma," American Journal of Pathology, 159(1): 253-261.
Martin and Van Ness, (1989) "Identification of a Germ Line Transcript from the Unrearranged Kappa Gene in Human B Cells," Molecular and Cellular Biology, 9(10):4560-4562.
Martin and Van Ness, (1990) "Initiation and Processing of Two Kappa Immunoglobulin Germ Line Transcripts in Mouse B cells," Molecular and Cellular Biology, 10(5):1950-1958.
Martinez-Jean, C. et al., Nomenclature and overview of the mouse (*Mus musculus* and *Mus* sp.) immunoglobulin kappa (IGK) genes, Exp. Clin. Immunogenet., 18(4):255-79 (2001).
Marvin, J. and Zhu, Z., Recombinant approaches to IgG-like bispecific antibodies, Acta Pharmacologica Sinica, 26(6):649-658 (2005).
Masuda et al. (2006) "The role of interface framework residues in determining antibody $V_H N_L$ interaction strength and antigen-binding affinity," FEBS J., 273:2184-2194.
Matheson et al. (2009) "Light chain-deficient mice produce novel multimeric heavy-chain-only IgA by faulty class switching." Int. Immunol., 21(8):957-966.
Matsuda, F. et al., The Complete Nucleotide Sequence of the Human Immunoglobulin Heavy Chain Variable Region Locus, J. Exp. Med., 188(11): 2151-2162 (1998).
McGoldrick et al. (2013) "Rodent models of amyotrophic lateral sclerosis," Biochimica et Biophysica Acta, 1832:1421-1436.
Mei et al. (1991) "Vasoactive intestinal peptide hydrolysis by antibody light chains," J. Biol. Chem., 266(24):15571-4.
Mendez M.J., et al., Functional transplant of megabase human immunoglobulin loci recapitulates human antibody response in mice, Nat Genet. 15(2):146-56 (1997).

Merchant, A. et al., An efficient route to human bispecific IgG, Nature Biotechnology, 16(7):677-681 (1998).
Miklos et al. (2000) "Salivary gland mucosa-associated lymphoid tissue lymphoma immunoglobulin VH genes show frequent use of V1-69 with distinctive CDR3 features," Blood, 95:3878-3884.
Miller et al. (2003) "Design, Constructio, and In Vitro Analyses of Multivalent Antibodies," J. Immunol., 170:4854-4861.
Mills et al. (1997) "Enhancer complexes located downstream of both human immunoglobulin Calpha genes, Journal of Experimental Medicine,"186(6):845-858.
Mirzabekov et al. (1996) Nucleic Acids Res 24(15): 2998-3004.
Montaño and Morrison, (2002) "Influence of the Isotype of the Light Chain on the Properties of IgG," Journal of Immunology, 168:224-231.
Moran, (2013) "Mouse platforms jostle for slice of humanized antibody market," Nature Biotechnology, 31(4):267-268.
Morrison et al. (1998) "Variable region domain exchange influences the functional properties of igG," J. Immunol., 160:2802-2808.
Mortari et al. (1993) "Human Cord Blood Antibody Repertoire," The Journal of Immunology, 150(4):1348-1357.
Muller et al. (1993) "B-Cell Abnormalities in AIDS: Stable and Clonally-Restricted Antibody Response in HIV-1 Infection," Scand. J. Immunol., 38:327-334.
Muñoz et al. (2008) "Conventional pluripotency markers are unspecific for bovine embryonic-derived cell-lines," Theriogenology, 69(9):1159-1164.
Murphy and Silha (2000) "Unexpected and unexplained phenotypes in transgenic models," Growth Hormone & IGF Research, 10:233-235.
Murphy, A., VelocImmune: Immunoglobulin Variable Region Humanized Mice, Recombinant Antibodies for Immunotherapy, Ed. Little, M., New York, NY: Cambridge University Press, Chapter 8, pp. 100-107 (2009).
Murphy (2012) Kenneth, Janeway's Immunobiology 8th Edition. New York: Garland Science, Printed in USA., Chapter 5, Sections 5-1 to 5-4, pp. 157-162.
Murphy et al. (2014) "Mice with megabase humanization of their immunoglobulin genes generate antibodies as efficiently as normal mice," PNAS, pp. 1-12, www.pnas.org/cgi/doi/10.1073/pnas.1324022111.
Muyldermans, S. et al., Sequence and structure of VH domain from naturally occurring camel heavy chain immunoglobulins lacking light chains, Protein Eng., 7(9):1129-35 (1994).
Muyldermans (2001) "Single domain camel antibodies: current status," Rev. Mol. Biotech., 74:277-302.
Muyldermans (2001) "Recognition of antigens by single-domain antibody fragments: the superflous luxury of paired domains," Trends in Biochem. Sci., 26(4):230-235.
Muyldermans et al. (2003) "Camel antibodies and single-domain antibodies," published online at http://ultr.vub.ac.be/ULTR/camel_antibodies.html, 2 pages.
Myszka (1999) "Improving biosensor analysis," J. Mol. Recogn. 12:279-284.
Nagle (2007) Regeneron helps make Sanofi VelocImmune to its "weak pipeline", <http://www.outsourcing-pharma.com/Preclinical-Research/Regeneron-helps-make-Sanofi-VelocImmune-to-its-weak-pipeline>—Published Dec. 3, 2007.
Nelson, A.L. et al., Development trends for human monoclonal antibody therapeutics, Nat. Rev. Drug. Discov., 9(10):767-74 (2010).
Nemazee, D., Receptor editing in B cells, Adv. Immunol., 74:89-126 (2000).
Nemazee, D., Receptor editing in lymphocyte development and central tolerance, Nat. Rev. Immunol., 6(10):728-40 (2006).
News in Brief Article. Big Pharma views for mice, Nature Biotechnology Jun. 2007;25(6):613.
Nguyen et al. (1999) "Loss of splice consensus signal is responsible for the removal of the entire CH1 domain of the functional camel IgG2A heavy-chain antibodies," Mol. Immunol., 36:515-524.
Nguyen, V.K. et al., Heavy-chain only antibodies derived from dromedary are secreted and displayed by mouse B cells, Immunology, 109(1):93-101 (2003).
Nicholson et al. (1999) "Antibody Repertoires of four-and Five-Feature Translocus Mice Carrying Human Immunoglobulin Heavy

(56) References Cited

OTHER PUBLICATIONS

Chain and kappa and lambda light chain Yeast Artificial Chromosomes," Journal of Immunology, 163(12):6898-6906.
Nieba et al. "Disrupting the hydrophobic patches at the antibody variable/constant domain interface: improved in vivo folding and physical characterization of an engineered scFv fragment," Protein Eng., 10(4):435-444 (1997).
Niemann et al. (2005) "Transgenic farm animals: present and future, Review of Science Technology," 24(1):285-298.
Nishimura et al. (2004) "Possible Function of the ADAM1a/ADAM2 Fertilin Complex in the Appearance of ADAM 3 on the Sperm Surface," The Journal of Biological Chemistry, 279(33):34957-34962.
Nissim et al., Antibody fragments from a 'single pot' phage display library as immunochemical reagents, EMBO J., 13(3): 692-698 (1994).
Nitschke et al. (2001) "Deletion of the DQ52 element with the Ig heavy chain locus leads to a selective reduction in VDJ recombination and altered D gene usage," J. Immunol., 166:2540-52.
Novotny et al. (1985) "Structural Invariants of Antigen Binding: Comparison of Immunoglobulin VL-VH and VL-VL Domain Dimers," Proc. Nat. Acad. Sci., 82:4592-4596.
Oberdoerffer et al. (2003) "Unidirectional Cre-mediated genetic inversion in mice using the mutant loxP pair lox66/lox71," Nucleic Acids Research, 31(22)(e140):1-7.
O'Brien, R. et al., Somatic hypermutation of an immunoglobulin transgene in kappa mice, Nature, 326(6111):405-409 (1987).
Oddo et al. (2003) "Triple-Transgenic Model of Alzheimer's Disease with Plaques and Tangles: Intracellular A and Synaptic Dysfunction," Neuron, 39:409-421.
Omidfar et al. (2004) "Production of a Novel Camel Single-Domain Antibody Specific for the Type III Mutant EGFR," Tumor Biol. 25:296-305.
Omidfar et al. (2004) "Production and Characterization of a New Antibody Specific for the Mutant EGR Receptor, EGFRvIII, in Camelus bactrianus," Tumor Biol., 25:179-187.
Orban, P.C. et al., Tissue- and site-specific DNA recombination in transgenic mice, Proc. Natl. Acad. Sci. U S A., 89(15):6861-5 (1992).
Paris and Stout, (2010) "Equine embryos and embryonic stem cells: defining reliable markers of pluripotency," Theriogenology, 74(4):516-524.
Parng et al. (1996) "Gene conversion contributes to the Ig light chain diversity in cattle," The Journal of Immunology, 157(12):5478-5486.
Pasqualini and Arap (2004) "Hybridoma-free generation of monoclonal antibodies," Proceedings of the National Academy of Sciences USA, 101(1):257-259.
Peeters, K. et al., Production of antibodies and antibody fragments in plants, Vaccine, 19(17-19):2756-61 (2001).
Pelanda, R. et al., A prematurely expressed Ig(kappa) transgene, but not V(kappa)J(kappa) gene segment targeted into the Ig(kappa) locus, can rescue B cell development in lambda5-deficient mice, Immunity, 5(3):229-239 (1996).
Pereira et al. (1998) "Cardiolipin binding a light chain from lupus-prone mice," Biochemistry, 37:1430-7.
Perez et al. (2010) "Primary cutaneous B-cell lymphoma is associated with somatically hypermutated immunoglobulin variable genes and frequent use of VH1-69 and VH4-59 segments," British Journal of Dermatology, 162:611-618.
Petitte et al. (2004) "Avian pluripotent stem cells," Mech. of Develop., 121(9):1159-1168.
Pettersson et al. (1990) "A second B cell-specific enhancer 3' of the immunoglobulin heavy-chain locus," Nature, 344(6262):165-168.
Phan, T. et al., Altered Migration, Recruitment, and Somatic Hypermutation in the Early Response of Marginal Zone B Cells to T Cell-Dependent Antigen, The Journal of Immunology, 174(8):4567-78 (2005).
Phan, T. et al., B Cell Receptor-independent Stimuli Trigger Immunoglobulin (Ig) Class Switch Recombination and Production of IgG Autoantibodies by Anergic Self-Reactive B Cells, The Journal of Experimental Medicine, 197(7):845-860 (2003).
Phan, T.G. et al., High affinity germinal center B cells are actively selected into the plasma cell compartment, J. Exp. Med., 203(11):2419-24 (2006).
Phelps, J. et al., Expression and Characterization of a Chimeric Bifunctional Antibody with Therapeutic Applications, The Journal of Immunology, 145:1200-1204 (1990).
Pollock, D.P. et al., Transgenic milk as a method for the production of recombinant antibodies, J. Immunol. Methods., 231(1-2):147-57 (1999).
Popov et al. (1999) "A Human Immunoglobulin lambda locus is Similarly Well Expressed in Mice and Humans," J. Exp. Med., 189(10):1611-1619.
Porteus, M.H. and Carroll, D., Gene targeting using zinc finger nucleases, Nat.; Biotechnol., 23(8):967-73 (2005).
Pos et al. (2008) "VH1-69 germline encoded antibodies directed towards ADAMTSI3 in patients with acquired thrombotic thrombocytopenic purpura," Journal of Thrombosis & Haemostasis, 7:421-428.
Poueymirou et al (2007) "F0 generation mice fully derived from gene-targeted embryonic stem cells allowing immediate phenotypic analyses," Nat Biotechnol 25, 91-99.
Prak, E. and Weigert, M., Light chain replacement: a new model for antibody gene rearrangement, J. Exp. Med., 182(2):541-548 (1995).
Prelle, K. et al., Pluripotent stem cells—model of embryonic development, tool for gene targeting, and basis of cell therapy, Anat. Histol. Embryol., 31(3):169-86 (2002).
Qi et al. (2005) "A new transgenic rat model of hepatic steatosis and the metabolic syndrome," Hypertension, 45(5):1004-1011.
Radic, M.Z. et al., Ig H and L chain contributions to autoimmune specificities, J. Immunol., 146(1):176-82 (1991).
Ramírez-Solis et al. (1995) "Chromosome engineering in mice," Nature, 378(6558):720-724.
Ramsden et al. (1994) "Conservation of sequence in recombination signal sequence spacers," Nucleic Acids Res., 22(10):1785-1796.
Ravetch et al. (1981) "Structure of the human immunoglobulin mu locus: characterization of embryonic and rearranged J and D genes," Cell, 27:583-591.
Ray (1991) "Ectopic expression of a c-kitW42 minigene in transgenic mice: recapitulation of W phenotypes and evidence for c-kit function in melanoblast progenitors," Genes Dev., 5(12A): 2265-2273.
Reineke (2004) "Antibody Epitope Mapping Using Arrays of Synthetic Peptides," Methods Mol Biol 248:443-463.
Ren e al. (2004) "Silencing of the immunoglobulin heavy chain locus by removal of all eight constant-region genes in a 200-kb region," Genomics, 84:686-695.
Reusch, et al., Beyond mAbs with TandAbs, Innovations in Pharmaceutical Technology, 4 pages (Jun. 2011).
Rich et al. (2000) "Advances in surface plasmon resonance biosensor analysis," Curr. Opin. Biotechnol. 11:54-61.
Rickert, R. et al., Impairment of T-cell-dependent B-cell responses and B-1 cell development in CD19-deficient mice, Nature, 376(6538):352-5 (1995).
Rickert, R.C. et al., B lymphocyte-specific, Cre-mediated mutagenesis in mice, Nucleic Acids Res., 25(6):1317-8 (1997).
Riechmann (1996) "Rearrangement of the Former VL Interface in the Solution Structure of a Camelised, Single Antibody VH Domain," J. Mol. Biol., 259:957-969.
Riechmann, L. and Muyldermans, S., Single domain antibodies: comparison of camel VH and camelised human VH domains, J. Immunol. Methods., 231(1-2):25-38 (1999).
Ristevski (2005) "Making better transgenic models: conditional, temporal, and spatial approaches," Molecular Biotechnology, 29(2):153-163.
Ritchie, K. et al., Allelic exclusion and control of endogenous immunoglobulin gene rearrangement in kappa transgenic mice, Nature, 312:517-520 (1984).
Rocca-Serra et al. (1983) "Two monoclonal antibodies against different antigens using the VH germ-line gene," Nature 304:353-5.
Rodriguez et al. (2000) "High-efficiency deleter mice show that FLPe is an alternative to Cre-loxP," Nature Genetics, 25:139-140.

(56) References Cited

OTHER PUBLICATIONS

Rojas et al. (2002) "Phage antibody fragments library combining a single human light chain variable region with immune mouse heavy chain variable regions," Biotechnol., 94(3):287-298.
Ronai et al. (2003) "Use of a simple, general targeting vector for replacing the DNA of the heavy chain constant region in mouse hybridoma cells," J. Immunol. Methods, 275:191-202.
Rosner, K. et al., Third complementarity-determining region of mutated VH immunoglobulin genes contains shorter V, D, J, P, and N components than non-mutated genes, Immunology, 103(2):179-87 (2001).
Rouet, P., et al. Introduction of double-strand breaks into the genome of mouse cells by expression of a rare-cutting endonuclease, Mol. Cell. Biol., 14:12 8096-8106 (1994).
Rudikoff et al. (1982) "Single amino acid substitution altering antigen-binding specificity," PNAS 79:1979-1983.
Sapparapu et al. (2009) "Antigen-specific proteolysis by hybrid antibodies containing promiscuous proteolytic light chains paired with an antigen-binding heavy chain," J. Biol. Chem., 284(36):24622-24633.
Sasaki et al., "Canonical NF-kB Activity, Dispensable for B Cell Development, Replaces BAFF-Receptor Signals and Promotes B Cell Proliferation upon Activation," Immunity 24: 729-739 (2006).
Sasso et al., (1990) "Prevalence and Polymorphism of Human $V_h3$ Genes," Journal of Immunology, 145(8):2751-2757.
Sasso et al. (1993) "A Fetally Expressed Immunoglobulin $V_H1$ Gene Belongs to a Complex Set of Alleles," Journal of Clinical Investigation, 91:2358-2367.
Sasso et al. (1996) "Expression of the Immunoglobulin VH Gene 51p1 Is Proportional to Its Germline Gene Copy Number" Journal of Clinical Investigation, 97(9):2074-2080.
Schelonka et al. (2005) "A Single $D_H$ Gene Segment Creates Its Own Unique CDR-H3 Repertoire and Is Sufficient for B cell Development and Immune Functions," Journal of Immunology, 175:6624-6632.
Schlissel and Baltimore (1989) "Activation of Immunoglobulin Kappa Gene Rearrangement Correlates with Induction of Germline Kappa Gene Transcription," Cell, 58:1001-1007.
Schnieke, A.E. et al., Human factor IX transgenic sheep produced by transfer of nuclei from transfected fetal fibroblasts, Science, 278(5346):2130-3 (1997).
Schroeder, H.W. Jr., Similarity and divergence in the development and expression; of the mouse and human antibody repertoires, Dev. Comp. Immunol., 30(1-2):119-35 (2006).
Schultz et al. (2012) "Humanized mice for immune system investigation: progress, promise and challenges," Nature Reviews Immunology, 12:786-798.
Schulze et al. (2006) "Derivation, Maintenance, and Characterization of Rat Embryonic Stem Cells in Vitro," Methods in Molecular Biology, 329:45-58.
Scott (2007) "Mice with a human touch," Nature Biotechnology, 25(10):1075-1077.
Seals and Courtneidge (2003) "The ADAMs family of metalloproteases: multidomain; proteins with multiple functions," Genes and Development, 17(1):7-30.
Segal, D. et al., Introduction: bispecific antibodies, Journal of Immunological Methods, 248(1-2):1-6 (2001).
Sekiguchi, et al. Mechanism of V(D)J Recombination, Molecular Biology of B Cells, Eds. Honjo, Alt, and Neuberger, London, UK: Elsevier Academic Press, pp. 61-82 (2004).
Sen and Baltimore (1986) "Multiple nuclear factors interact with the immunoglobulin enhancer sequences," Cell, 46(5):705-716.
Sepulveda et al. (2003) "Binders Based on Dimerised Immunoglobulin VH Domains," J. Mol. Biol., 333:355-365.
Sharpe, M.J. et al., Somatic hypermutation of immunoglobulin kappa may depend on sequences 3' of C kappa and occurs on passenger transgenes, EMBO J., 10(8):2139-45 (1991).
Shi et al. (2006) J. Immunol. Methods 314:9-20.
Schiffer et al. (1973) "Structure of a λ-Type Bence-Jones Protein at 3.5-Å," Biochemistry, 12:4620-4631.

Shih, H.H., Discovery Process for Antibody-Based Therapeutics, Development of Antibody-Based Therapeutics 426, Eds. Tabrizi, M.A. et al., Springer New York, pp. 9-32 (2012).
Shmerling et al. (2005) "Strong and ubiquitous expression of transgenes targeted into the β-actin locus by Cre/lox cassette replacement," Genesis, 42(5):229-235.
Sibilia et al. (1997) "Structural Analysis of Human Antibodies to Proteinase 3 from Patients with Wegener Granulomatosis," Journal of Immunology, 159:712-719.
Sigmund (2000) "Viewpoint: Are Studies in Genetically Altered Mice Out of Control?" Arterioscler. Thomb. Vasc. Biol., 20(6):1425-1429.
Simon and Rajewsky (1990) "Antibody domain mutants demonstrate autonomy of the antigen binding site," EMBO Journal., 9(4):1051-1056.
Sirac, C. et al., Light chain inclusion permits terminal B cell differentiation and does not necessarily result in autoreactivity, Proc. Natl. Acad. Sci, U S A, 103(20):7747-52 (2006), and Supplemental information, 4 pages, retrieved Jul. 7, 2016: <http://www.pnas.org/content/103/20/7747.1ong?tab=ds#F6>.
Sirac, C. et al., Role of the monoclonal kappa chain V domain and reversibility of renal damage in a transgenic model of acquired Fanconi syndrome, Blood, 108(2):536-543 (2006).
Sirac, C. et al., Toward understanding renal Fanconi syndrome: step by step advances through experimental models, Contrib. Nephrol., 169:247-61 (2011).
Smith, (2002) "Gene transfer in higher animals: theoretical considerations and key concepts," Journal of Biotechnology, 99(1):1-22.
Smith, B. et al., The unique and immunoglobulin-like regions of surrogate light chain component lambda5 differentially interrogate immunoglobulin heavy-chain structure, Molecular Immunology, 47:1195-1206 (2010).
Smith, E.J. et al., A novel, native-format bispecific antibody triggering T-cell killing of B-cells is robustly active in mouse tumor models and cynomolgus monkeys, Sci. Rep., 5:17943 (2015).
Solomon et al. (1998) "Light chain-associated amyloid deposits comprised of a novel κ constant domain," PNAS, 95:9547-9551.
http://en.wikipedia.org/wiki/Somatic_hypermutation[May 10, 2016 2:27:30 PM].
Song et al. (2000) "Light chain of natural antibody plays a dominant role in protein antigen binding," Biochem. Biophys. Res. Comm., 268:390-394.
Soriano, P., Generalized lacZ expression with the ROSA26 Cre reporter strain, Nat. Genet., 21(1):70-1 (1999).
Souroujon et al. (1989) "Polymorphisms in Human H Chain V Region Genes From the VHIII Gene Family," Journal of Immunology, 143(2):706-711.
Stamatopoulos et al. (1997) "Follicular lymphoma immunoglobulin κ light chains are affected by the antigen selection process, but to a lesser degree than their partner heavy chains," British J. Haematology, 96:132-146.
Steipe, B., et al. Sequence statistics reliably predict stabilizing mutations in a protein domain, J. Mol. Biol., 240(3):188-92 (1994).
Stevens et al. (2006) "Velocimmune: Humanization of Immunoglobulin Loc Using Velocigene Technology," First International MUGEN Conference of Animal Models for Human Immunological Disease, Sep. 10-13, 2016—Athens, Greece, Abstract 4 and Poster, 2 pages original (pp. 3-11 are p. 2 of the original, enlarged).
Stevens et al., Human Antibody Discovery, VelocImmune—a novel platform, Pharma Focus Asia, Issue 8: 72-74 (2008).
Storb, U. et al., Transgenic Mice with μ and ? Genes Encoding Antiphosphorycholine Antibodies, J. Exp Med, 164:627-41 (1986).
Su, Q. et al., A DNA transposon-based approach to validate oncogenic mutations in the mouse, Proc. Natl. Acad. Sci. USA, 105(50):19904-9 (2008).
Sui et al. (2009) "Structural and functional bases for broad-spectrum neutralization of avian and human influenza A viruses," Nature Structural & Molecular Biology, 16(3):265-273.
Sun et al. (1994) "Antigen recognition by an antibody light chain," J. Biol. Chem., 269(1):734-738.
Suzuki et al. (1995) "Representation of Rearranged $V_H$ Gene Segments in the Human Adult Antibody Repertoire," Journal of Immunology, 154:3902-3911.

(56) References Cited

OTHER PUBLICATIONS

Swarthout et al. (2011) "Zinc Finger Nucleases: A new era for transgeenic animals," Annals of Neurosciences, 18(1):25-28.
Szent-Gyorgy et al. (2013) "Malachite Green Mediates Homodimerization of Antibody $V_L$ Domains to Form a Fluorescent Ternary Complex with Singular Symmetric Interfaces," J. Mol. Biol., 425:4595-4613.
Tada, H. et al., Expression and characterization of a chimeric bispecific antibody against fibrin and against urokinase-type plasminogen activator, Journal of Biotechnology, 33:157-174 (1994).
Taki et al. (1993) "Targeted Insertion of a Variable Region Gene into the Immunoglobuliin Heavy Chain Locus," Science, 262:1268-1271.
Tanha, J. et al., Optimal design features of camelized human single-domain antibody libraries, J. Biol. Chem., 276(27):24774-80 (2001).
Taylor (1992) "A transgenic mouse that expresses a diversity of human sequence heavy and light chain immunoglobulins," Nucl. Acids Res. 20:6287-6295).
Taylor L.D. et al., Human immunoglobulin transgenes undergo rearrangement, somatic mutation and class switching in mice that lack endogenous IgM, Int Immunol. 6(4):579-91 (1994).
Tiegs, S. et al., Receptor Editing in Self-reactive Bone Marrow B Cells,The Journal of Experimental Medicine, 177:1009-1020 (1993).
Timetable for Mouse ES Cells course at Wellcome Trust Sanger Institute Oct. 26, 2009—Nov. 8, 2009 (black and white), 5 pages original (pp. 6-13 are pp. 1-5 of the original, enlarged).
Timetable for Mouse ES Cells course at Wellcome Trust Sanger Institute Oct. 26, 2009-Nov. 8, 2009 (greyscale), 5 pages original (pp. 6-13 are pp. 1-5 of the original, enlarged).
To et al. (2005) "Isolation of Monomeric Human $V_H$S by a Phage Selection," J. Biol. Chem., 280 (50):41395-41403.
Tomer (2000) "Characterization of a discontinuous epitope of the human immunodeficiency virus ¨HIV! core protein p24 by epitope excision and differential chemical modification followed by mass spectrometric peptide mapping analysis," Protein Science: 9:487-496 (first named author is Hochleitner).
Tomizuka, K. et al., Double trans-chromosomic mice: maintenance of two individual human chromosome fragments containing Ig heavy and kappa loci and expression of fully human antibodies, Proc. Natl. Acad. Sci. U S A., 97(2):722-7 (2000).
Tonegawa (1983) "Somatic generation of antibody diversity," Nature, 302(5909):575-581.
Torres and Kuhn (1997) Laboratory Protocols for Conditional Gene Targeting, 37-40.
Tsubata, T. and Reth, M., The Products of the Pre-B Cell-specific Genes(Lambda5 and VpreB) and the Immunoglobulin mu Chain Form a Comples that is Transported onto the Cell Surface, Journal of Experimental Medicine, 172:973-976 (1990).
Tsybovsky et al. (2004) "Folding and stabiilty of chimeric immunofusion VL-barstar," Biochem (Moscow), 69(9):939-948.
Tuaillon (2000) "Repertoire analysis in human immunoglobulin heavy chain minilocus transgenic, [mu]MT/ [mu]MT mice," Molecular Immunology, 37(5):221-231.
Tuaillon et al. (1993) "Human immunoglobulin heavy-chain minilocus recombination in transgenic mice: Gene-segment use in μ, and γ transcripts," PNAS, 90:2734-2743.
UniProt Entry Q5QGZ9, retrieved Jan. 21, 2015 from <http://www.uniprot.org/uniprot/Q5QGZ9> (16 pages).
Van Den Beucken et al. (2001) "Building novel binding ligands to B7.1 and B7.2 based on human antibody single variable light chain domains," J. Mol. Immunol., 310:591-601.
Van Ness et al. (1981) "Transcription of the unrearranged mouse C kappa locus: sequence of the initiation region and comparison of activity with a rearranged V kappa-C kappa gene," Cell, 27:593-602.
Van Spriel, A.B. et al., Immunotherapeutic perspective for bispecific antibodies, Immunol. Today, 21(8):391-7 (2000).
Vasquez, K.M. et al., Manipulating the mammalian genome by homologous recombination, Proc. Natl. Acad. Sci. U S A., 98(15):8403-10 (2001).
Vaughan, T.J. et al., Human antibodies with sub-nanomolar affinities isolated from a large non-immunized phage display library, Nat. Biotechnol., 14(3):309-14 (1996).
Verkoczy et al. (2010) "Autoreactivity in an HIV-1 broadly reactive neutralizing antibody variable region heavy chain induces immunologic tolerance," Proc. Natl. Acad. Sci. U.S.A., 107(1): 181-186.
Verma, R. et al., Antibody engineering: Comparison of bacterial, yeast, insect and mammalian expression systems, Journal of Immunological Methods, 216:165-181 (1998).
Vieira, P. and Rajewsky, K., The half-lives of serum immunoglobulins in adult mice,; Eur. J. Immunol., 18(2):313-6 (1988).
Wagner et al. (1994) "Antibodies generated from human immunoglobulin miniloci in transgenic mice," Nucleic Acids Research, 22(8):1389-1393.
Wagner et al. (1994) "The diversity of antigen-specific monoclonal antibodies form transgenic mice bearing human immunoglobulin gene miniloci," Eur. J. Immunol., 24:2673-2681.
Wallace et al. (2007) "Manipulating the mouse genome to engineer precise functional syntenic replacements with human sequence," Cell, 128(1):197-209.
Wang et al. (2009) "Conserved amino acid networks involved in antibody variable domain interactions," Proteins, 76:99-114.
Wang and Palese (2009) "Universal epitopes of influenza virus hemagglutinins?," Nature Structural & Molecular Biology, 16(3):233-234.
Ward et al. (1989) "Binding activities of a repertoire of single immunoglobulin variable domains secreted from *Escherichia coli*," Nature, 341:544-546.
Warren and Nie (1998) Science 281: 2016-2018.
Waterfield, M.D. et al., Restricted Structural Heterogeneity in Antibodies: Might Different Heavy Chains have a Common Light Chain? Nature New Biology, vol. 240:215-217 (1972).
Watson and Crick (2002) Molekulyarnaya biotekhnologiya. Printsipy i primeneniye, Moscow Mir., 45-47 and English translation.
Whrnery (2001) "Camelid Immunoglobulins and Their Importance for the New-Born—A Review," J. Vet. Med, 48:560-568.
Williams et al. (1996) "Sequence Evolution of the Human Germline V lambda Repertoire," J. Mol. Biol., 264(2):220-232.
Wilmut, I. and Clark, A.J., Basic techniques for transgenesis, J. Reprod. Fertil. Suppl., 43:265-75 (1991).
Wilmut, I. et al., Viable offspring derived from fetal and adult mammalian cells, Nature, 385(6619):810-3 (1997).
Winter, D.B. et al., Insertion of 2 kb of bacteriophage DNA between an immunoglobulin promoter and leader exon stops somatic hypermutation in a kappa transgene, Mol. Immunol., 34(5):359-66 (1997).
Wu, H. et al., Double replacement: strategy for efficient introduction of subtle mutations into the murine Col1a-1 gene by homologous recombination in embryonic stem cells, Proc. Natl. Acad. Sci. U S A., 91(7):2819-23 (1994).
Xu and Davis (2000) "Diversity in the CDR3 Region of VHIs Sufficient for Most Antibody Specificities," Immunity, 13:37-45.
Xu, L. et al., Combinatorial surrobody libraries, Proceedings of the National Academy of Sciences (USA), 105(31):10756-10761 (2008).
Yamada et al. (1991) "Preferential Utilization of Specific Immunoglobulin Heavy Chain Diversity and Joining Segments in Adult Human Peripheral Blood B Lymphocytes," Journal of Experimental Medicine, 173:395-407.
Yang, X.W. et al., Homologous recombination based modification in *Escherichia coli* and germline transmission in transgenic mice of a bacterial artificial chromosome, Nat. Biotechnol. 15(9):859-65 (1997).
Yantha et al. (2010) "Unexpected Acceleration of Type 1 Diabetes by Transgenic Expression of B7-H1 in NOD Mouse Peri-Islet Glia," Diabetes, 59:2588-2596.
Yoshiki and Moriwaki (2006) "Mouse Phenome Research, Implications of Genetic Background," ILAR Journal, 47(2):94-102.
Zemlin, M. et al., Expressed Murine and Human CDR-H3 Intervals of Equal Length Exhibit Distinct Repertoires that Differ in their Amino Acid Composition and Predicted Range of Structures, JMB, 334:733-749 (2003).

(56) References Cited

OTHER PUBLICATIONS

Zheng et al. (2000) "Engineering mouse chromosomes with Cre-loxP: range, efficiency, and somatic applications," Molecular and Cellular Biology, 20(2):648-655.
Zheng, J. et al., Immunoglobulin gene transcripts have distinct VHDJH recombination characteristics in human epithelial cancer cells, J. Biol. Chem., 284(20):13610-9 (2009).
Zou et al. (1994) Cre-loxP-mediated gene replacement: a mouse strain producing humanized antibodies, Current Biology, 4:1099-1103.
Zou et al. (2001) "Truncation of the μ heavy chain alters BCR signalling and allows recruitment of CD5+ B cells," International Immunology, 13(12):1489-1499.
Zou et al. (2005) "Expression of a Dromedary Heavy Chain-Only Antibody and B Cell Development in the Mouse," J. Immunol., 175:3769-3779.
Zou et al. (2008) "Removal of the BiP-retention domain in Cμ permits surface deposition and developmental progression without L-chain," Mol. Immunol., 45:3573-3579.
After Final Consideration Pilot Program Request as filed in U.S. Appl. No. 13/798,310, filed Jul. 18, 2014 (2 pages).
Applicant's Written Submissions for AU2009263082, 49 pages (Sep. 6, 2016).
Brief comments on third party observations, EP 11703799.1-1410, submitted to EPO by David Power, 3 pages (Apr. 20, 2015).
Communication in Cases for which No Other Form is Applicable for PCT/US2012/026416, 9 pages (dated Jun. 7, 2013).
Communication in Cases for Which No Other Form Is Applicable for PCT/US2012/069981, 18 pages (dated Jul. 3, 2013).
Communication pursuant to Article 94(3) EPC for EP 11 703 799.4, 6 pages (dated Oct. 9, 2012).
Communication pursuant to Article 94(3) EPC for EP 12 173 456.0, 5 pages (dated Dec. 5, 2012).
Corrected Claims in JP5749161 (English and Japanese), 6 pages.
Cover Letter—Applicant Post-Hearing Submissions in AU2009263082, 1 page (Oct. 19, 2016).
Declaration Appendix as filed in U.S. Appl. No. 13/798,310 dated Jul. 18, 2014 (7 pages).
Declaration of Andrew M. Scharenberg, M.D., filed in prosecution of U.S. Appl. No. 12/130,818, 21 pages, signed Oct. 4, 2010.
Declaration of Brink dated Apr. 30, 2015, as filed in AU Application No. 2009263082, 34 pages.
Declaration of Brink dated Jun. 2, 2015, as filed in AU Application No. 2009263082, 38 pages.
Declaration of Brink dated Sep. 27, 2016, as filed against EP Patent No. 2,147,594 B1 (European patent application No. 09075279.1), 33 pages.
Declaration of DeFranco dated Dec. 21, 2014, as filed in AU Application No. 2009263082, 56 pages.
Declaration of DeFranco dated Oct. 19, 2015, as filed in AU Application No. 2009263082, 31 pages.
Declaration of Denley dated May 1, 2015, as filed in AU Application No. 2009263082, 493 pages.
Declaration of Dr. Joel Martin, Opposition filed against European Patent No. EP 2314629 B1, 13 pages. (May 18, 2016).
Declaration of Dr. Ton Logtenberg filed in U.S. Appl. No. 13/750,753, 10 pages (Dec. 18, 2015).
Declaration of Dr. Ton Logtenberg filed in U.S. Appl. No. 13/750,753, 4 pages (Sep. 15, 2015).
Declaration of Goodnow dated Oct. 19, 2015, as filed in AU Application No. 2009263082, 81 pages.
Declaration of Hudson dated Jun. 2, 2015, as filed in AU Application No. 2009263082, 81 pages.
Declaration of Hudson dated May 1, 2015, as filed in AU Application No. 2009263082, 52 pages.
Declaration of Lynn E. Macdonald, including Annexes 1-4, as together made publicly available at least upon submission to and online publication by the European Patent Office on Mar. 12, 2015, 13 pages, signed Mar. 3, 2015.
Declaration of Murphy dated Dec. 19, 2014, as filed in AU Application No. 2009263082, 18 pages.
Declaration of Professor Ton Logtenberg for EP2314629, 7 pages (May 4, 2016).
Declaration of Robert Brink in AU 2009263082, 19 pages (Oct. 19, 2016).
Declaration of Tarlinton dated Dec. 21, 2014, as filed in AU Application No. 2009263082, 40 pages.
Declaration of Tarlinton dated Oct. 19, 2015, as filed in AU Application No. 2009263082, 24 pages.
Declaration under 37 CFR 1.131 as filed in U.S. Appl. No. 13/798,310 dated Jul. 18, 2014 (21 Pages).
Declaration Under C.F.R. § 1.131 Inventors: Lynn Macdonald, Cagan Gurer, Karolina Hosiawa, Sean Stevens, and Andrew Murphy dated Dec. 1, 2015.
Declaration Under C.F.R. § 1.132 Dr. Andrew Murphy dated Jul. 16, 2014.
Declaration Under C.F.R. § 1.132 Dr. Jürgen Roes dated Jul. 19, 2014.
EP Examination Report with respect to EP 11741730.3 dated Jan. 23, 2015.
English Translation of Arguments dated Jan. 14, 2014, as filed in Merus Japanese U.S. Pat. No. 5749161, 6 pages.
English Translation of Arguments dated Jan. 5, 2015, as filed in Merus Japanese Patent No. 5749161, 9 pages.
European Search Report with respect to EP12192727, dated Mar. 7, 2013.
European Search Report with respect to EP12195716, dated Jan. 29, 2013.
Exhibit A as filed in U.S. Appl. No. 13/798,310 on Jul. 18, 2014 (2 pages).
Exhibit B as filed in U.S. Appl. No. 13/798,310 on Jul. 18, 2014 (2 pages).
Exhibit C as filed in U.S. Appl. No. 13/798,310 on Jul. 18, 2014 (1 page).
Exhibit D as filed in U.S. Appl. No. 13/798,310 on Jul. 18, 2014 (1 page).
Exhibit E as filed in U.S. Appl. No. 13/798,310 on Jul. 18, 2014 (3 pages).
Extended European Search Report for 12 173 456.0, 9 pages (dated Aug. 21, 2012).
Extended European Search Report for EP 15186515.1, 8 pages (dated Feb. 3, 2016).
Extended European Search Report with respect to EP14154918.8, dated Aug. 27, 2014.
Extended European Search Report with respect to EP14176593.3, dated Nov. 19, 2014.
Extended European Search Report with Respect to EP 15177538.4 dated Oct. 9, 2015.
Extended European Search Report with respect to EP15173007.4, dated Oct. 5, 2015.
Final Office Action with Respect to U.S. Appl. No. 13/756,889, dated Nov. 6, 2015.
Final Office Action with Respect to U.S. Appl. No. 14/267,279, dated Jan. 9, 2017.
Final Office Action with Respect to U.S. Appl. No. 14/674,198, dated Mar. 23, 2017.
Final Office Action with Respect to U.S. Appl. No. 14/674,203, dated Mar. 24, 2017.
Final Office Action with Respect to U.S. Appl. No. 14/674,204, dated Mar. 24, 2017.
Final Office Action with Respect to U.S. Appl. No. 14/674,206, dated Mar. 23, 2017.
Final Office Action with Respect to U.S. Appl. No. 14/674,210, dated Mar. 23, 2017.
Final Office Action with Respect to U.S. Appl. No. 14/674,211, dated Dec. 1, 2016.
Final Post-Hearing Submission—DeFranco Declaration Annexure in AU2009263082, 10 pages (Oct. 18, 2016).
Final Post-Hearing Submission—Opponent in AU2009263082, 4 pages (Oct. 19, 2016).
Final Response to Opposition in EP2501817, 27 pages (Dec. 23, 2016).

(56) References Cited

OTHER PUBLICATIONS

Final Written Submissions for Oral Proceedings Scheduled for Jun. 22, 2016, Opposition to Merus B.V.'s EP 2314629 B1, 13 pages (May 20, 2016).
Final Written Submissions Oral Proceedings Scheduled for Oct. 28, 2016 in EP2147594, 40 pages.
Forrest, K. B., Opinion of the United States District Court, *Regeneron Pharmaceuticals, Inc.* v. *Merus B.V.*, 114 pages (Nov. 2, 2015).
Initial Determination in EP Application No. 10186063.3, 11 pages (Nov. 19, 2015).
Initial Post-Hearing Submissions—DeFranco Declaration Annexure for Australian patent application No. 2009263082, 41 pages (Oct. 4, 2016).
Initial Post-Hearing Submissions—Goodnow Declaration Annexure for Australian patent application No. 2009263082, 13 pages (Oct. 4, 2016).
Initial Post-Hearing Submissions (Applicant) Brink Declaration Annex for Australian patent application No. 2009263082, 36 pages (Oct. 4, 2016).
Initial Post-Hearing Submissions (Applicant) for Australian patent application No. 2009263082, 5 pages (Oct. 5, 2016).
Initial Post-Hearing Submissions (Opponent's Initial Supplementary Submissions) for Australian patent application No. 2009263082, 7 pages (Oct. 5, 2016).
International Search Report for PCT/US2010/059845 and Written Opinion dated Mar. 17, 2011, 10 pages.
International Search Report & Written Opinion with respect to PCT/US2011/041366, dated Sep. 22, 2011.
International Search Report & Written Opinion with respect to PCT/US2011/041370, dated Sep. 22, 2011.
International Search Report & Written Opinion with respect to PCT/US2011/046196, dated Oct. 17, 2011.
International Search Report & Written Opinion with respect to PCT/US2012/026416, dated Jun. 25, 2012.
International Search Report & Written Opinion with respect to PCT/US2012/060487, dated Feb. 1, 2013.
International Search Report & Written Opinion with respect to PCT/US2012/069981, dated Mar. 20, 2013.
International Search Report & Written Opinion with respect to PCT/US2013/024295, dated Apr. 24, 2013.
International Search Report & Written Opinion with respect to PCT/US2015/021884, dated Oct. 13, 2015.
International Search Report and Written Opinion for PCT Application No. PCT/US2013/044257 dated Sep. 4, 2013.
International Search Report for PCT/US2011/023971, 5 pages (dated Apr. 11, 2011).
International Search Report for PCT/US2012/034737 (dated Dec. 6, 2012).
International Search Report for PCT/US2012/049600 (7 pages), dated Nov. 23, 2012.
International Search Report for PCT/US2013/029125 (dated Jun. 20, 2013).
International Search Report for PCT/US2013/044257, 4 pages (dated Sep. 4, 2013).
International Search Report for PCT/US2014/025982 dated Jul. 22, 2014 (6 pages).
International Search Report for PCT/US2014/026040 dated Jul. 29, 2014 (5 pages).
JP Opposition Decision in JP5749161 (English and Japanese), 54 pages (Sep. 7, 2016).
Letter Accompanying Initial Post-Hearing Submissions (Applicant) for Australian patent application No. 2009263082, 1 page (Oct. 5, 2016).
Letter in Reply to Merus Response in EP2147594, 9 pages (Aug. 20, 2015).
Merus Final Written Submissions as filed in EP2147594 / 09075279.1-1405, 32 pages (Aug. 26, 2016).
Merus Response to REGN Opposition in EP2147594, 35 pages (Apr. 2, 2015).
Non-Final Office Action with Respect to U.S. Appl. No. 13/756,889, dated Dec. 1, 2016.
Non-Final Office Action with Respect to U.S. Appl. No. 14/267,279, dated May 24, 2016.
Non-Final Office Action with Respect to U.S. Appl. No. 14/674,198, dated Jul. 7, 2016.
Non-Final Office Action with Respect to U.S. Appl. No. 14/674,203, dated Jul. 6, 2016.
Non-Final Office Action with Respect to U.S. Appl. No. 14/674,204, dated Jul. 6, 2016.
Non-Final Office Action with Respect to U.S. Appl. No. 14/674,206, dated Aug. 4, 2016.
Non-Final Office Action with Respect to U.S. Appl. No. 14/674,210, dated Aug. 31, 2016.
Non-Final Office Action with Respect to U.S. Appl. No. 14/674,211, dated May 9, 2016.
Notice of Opposition for EP 2501817, 28 pages (May 25, 2016).
Notice of Opposition in EP2701499, 27 pages (Nov. 10, 2016).
Notice of Opposition in JP5749161 (English and Japanese), 188 pages (Jan. 15, 2016).
Notice of Opposition to a European patent for EP 2314629, *Merus B.V.* v. *Regeneron Pharmaceuticals, Inc.*, 38 pages (Jul. 15, 2014).
Notice of Reasons for Revocation in JP5749161, (English and Japanese), 18 pages (dated Mar. 17, 2016).
Notice of Receipt of Correction Request in JP5749161 (English and Japanese), 2 pages (dated Jul. 1, 2016).
Nucleotide Sequence RID Y55HBK1 W114, last accessed Aug. 6, 2014 (2 pages).
Office Action for CN Application 201180013714.0, 19 pages (dated May 15, 2013).
Opposition dated Aug. 11, 2014, in EP Application No. 09075279.1, 983 pages.
Opposition dated Aug. 20, 2015, in EP Application No. 09075279.1, 25 pages.
Opposition dated Jan. 15, 2016, in JP U.S. Pat. No. 5749161 and English translation, 188 pages.
Opposition dated Sep. 22, 2014, in AU Application No. 2009263082, 35 pages.
Opposition filed in European Application No. 10186063.3, 1351 pages (Jul. 15, 2014).
Opposition's rebuttal to Proprietor's submissions in Opposition No. 700031/2016 (English and Japanese), 64 pages (Aug. 22, 2016).
Patent Owner Final Submissions in response to the Summons to attend Oral Proceedings dated Nov. 19, 2015 and in preparation of the Hearing of Jun. 22, 2016 for EP2314629, 16 pages (May 20, 2016).
Patentee's Arguments against Opposition No. 700031/2016 (English and Japanese), 29 pages (Jun. 21, 2016).
Patentee's Exhibit 1 submitted with Argument against Opposition No. 700031/2016 on Jun. 21, 2016, "Really Essential Medical Immunology", Blackwell Science Ltd. Cover, colophon, Contents and Chapter 3 (pp. 23-25) (English and Japanese), 17 pages (2000).
Patentee's Exhibit 2 submitted with Argument against Opposition No. 700031/2016 on Jun. 21, 2016, Communication to the EPO submitted by the Opponent in connection with prosecution of EP2505654 (English and Japanese), 7 pages (Sep. 29, 2014).
Patentee's Exhibit 3 submitted with Argument against Opposition No. 700031/2016 on Jun. 21, 2016, Declaration of Peter Hudson (English and Japanese), 15 pages (Jun. 17, 2016).
Preliminary Opinion of the Opposition Division in EP2147594, 11 pages (Jan. 19, 2016).
Reply to Communication in EP12173456.0, 12 pages (dated Apr. 12, 2013).
Reply to Third Party Observations on EP2501817 (May 20, 2013).
Request for Correction in JP5749161 (English and Japanese), 29 pages (Jun. 21, 2016).
Request to provoke an interference U.S. Appl. No. 13/750,753, Jan. 25, 2013.
Response Post-Hearing Submissions by Applicant in AU2009263082, 15 pages (Oct. 19, 2016).
Response to Notice of Opposition dated Aug. 22, 2014 for EP2314629, 20 pages (Feb. 24, 2015).

(56) References Cited

OTHER PUBLICATIONS

Response to Opponent's Submission dated Aug. 26, 2016 and in Preparation of the Hearing scheduled for Oct. 28, 2016 in EP2147594, 14 pages (Sep. 28, 2016).
Statement of Facts and Arguments in Support of Opposition for EP2147594, 57 pages (Aug. 11, 2014).
Summary of Opponent's Submissions for AU2009263082, 35 pages (Aug. 30, 2016).
Summons to Attend Oral Proceedings Arranged in Connection with EP2147594 (Mar. 6, 2013).
Summons to attend oral proceedings dated Jan. 19, 2016, in EP Application 09075279.1, 20 pages.
Summons to Attend Oral Proceedings with respect to EP 11741730.3 mailed Sep. 28, 2015.
Third Party Observation dated Apr. 8, 2014, in CA Application No. 2729095, 16 pages.
Third Party Observation dated Apr. 10, 2015, in EP Application No. 11703799.4, 248 pages.
Third Party Observation dated Apr. 25, 2012, in EP Application No. 09075279.1, 145 pages.
Third Party Observation dated Feb. 28, 2013, in EP Application No. 11703799.4, 43 pages.
Third Party Observation dated Jul. 1, 2013, in EP Application No. 09075279.1, 6 pages.
Third Party Observation dated Jun. 24, 2013, in EP Application No. 09075279.1, 15 pages.
Third Party Observation dated May 16, 2013, in EP Application No. 09075279.1, 82 pages.
Third Party Observation dated May 4, 2015, in EP Application No. 12717033.0, 151 pages.
Third Party Observation dated Nov. 18, 2014, in EP Application No. 11703799.4, 132 pages.
Third Party Observation dated Nov. 3, 2014, in EP Application No. 12173456.0, 274 pages.
Third Party Observation dated Oct. 3, 2013, in EP Application No. 09075279.1, 3 pages.
Third Party Observation dated Oct. 21, 2013, in AU Application No. 2009263082, 24 pages.
Third Party Observation dated Oct. 25, 2012, in EP Application No. 09075279.1, 27 pages.
Third Party Observation dated Sep. 12, 2013, in EP Application No. 09075279.1, 5 pages.
Third Party Observation dated Sep. 16, 2015, in CA Application No. 2729095, 15 pages.
Third Party Observation dated Sep. 5, 2013, in EP Application No. 09075279.1, 11 pages.
Third Party Observation dated Sep. 7, 2015, in EP Application No. 12173456.0, 68 pages.
Third Party Observation pursuant to Article 115 EPC for EP 14170196.1, 6 pages (Jul. 1, 2015).
Third Party Observations on EP2501817 (Feb. 28, 2013).
Third Party Observations pursuant to Art. 115 EPC and R. 114 EPC against EP Application No. 12717033.0, 11 pages (May 4, 2015).
Third Party Observations pursuant to Article 115 EPC and R. 114 EPC against European Application No. 11703799.4, 5 pages (Apr. 10, 2015).
Third Party Observations Under Article 115 EPC against European Application No. 09075279.1 in the name of Merus BV, 12 pages (Oct. 25, 2012).
Third Party Observations under Article 115 EPC for EP 12 173 456.0, 8 pages (Nov. 3, 2014).
Third Party Submission dated Feb. 18, 2013, in U.S. Appl. No. 13/093,156, 179 pages.
Third Party Submission dated Feb. 19, 2014, in U.S. Appl. No. 13/750,753, 282 pages.
Third Party Submission dated Feb. 24, 2014, in U.S. Appl. No. 13/750,753, 97 pages.
Third Party Submission dated Feb. 27, 2014, in U.S. Appl. No. 13/948,818, 10 pages.
Third Party Submission dated Jan. 28, 2013, in U.S. Appl. No. 12/589,181, 13 pages.
Third Party Submission dated Jun. 12, 2013, in U.S. Appl. No. 13/750,753, 100 pages.
Third Party Submission filed in U.S. Appl. No. 13/795,637, 117 pages (Mar. 18, 2014).
U.S. Non-Final Office Action for U.S. Appl. No. 13/022,759 (dated Sep. 7, 2012).
U.S. Non-Final Office Action for U.S. Appl. No. 13/093,156 (dated Sep. 6, 2012).
U.S. Non-Final Office Action for U.S. Appl. No. 13/412,936 (dated Sep. 6, 2012).
Written Opinion for PCT/US2011/023971 (dated Apr. 11, 2011).
Written Opinion for PCT/US2012/034737, (dated Dec. 6, 2012).
Written Opinion for PCT/US2012/049600 (8 pages), dated Nov. 23, 2012.
Written Opinion for PCT/US2013/029125 (dated Jun. 20, 2013).
Written Opinion for PCT/US2013/044257, 5 pages (dated Sep. 4, 2013).
Written Opinion for PCT/US2014/025982 dated Jul. 22, 2014 (7 pages).
Written Opinion for PCT/US2014/026040 dated Jul. 29, 2014 (8 pages).
Statement of Relatedness under MPEP 2001.06 with Respect to U.S. Appl. No. 14/664,765, dated Jun. 15, 2017.
Alexander et al. (1982) "γ heavy chain disease in man: cDNA sequence supports partial gene deletion model," Proc. Natl. Acad. Sci. USA, 79:3260-3264.
Anderson et al. (2007) "New markers for murine memory B cells that define mutated and unmutated subsets," JEM, 204(9):2103-2114.
Austin et al. (2004) "The Knockout Mouse Project," Nature Genetics, 36(9):921-924.
Babcook et al. (1996) "A novel strategy for generating monoclonal antibodies from single, isolated lymphocytes producing antibodies of defined specificites," Proc. Natl. Acad. Sci. USA, 93:7843-7848.
Boder and Wittrup (1997) "Yeast surface display for screening combinatorial polypeptide libraries," Nature Biotechnology, 15:553-557.
Bond et al. (2005) "A Structure-Based Database of Antibody Variable Domain Diversity," J. Mol. Biol. 348:699-709.
Brandt et al. (1984) "Loss of a Consensus Splice Signal in a Mutant Immunoglobulin Gene Eliminates the CH1 Domain Exon from the mRNA," Molecular and Cellular Biology, 4(7):1270-1277.
Brandtzaeg et al. (2004) "Characteristics of Mucosal B Cells with Emphasis on the Human Secretory Immune System," Chapter 15, Molecular Biology of B Cells, 223-246, 13 pages.
Cai and Garen (1996) "A melanoma-specific VH antibody cloned from a fusion phage library of a vaccinated melanoma patient," Proc. Natl. Acad. Sci. USA 93:6280-6285.
Cao, et al. (2009) Isolation and Culture of Primary Bovine Embryonic Stem Cell Colonies by a Novel Method, Journal of Experimental Zoology, 311A:368-376.
Chothia (1985) "Domain Association in Immunoglobulin Molecules the Packing of Variable Domains," J. Mol. Biol., 186:651-663.
Coloma and Morrison (1997) "Design and production of novel tetravalent bispecific antibodies," Nature Biotechnology, 15:159-163.
Conrath et al. (2001) "Camel Single-domain Antibodies a Modular Building Units in Bispecific and Bivalent Antibody Constructs," Journal of Biological Chemistry, 276(10):7346-7350.
Coronella et al. (2000) "Amplification of IgG VH and VL (Fab) from single human plasma cells and B cells," Nucleic Acids Research, 28(20):e85, 7 pages.
Davies and Riechmann (1994) "'Camelising' human antibody fragments: NMR studies on VH domains," FEBS Letters 339:285-290.
Davies and Riechmann (1995) "Antibody VH Domains as Small Recognition Units," Nature Biotechnology, 13:475-479.
Decanniere et al. (1999) "A single-domain antibody fragment in complex with Rnase A: non-canonical loop structions and nonomolar affinity using two CDR loops," Structure, 7(4):361-370.

(56) References Cited

OTHER PUBLICATIONS

Dennis (2002) "Welfare issues of genetically modified animals," ILAR Journal, 43(2):100-109.

Dörner and Radbruch (2007) Antibodies and B Cell Memory in Viral Immunity, Immunity 27:384-392.

Dudgeon et al. (2012) "General strategy for the generation of human antibody variable domains with increased aggregation resistance," PNAS, 10879-10884.

Ehlich et al. (1993) "Immunoglobulin Heavy and Light Chain Genes Rearrange Independently at Early Stages of B Cell Development," Cell, 72:695-704.

Female Science Professor https://science-professor.blogspot.com/2009/04/photoshooters.html; posted Apr. 17, 2009; last accessed May 26, 2017.

Fishwild et al., (1996) "High-avidity human IgGk monoclonal antibodies from a novel train of mililocus transgenic mice," Nat. Biotech., 14(7):845-851.

Galler et al. (2004) "Surface μ Heavy Chain Signals Down-Regulation of the V(D)J-Recombinase Machinery in the Absence of Surrogate Light Chain Components," J. Exp. Med., 199(11):1523-1532.

Green (1999) "Antibody engineering via genetic engineering of the mouse: XenoMouse strains are a vehicle for the facile generation of therapeutic human monoclonal antibodies," J. Immunol. Methods, 231:11-23.

Hasan et al. (2002) "Incomplete block of B cell development and immunoglobulin production in mice carring the μMT mutation on the BALB/c background," Eur. J. Immunol., 32:3463-3471.

Hoogenboom (2005) "Selecting and screening recombinant antibody libraries," Nature Biotechnology, 23(9):1105-1116.

Houdebine et al. "Methods to Generate Transgenic Animals," Genetic Engineering in Livestock, New Applications and Interdisciplinary Perspectives, Engelhard M, et al., 2009, XVI, 146, pp. 31-47.

Huang et al. (1994) "Comparison of Crystal Structures of Two Homologous Proteins: Structural Origin of Altered Domain Interactions in Immunoglobulin Light-Chain Dimers," Biochemistry, 33:14848-14857.

Janeway et al. (1999) "The Development of B Lymphocytes," Chapter 6, Immuno Biology the Immune System in Health and Disease, Fourth Edition, Current Biology Publications, USA, 34 pages.

Janeway and Travers (2008) Immunobiology: The Immune System in Health and Disease, 1st Edition, Current Biology, pp. 8:10-8:19.

Jensen, et al. (2007) One Step Generation of Fully Chimeric Antibodies Using Cγ1-and Cκ Mutant Mice, J. Immunother., 30(3):338-349.

Kitamura and Rajewsky (1992) "Targeted disruption μ chain membrane exon causes loss of heavy-chain allelic exclusion," Nature, 356:154-156.

Kodituwakku et al. (2003) "Isolation of antigen-specific B cells," Immunology and Cell Biology, 81:163-170.

Korhonen, J.M, https://jmkorhonen.net/2012/06/25/is-it-ok-to-record-conferencepresentations-reconsidering-fair-use-and-electronic-note-taking; posted Jun. 25, 2012; last accessed May 26, 2017.

Lanzavecchia et al. (2007) "Human monoclonal antibodies by immortalization of memory B cells," Current Opinion in Biotechnology, 18:523-528.

Liao et al., (2009) "High-throughput isolation of immunoglobulin genes from single human B cells and expression as monoclonal antibodies," Journal of Virological Methods, 158:171-179.

Lonberg (2005) "Human antibodies from transgenic animals," Nature Biotechnology, 23(9):1117-1125.

Longo et al., (2008) "Characterization of immunoglobulin gene somatic hypermutation in the absence of activation-induced cytidine deaminase," J. Immunol., 181(2):1299-1306.

MacPherson and Lamarre (2002) "BLySsful Interactions between DCs and B cells," Nature Immunology, 3(9):798-800.

Manz et al., (2005) "Maintenance of Serum Antibody Levels," Annu. Rev. Immunol., 23:367-386.

McHeyzer-Williams and Ahmed (1999) "B cell memory and the long-lived plasma cell," Current Opinion in Immunology, 11:172-179.

Melton (2002) Chapter 8: Gene-Targeting Strategies, Methods in Molecular Biology, Transgenesis Techniques, 2nd Edition, Priciples and Protocols, 180:19 pages.

Minges Wols (2005) "Plasma Cells," Wiley Online Library, pp. 1-8, doi:10.1038/npg.els.0004030.

Molecular Biology of B Cells, 1st Edition, Academic Press, Feb. 18, 2003, Edited by Tasuku Honjo, Michael Reth, Andreas Radbruch, Frederick Alt, Tasuku Honjo, Michael Neuberger, United States of America, ISBN: 978-0-12-053641-2.

Murphy et al. (2008) Janeway's Immunobiology 7th Edition. New York: Garland Science, Printed in USA., Chapters 9 and 10, pp. 386-446.

Murphy Slide Deck, Slide Presentation dated Nov. 3, 2009, "BAC-based Modifications of the Mouse Genome: The Big and the Backward," slides 1-57.

Muyldermans and Lauwereys (1999) "Unique single-domain antigen binding fragments derived from naturally occurring camel heavy-chain antibodies," Journal of Molecular Recognition, 12:131-140.

Nitschke and Fearon (2004) "Regulation of Antigen Receptor Signaling by the Co-Receptors, CD19 and CD22," Chapter 12, Molecular Biology of B Cells, 171-186, 9 pages.

Orinska et al. (2002) "Novel B cell population producing functional IgG in the absence of membrane IgM expression," Eur. J. Immunol., 32:3472-3480.

Padlan et al. (1986) "Antibody Fab Assembly: the Interface Residues Between CH1 and CL," Molecular Immunology, 23(9):951-960.

Paul (2008) Fundamental Immunology, 6th ed., Lippincott Williams &Wilkins, a Wolters Kluwer business, Philadelphia PA USA, 12 pages.

Radbruch et al. (2006) "Competence and competition: the challenge of becoming a long-lived plasma cell," Immunology, 6:741-750.

Reiter et al. (1999) "An Antibody Single-domain Phage Display Library of a Native Heavy Chain Variable Region: Isolation of Functional Single-domain VH Molecules with a Unique Interface," J. Mol. Biol., 290:685-698.

Roebroek et al. (2003) "Chapter 10: Knockin Approaches," Methods in Molecular Biology, Transgenic Mouse Methods and Protocols, 209:16 pages.

Rouet et al. (2015) "Fully Human VH Single Domains That Rival the Stability and Cleft Recognition of Camelid Antibodies," Jornal of Biological Chemistry, 290(19):11905-11917.

Sanderson et al. (1989) "B lymphocytes express and lose syndecan at specific stages of differentiation," Cell Regulation, 1:27-35.

Scheid et al. (2009) "Broad diversity of neutralizing antibodies isolated from memory B cells in HIV-infected individuals," Nature, 458:636-640.

Schwartz and Cantor (1984) "Separation of Yeast Chromosome-Sized DNAs by Pulsed Field Gradient Gel Electrophoresis," Cell, 37:67-75.

Science Magazine Careers http://www.sciencemag.org/careers/2007/03/mastering-your-phdmaking-most-conference, last accessed Nov. 15, 2016.

Slifka et al., (1998) "Humoral Immunity Due to Long-Lived Plasma Cells," Immunity, 8:363-372.

Sorrell and Kolb (2004) "Chapter XI: Targeted Modification of Mammalian Genomes," Focus on Genome Research, 33 pages.

Steinitz and Klein (1997) "EB virus-induced B lymphocyte cell lines producing specific antibody," Nature, 269:420-422.

Tanaka et al. (2003) "Single Domain Intracellular Antibodies: A Minimal Fragment for Direct in Vivo Selection of Antigen-specific Intrabodies," J. Mol. Biol., 331:1109-1120.

Tangye and Tarlinton (2009) "Memory B cells: Effectors of long-lived immune responses," Eur. J. Immunol., 39:2065-2075.

Tarte et al., (2003) "Gene expression profiling of plasma cells and plasmablasts: toward a better understanding of the late stages of B-cell differentiation," Blood, 102(2):592-600.

V-BASE Sequence Directory http://www2.mrc-lmb-cam.ac.uk/vbase/list2.php.

(56) References Cited

OTHER PUBLICATIONS

Vu et al. (1997) "Comparison of llama VH sequences from conventional and heavy chain antibodies," Molecular Immunology, 34(16-17):1121-1131.
Wrammert et al., (2008) "Rapid cloning of high-affinity human monoclonal antibodies against influenza virus," Nature, 667:672, doi:10.1038/nature06890.
Wu et al. (1993) "Length Distribution of CDRH3 in Antibodies," Proteins: Structure, Function, and Genetics, 16:1-7.
Yarilin A.A. "Osnovy immunologii", M.: Meditsina, 1999, p. 172-174 (with English translation).
Yefenof et al., (1985) "Preparation and analysis of antigen-specific memory B cells," Journal of Immunology, 135:3777-3784.
Yu et al. (2008) "Interaction between Bevacizumab and Murine VEGF-A: A Reassessment," Investigative Ophthalmology & Visual Science, 49(2):522-527.
Zhang et al. (1998) "A new logic for DNA engineering using recombination in *Escherichia coli*," Nature Genetics, 20:123-138.
Zhou et al., (2009) "Developing tTA transgenic rats for inducible and reversible gene expression," International Journal of Biological Sciences, 5:171-181.
Declaration of Kerry Chester dated Oct. 16, 2016, 14 pages.
Declaration of Mike Clark dated May 20, 2015, 30 pages.
Declaration of Anne Corcoran dated May 15, 2017, 13 pages.
Declaration of Daniel Corcos dated May 20, 2015, 18 pages.
Declaration of Peter Delves dated Oct. 18, 2016, 29 pages.
Declaration of Lutz Riechmann dated May 20, 2015, 40 pages.
EP1176383 Exhibit illustrating relevant stages in development with reference to documents cited in the opposition, 1 page.
EP1176383 Notice of Opposition to a European Patent May 19, 2015 by Regeneron Pharmaceuticals, Inc., 28 pages.
EP1176383 Notice of Opposition to a European Patent May 20, 2015 by Crescendo Biologics Limited, 56 pages.
EP1176383 Notice of Opposition to a European Patent May 20, 2015 by Ablynx, 24 pages.
EP1176383 Reply of Patent Proprietor to Notice of Opposition Nov. 3, 2015, 18 pages.
EP1176383 Annex to EPO Communication Opposition Jan. 5, 2016, 12 pages.
EP1176383 Letter Accompanying Submission in Opposition Proceedings by Proprietor Oct. 17, 2016, 4 pages.
EP1176383 Grounds for Decision Annex Opposition Dec. 22, 2016, 21 pages.
EP1176383 Statement of Grounds of Appeal on Behalf of Regeneron Apr. 28, 2017, 36 pages.
EP1176383 Annex to EPO Communication Opposition Dec. 22, 2016, 9 pages.
EP1864998 Notice of Opposition to a European Patent Jun. 23, 2014 by Regeneron Pharmaceuticals, Inc., 27 pages.
EP1864998 Reply of Patent Proprietor to Notice of Opposition Dec. 9, 2014, 18 pages.
EP1864998 Annex to EPO Communication Opposition Aug. 11, 2015, 3 pages.
EP1864998 Annex to EPO Communication Opposition Nov. 16, 2015, 3 pages.
EP1864998 Annex to EPO Communication Opposition Jun. 27, 2016, 3 pages.
EP1864998 Final Written Submissions Nov. 10, 2016, 14 pages.
EP1864998 Letter Regarding Opposition Proceedings by Proprietor Nov. 11, 2016, 2 pages.
EP1864998 Letter Regarding Opposition Proceedings by Proprietor Nov. 30, 2016, 2 pages.
EP1864998 Annex to EPO Communication Oral Proceedings Mar. 13, 2017, 6 pages.
EP1864998 Grounds for Decision Annex Opposition Mar. 13, 2017, 12 pages.
EP1864998 Interlocutory Decision in Opposition Proceedings Mar. 13, 2017, 2 pages.
EP1864998 EPO Communication Commencement of Proceedings Before the Board of Appeal May 30, 2017, 5 pages.
EP2411408 Notice of Opposition to a European Patent Aug. 25, 2016 by Ablynx, 25 pages.
EP2411408 Notice of Opposition to a European Patent Aug. 24, 2016 by Dr. Bernhard, 36 pages.
EP2411408 Notice of Opposition to a European Patent Aug. 23, 2016 by Regeneron, 37 pages.
EP2411408 Reply of Patent Proprietor to Notice of Opposition Feb. 17, 2017, 17 pages.
EP2411408 Submission in Opposition Proceedings Reply from Opponent Jun. 27, 2017, 5 pages.
Non-Final Office Action with Respect to U.S. Appl. No. 14/674,211, dated Jan. 18, 2018.
Statement of Relatedness under MPEP 2001.06 with Respect to U.S. Appl. No. 14/664,765, dated Feb. 11, 2019.
Almagro and Fransson (2008) "Humanization of antibodies," Frontiers in Bioscience, 13:1619-1633.
Bispecific monoclonal antibody, From Wikipedia, the free encyclopedia, pp. 1-5; downloaded on Mar. 19, 2019, https://en.wikipedia.org/wiki/Bispecific monoclonal antibody.
Giraldo and Montoliu (2001) "Size matters: use of YACs, BACs and PACs in transgenic animals," Transgenic Research, 18:83-103.
Goldman et al. (2004) "Transgenic animals in medicine: Integration and expression of foreign genes, theoretical and applied aspects," Med. Sci. Monit., 10(11):RA274-285.
Roussel et al. (1999) "The structure of an entire noncovalent immunoblobulin kappa light-chain dimer (Bence-Jones protein) reveals a weak and unusual constant domains association," Eur. J. Biochem., 260:192-199.
Tian et al. (2016) "Induction of HIV Neutralizing Antibody Lineages in Mice with Diverse Precursor Repertoires," Cell, 166:1471-1484.
Vettermann and Schlissel (2010) "Allelic eclusion of immunoglobulin genes: models and mechanisms," Immunological Reviews, 237:22-42.
Statement of Relatedness under MPEP 2001.06 with Respect to U.S. Appl. No. 14/664,765, dated Sep. 9, 2019.
Wang, X. et al., Ab-origin: an enhanced tool to identify the sourcing gene segments in germline for rearranged antibodies. BMC Bioinformatics, 9(Suppl 12), 9 pages (2008).
Declaration of Professor Dr. Roland Kontermann, Ph.D. For EP2505654 B1, 4 pages (May 19, 2017).
Declaration of Professor Michel Cogné, 26 pages (Jul. 17, 2017).
Notice of Opposition in EP2505654, 39 pages (May 24, 2017).
Opponent Reply to Patentee Submissions in EP2501817, 5 pages (Mar. 17, 2017).
Patent Oppositions—Decision in for AU2009263082, 53 pages (May 5, 2017).
Response to Opposition in EP2701499, 22 pages (Apr. 28, 2017).
Statement of Grounds of Appeal for Patent No. 2147594, 82 pages (2017).
Summons to Opposition in EP2501817, 12 pages (May 17, 2017).
Statement of Relatedness under MPEP 2001.06 with Respect to U.S. Appl. No. 14/664,765, dated May 21, 2020.

* cited by examiner

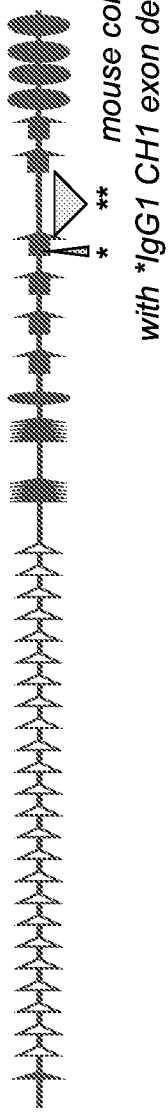
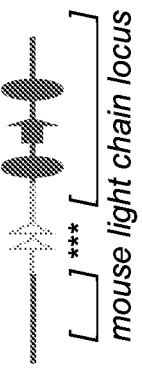
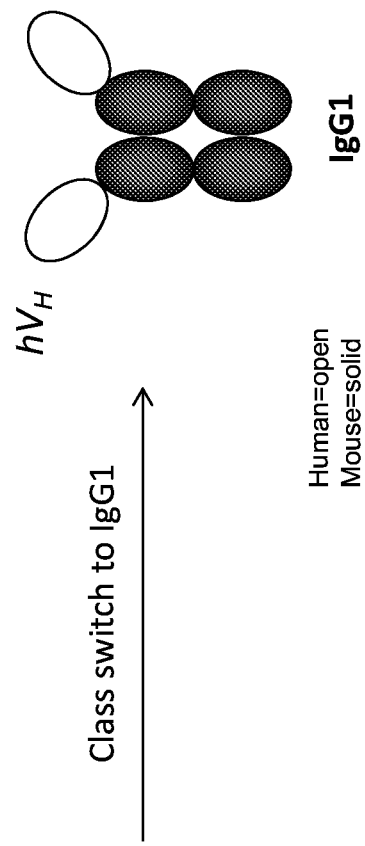
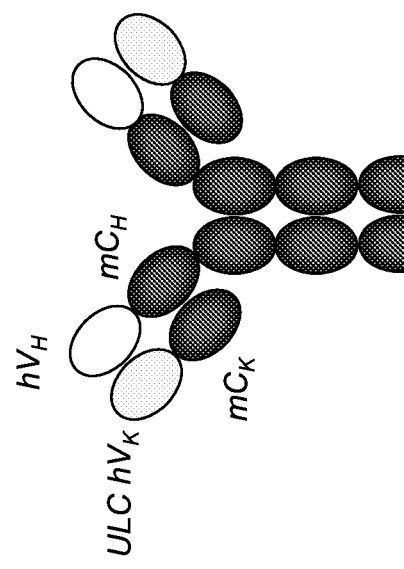
FIG. 1A
FIG. 1B
FIG. 1C

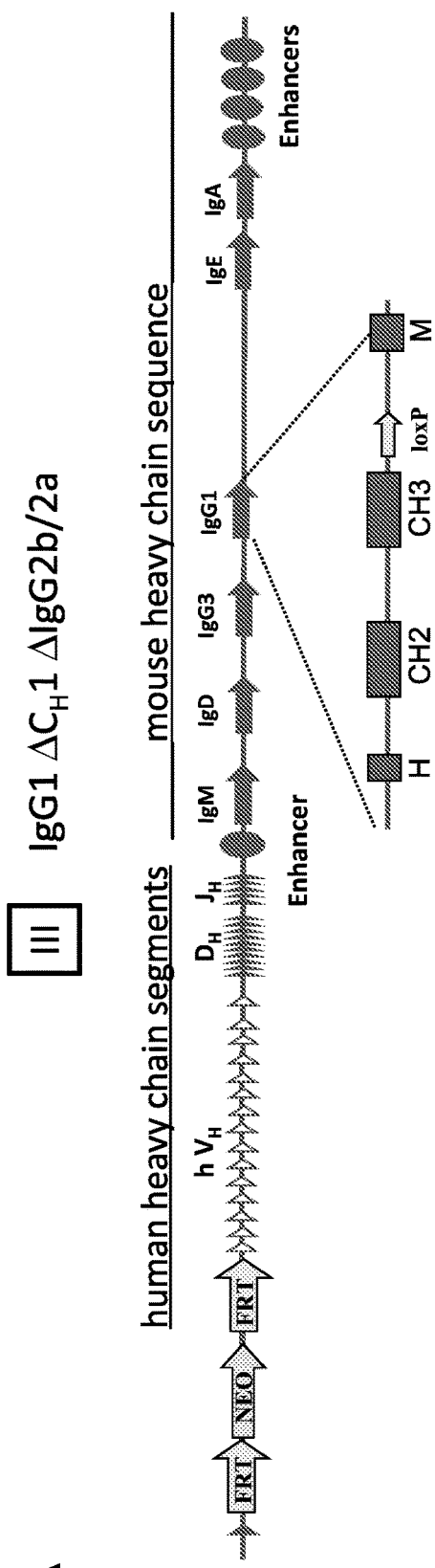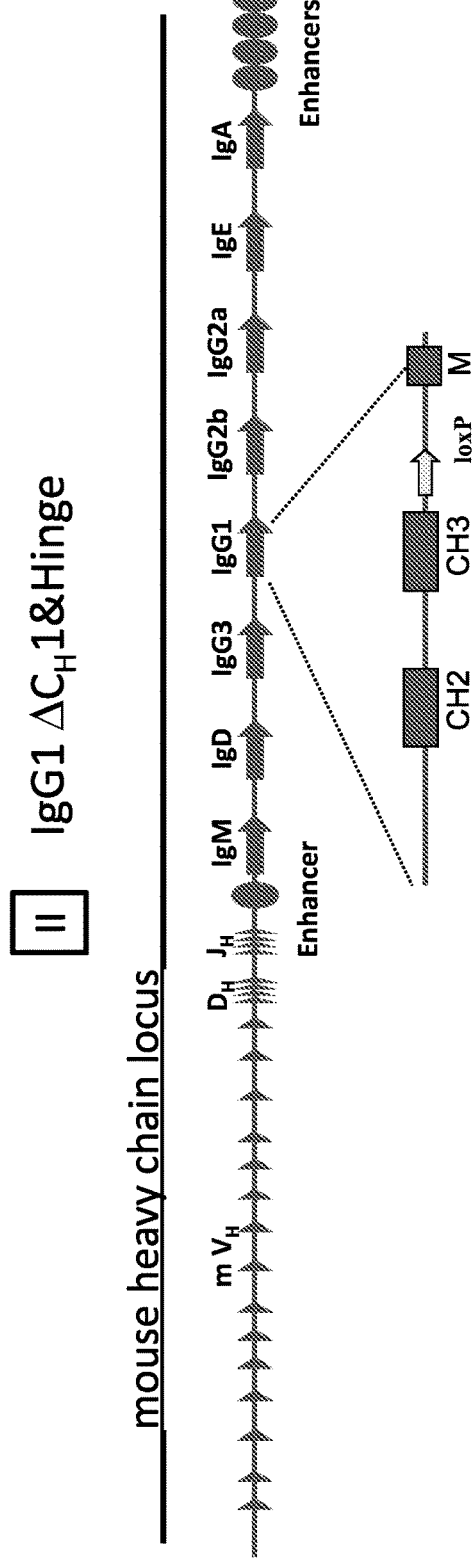
FIG. 4A
FIG. 4B

Two 1859×1633 (IgG1 ΔC$_H$1 &Hinge ΔIgG2b/2a × ULC) HO mice and three 1673×1635 (IgG1 ΔC$_H$1 ΔIgG2b/2a × ULC) HO mice were used

NON-HUMAN ANIMALS THAT MAKE SINGLE DOMAIN BINDING PROTEINS

CROSS-REFERENCE TO RELATED APPLICATIONS

This application claims the benefit under 35 U.S.C. § 119(e) of U.S. Provisional Application Ser. No. 61/968,986, filed 21 Mar. 2014, and U.S. Provisional Application Ser. No. 61/968,905, filed 21 Mar. 2014, both of which applications are hereby incorporated by reference.

FIELD OF INVENTION

Non-human animals are provided that exhibit high diversity in the immunoglobulin heavy chain locus, and preferably very low diversity in the immunoglobulin light chain locus, which allows for selection of single domain antigen binding proteins, including $V_H$-single domain binding proteins and $V_L$ single domain binding proteins, that bind antigen.

BACKGROUND

In most animals, normal immunoglobulin heavy chains are only well-expressed when coupled with their cognate light chains. In humans, lone heavy chains are found in heavy chain disease that is manifested by dysfunctional heavy chains that lack sequences of the variable heavy, the $C_H1$, or the variable heavy and $C_H1$ domains. Heavy chains devoid of light chains are encountered in certain species of fish and in camels. Such heavy chains lack a functional $C_H1$ domain and have non-human features in their heavy chain variable domains. Attempts have been made to make camelized antibodies by modifying mice to express camelized genes that mimic $V_{HH}$ domains found in camels or certain species of fish, in part by removal of IgM and IgG $C_H1$ domains and conforming the heavy chain variable regions to resemble those of camels and/or certain species of fish. Unfortunately, camelized antibodies would be expected to induce immune responses in non-camelid animals. Another challenge with previous versions of non-human animals genetically modified to comprise an inactivated $C_H1$ domain is the reduced expression levels of antigen-specific single domain antigen binding proteins, compared to traditional antibodies. Such reduction may be due to a lack of mechanisms available to non-camelid heavy chain variable regions that allow the heavy chain variable regions to compensate for the absence of a $V_L$ domain. For example, camelid $V_{HH}$ domains found in heavy chain-only binding proteins comprise a CDRH3 that is, on average, longer than those found in non-camelid antibodies, considered to be a major influence on overall antigen affinity and specificity, and thought to compensate for the absence of a $V_L$ domain in the camelid heavy chain-only antibody.

Thus there is a need in the art for genetically modified non-human animals that make diverse single domain binding proteins that have non-camelid $V_H$ domains.

SUMMARY

As disclosed herein, immunoglobulin polypeptide chains comprising a light chain variable region and a heavy chain constant region may be expressed by non-human animals and form $V_L$-single domain antigen binding proteins, e.g., single domain antigen binding proteins comprising light chain variable domains operably linked to heavy chain constant domains, wherein the heavy chain constant domain(s) lack a functional $C_H1$ domain, e.g., of an immunoglobulin heavy chain constant region selected from IgG, IgA, IgE, IgD, or a combination thereof. The $V_L$-single domain antigen binding proteins may exhibit increased stability compared to $V_H$-single domain antigen binding proteins comprising heavy chain variable domains operably linked to heavy chain constant domains lacking a functional $C_H1$ domain. Accordingly, provided herein are non-human animals capable of expressing a $V_L$-single domain antigen binding protein comprising a light chain variable domain and a heavy chain constant region, wherein the heavy chain constant region lacks a functional $C_H1$ domain, and may also optionally lack a functional hinge region and methods of making and using non-human animals expressing $V_L$-single domain antigen binding proteins. Also provided are cells, proteins and nucleic acids derived from non-human animals expressing $V_L$-single domain antigen binding proteins, and use of the isolated cells, proteins and nucleic acids.

Also disclosed herein, the expression of a single rearranged light chain by non-human animals capable of producing single domain antigen binding proteins, e.g., $V_L$- or $V_H$-single domain antigen binding proteins, increases the titer of antigen specific single domain antigen binding proteins in response to antigen challenge compared to a similar non-human animal capable of producing single domain antigen binding proteins that do not express the single rearranged light chain. FIG. 5. This data suggests that the presence of the single rearranged light chain by non-human animals increases the likelihood of generating an antigen-specific single domain antigen binding protein. Accordingly, provided herein are non-human animals capable of expressing single domain antigen binding proteins (e.g., $V_H$- and/or $V_L$-single domain antigen binding proteins) and a single rearranged light chain and methods of making and using non-human animals expressing $V_L$-single domain antigen binding proteins. Also provided are cells, proteins and nucleic acids derived from non-human animals expressing single domain antigen binding proteins and a single rearranged light chain, and use of the isolated cells, proteins and nucleic acids.

Also provided herein are non-human animals comprising $V_L$-single domain antigen binding proteins and a single rearranged light chain, methods of making non-human animals capable of producing a high titer of single domain antigen binding proteins and/or increasing the production of single domain binding proteins by non-human animals capable of producing such binding proteins, methods of using the non-human animals to make antigen-specific single domain antigen binding proteins, and single domain antigen binding proteins so made.

Genetically modified cells, non-human embryos, non-human animals and methods and compositions for making and using them are provided, wherein the animals are genetically modified to produce single domain antigen binding proteins, e.g., binding proteins comprising a heavy chain constant region that lacks a functional $C_H1$ sequence, and also optionally lack a functional hinge region sequence, and wherein the animals are further genetically modified to express the single domain antigen binding protein as a $V_L$-single domain antigen binding protein (e.g., encoded from a rearranged light chain variable region nucleotide sequence operably linked to a heavy chain constant region nucleic acid sequence modified to inactivate or delete a $C_H1$ domain encoding sequence) and/or a single rearranged light chain (e.g., encoded from a single rearranged $V_L:J_L$ sequence operably linked to a light chain constant region in the animal's germline).

The animals as disclosed herein may produce single domain binding proteins, which, in one aspect, comprise an IgG isotype, such as, e.g., the IgG1 isotype. In some embodiments, the single domain antigen binding protein is a $V_H$-single domain antigen binding protein, e.g., comprises a heavy chain variable region operably linked to a heavy chain constant region lacking a functional $C_H1$. In other embodiments, the single domain antigen binding protein is a $V_L$-single domain antigen binding protein, e.g., comprises a light chain variable domain operably linked to a heavy chain constant region lacking a functional $C_H1$, e.g., a heavy chain constant region comprising hinge, $C_H2$, $C_H3$, $C_H4$, or a combination thereof.

Accordingly, in some aspects, a single domain antigen binding protein as described herein is encoded by a nucleic acid sequence derived from one or more unrearranged immunoglobulin light chain V segments and one or more unrearranged immunoglobulin light chain J segments operably linked to a heavy chain constant region (e.g., a heavy chain constant region domain selected from the group consisting of $C_H1$, hinge, $C_H2$, $C_H3$, $C_H4$, and combination thereof), wherein the heavy chain constant region comprises a deletion or an inactivating mutation in a $C_H1$ region sequence. In one embodiment, the unrearranged light chain V and J segments replace one or more, substantially all, or all functional endogenous non-human immunoglobulin heavy chain variable region gene segments at the endogenous non-human immunoglobulin heavy chain locus. In some embodiments, a heavy chain locus modified to comprise light chain variable region gene segments operably linked to a heavy chain constant region comprising a deletion or inactivating mutation in a $C_H1$ region sequence as disclosed herein may be found in the in the germline of the non-human animal. Such a modified locus can be at the endogenous heavy chain locus, or present in a transgene at a locus other than the endogenous heavy chain locus (e.g., inserted at a random position in the genome).

In one aspect, animals disclosed herein comprising a nucleic acid sequence encoding a $V_L$-single domain antigen binding protein (e.g., a nucleic acid sequence derived from one or more unrearranged immunoglobulin light chain V segments and one or more unrearranged immunoglobulin light chain J segments operably linked to a heavy chain constant region comprising a deletion or an inactivating mutation in a $C_H1$ region sequence) may further comprise a second immunoglobulin polypeptide chain comprising a light chain variable region and a light chain constant region, which may be encoded by a second nucleic acid sequence comprising a human light chain V segment and a human light chain J segment operably linked to a light chain constant region. Such second nucleic acid sequence may also be found in the germline of the non-human animal. Such a nucleic acid sequence can be present at the endogenous light chain locus, or present in a transgene at a locus other than the endogenous light chain locus (e.g., inserted at a random position in the genome).

In another aspect, animals modified to comprise a nucleic acid sequence derived from one or more unrearranged immunoglobulin light chain V segments and one or more unrearranged immunoglobulin light chain J segments operably linked to a heavy chain constant region comprising a deletion or an inactivating mutation in a $C_H1$ region sequence may be further modified to express a single rearranged light chain, e.g., a common light chain (ULC).

In some embodiments, the single domain antigen binding protein such as, but not limited to, a $V_L$-single domain antigen binding protein, and/or single rearranged light chain comprises human idiotypes. For example, a single domain antigen binding protein and/or a genetically engineered single rearranged light chain as disclosed herein may comprise a human variable domain and, in one embodiment, a non-human constant domain. In one embodiment, the non-human constant domain is an endogenous non-human constant domain. In one embodiment, the non-human constant domain is a rodent constant domain, e.g., a murine constant domain, e.g., a mouse constant domain. In another embodiment, the constant domain is a human constant domain. In one aspect, the single domain antigen binding protein is a $V_L$-single domain antigen binding protein comprising a human light chain variable domain and a non-human heavy chain constant domain. In one embodiment, the unrearranged light chain V and/or J segments encoding a $V_L$-single domain antigen binding protein as disclosed herein are human segments.

Animals genetically modified to produce the single domain antigen binding proteins as disclosed herein may comprise a heavy chain locus having a replacement of one or more, or all, endogenous immunoglobulin heavy chain variable region gene segments with one or more unrearranged human immunoglobulin heavy chain variable region gene segments, or one or more unrearranged human immunoglobulin light chain V segments and one or more unrearranged human immunoglobulin light chain J segments. In some aspects, all endogenous $V_H$, $D_H$, and $J_H$ gene segments are replaced with one or more unrearranged human $V_H$, one or more unrearranged human $D_H$, and one or more unrearranged human $J_H$ gene segments. In other aspects, all endogenous $V_H$, $D_H$, and $J_H$ gene segments are replaced with one or more unrearranged human immunoglobulin light chain $V_L$ gene segments and one or more unrearranged human immunoglobulin light chain $J_L$ gene segments, e.g., human kappa (κ) Vκ and/and Jκ gene segments and/or human lambda (λ) Vλ and/and Jλ gene segments.

Animals genetically modified to produce the single domain binding protein that comprises a heavy chain variable region or a light chain variable region in the context of a heavy chain constant region comprising a deletion of a $C_H1$ region and/or hinge region may bear the modification (and/or other modifications of a constant gene locus described herein) at an endogenous heavy chain locus, or may bear the modification on a transgene, wherein the transgene is positioned anywhere in the genome, e.g., introduced into the genome by random insertion. In some embodiments, the modified heavy chain locus as described herein may be found in the germline of the animal. In animals also modified to express a single rearranged light chain, the single rearranged light chain variable region can be operably linked to a light chain constant region at the endogenous light chain locus, or can be present in a transgene comprising the single rearranged light chain variable region operably linked with a syngeneic (e.g., autologous; with respect to the non-human animal) or heterologous light chain constant region and present at a locus other than the endogenous light chain locus, e.g., randomly inserted into the genome.

In further embodiments, the heavy chain loci of the animals disclosed herein may comprise a deletion or inactivating mutation in the hinge region(s).

Further, animals disclosed herein may be modified to comprise and/or express a single rearranged light chain variable gene sequence operably linked to a light chain constant region, also referred to as common or universal light chain (ULC), which may be encoded by a light chain locus comprising a single rearranged $V_L$:$J_L$ gene sequence. In some embodiments, the light chain locus comprises a single rearranged $V_L$:$J_L$ gene sequence in which the $V_L$ sequence is a Vκ sequence. In some aspects, the Vκ sequence is selected from Vκ1-39 or Vκ3-20. In some aspects, the $J_L$ sequence is a vκ gene sequence, e.g., a Jκ1 sequence, a Jκ2 sequence, a Jκ3 sequence, a Jκ4 sequence, or a Jκ5 sequence, etc. In some embodiments, the light chain locus comprises a single rearranged Vκ:Jκ sequence selected from the group consisting of Vκ1-39Jκ5 and Vκ3-20Jκ1. In one embodiment, the light chain locus comprises a single rearranged Vκ:Jκ sequence of Vκ1-39Jκ5. In another embodiment, the light chain locus comprises a single rearranged Vκ:Jκ sequence of Vκ3-20Jκ1. In some embodiments, the single rearranged variable gene sequence is operably linked to a non-human light chain constant region gene, e.g., endogenous non-human light constant region gene. In another embodiment, the single rearranged variable gene sequence is operably linked to a human light chain constant region gene. In some aspects, the single rearranged variable gene sequence is a human V:J sequence inserted to the endogenous immunoglobulin light chain locus such that the resulting non-human animal does not comprise functional unrearranged V and/or J gene segments in one or more light chain loci.

Accordingly, provided herein are non-human animals bearing a heavy chain constant region comprising a deletion or inactivating mutation in a $C_H1$ encoding region and either or both (a) a light chain variable region in the context of the heavy chain constant region comprising a deletion of or inactivating mutation in a $C_H1$ region and (b) the single rearranged light chain. For example, a non-human animal as disclosed herein may comprise a nucleic acid sequence derived from one or more unrearranged immunoglobulin light chain V segments and one or more unrearranged immunoglobulin light chain J segments operably linked to a heavy chain constant region comprising a deletion or an inactivating mutation in a $C_H1$ region sequence as described herein. In one aspect, a non-human animal as disclosed herein comprises a deletion or an inactivating mutation in a nucleic acid sequence encoding an immunoglobulin $C_H1$ domain and a single rearranged light chain variable gene sequence operably linked to a light chain constant region as disclosed herein. In another aspect, a non-human animal as disclosed herein comprises a nucleic acid sequence derived from one or more unrearranged immunoglobulin light chain V segments and one or more unrearranged immunoglobulin light chain J segments operably linked to a heavy chain constant region comprising a deletion or an inactivating mutation in a $C_H1$ region sequence and a single rearranged light chain variable gene sequence operably linked to a light chain constant region. In some embodiments, the heavy chain constant region is a non-human constant region, e.g., an endogenous non-human constant region. In other embodiments, the heavy chain constant region is a human constant region.

In some aspects, a non-human animal comprises the modified heavy chain loci and/or genetically engineered rearranged light chain loci as disclosed herein in its germline. The non-human animal may also comprise a deletion or inactivating mutation in one or more of the following immunoglobulin genes: IgD, IgG3, IgG2a, IgG2b, IgG2c, IgE, IgA, and a combination thereof. In one embodiment, the non-human animal comprises a deletion or inactivating mutation in the IgG2a and IgG2b immunoglobulin genes. In another embodiment, the non-human animal comprises a deletion or inactivating mutation in the IgG3, IgD, IgA, and IgE immunoglobulin genes. In another embodiment, the non-human animal comprises a deletion or inactivating mutation in the IgG3, IgD, IgG2a, IgG2b, IgA, and IgE immunoglobulin genes.

In some aspects, a non-human animal as disclosed herein may further comprise an Adam6a gene (or fragment thereof) and/or an Adam6b gene (or fragment thereof) capable of retaining fertility of a male non-human animal. The Adam6a gene, Adam6b gene, or both may be placed ectopically, or may be at a position that approximates the position of the Adam6 gene(s) in the non-human animal. The Adam6a gene, Adam6b gene, or both are functional in a male non-human animal. For example, the non-human animal is a rodent (e.g., a mouse or a rat) and the Adam6a gene, Adam6b gene, or both are mouse or rat genes, respectively. In various embodiments, maintenance or insertion of the Adam6 gene(s) maintains or confers fertility on the male non-human animal (e.g., on the male mouse or rat).

In one aspect, the non-human animals disclosed herein comprise an IgM immunoglobulin encoded by an IgM gene sequence comprising a functional $C_H1$ domain encoding sequence, which may be associated with a cognate light chain, e.g., a genetically engineered single rearranged light chain. In another embodiment, the non-human animal produces only heavy chains having an IgM and IgG1 isotype, wherein the IgM heavy chains comprise a functional $C_H1$ domain while the IgG1 heavy chains lack a functional $C_H1$ domain. In one aspect, the cognate light chain associated with the IgM heavy chain is encoded by or derived from a single rearranged light chain variable gene sequence operably linked to a light chain constant region.

Expression of the genetically engineered single rearranged light chain as disclosed herein results in the production of a high titer of antigen specific single domain antigen binding proteins after antigen challenged by the non-human animals. A titer, e.g., an antibody or binding protein concentration, e.g., as measured by ELISA, of at least $1 \times 10^2$ μg/mL, at least $1 \times 10^3$ μg/mL, at least $1 \times 10^4$ μg/mL, or at least $1 \times 10^5$ μg/mL may be considered a high titer. Alternatively, a non-human animal produces a high titer of binding protein if the binding protein concentration is at least 2-fold, at least 5-fold, at least 10-fold, or at least 100-fold the concentration of a corresponding control animal not comprising the genetically engineered rearranged light chain.

Methods of producing a non-human animal as disclosed herein are also provided. Such methods comprise modifying the non-human heavy chain constant region of the non-human animal such that the heavy chain constant region comprises a deletion or an inactivating mutation of a nucleotide sequence encoding a $C_H1$ domain, e.g., an IgG1 $C_H1$ domain.

Methods of producing a non-human animal as disclosed herein may further comprise replacing at an endogenous immunoglobulin heavy chain locus, one or more, all, or substantially all endogenous non-human heavy chain variable region gene segments with one or more unrearranged light chain V and/or one or more unrearranged light chain J gene segments such that the light chain V and J gene segments are operably linked to a heavy chain constant region comprising a deletion or an inactivating mutation of a nucleotide sequence encoding a $C_H1$ domain. In one embodiment, the unrearranged light chain V and J gene segments are capable of undergoing productive rearrangement, e.g., comprise recombination signal sequences (RSS) that allow the unrearranged light chain V and J gene segments to recombine such that the modified non-human animal comprises a rearranged immunoglobulin light chain variable region ($V_L/J_L$) nucleotide sequence operably linked to a heavy chain constant region nucleic acid sequence, wherein the heavy chain constant region nucleic acid sequence comprises an inactivating mutation or deletion in a sequence encoding a $C_H1$ domain. In one embodiment, the unrearranged light chain V and J gene segments recombine such that the modified non-human animal comprises a rearranged immunoglobulin light chain variable region ($V_L/J_L$) nucleotide sequence that comprises 1, 2, 3, 4, 5, 6, 7, 8, 9, or 10 or more N additions and is operably linked to a heavy chain constant region nucleic acid sequence, and wherein the heavy chain constant region nucleic acid sequence comprises an inactivating mutation or deletion in a sequence encoding a $C_H1$ domain. In one embodiment, the unrearranged light chain V and J gene segments are human V and J segments. The method may also comprise causing the animal to express a $V_L$-single domain binding protein derived from the unrearranged light chain V gene segment, the unrearranged light chain J gene segment and the heavy chain constant region having an inactivated or deleted $C_H1$ domain.

In another embodiment, the methods of producing a non-human animal as disclosed herein may further comprise introducing a genetically engineered single rearranged light chain locus comprising a nucleic acid encoding a single rearranged light chain, e.g., a universal light chain (ULC), and optionally, causing the animal to express the heavy chain immunoglobulin locus having an inactivated $C_H1$ domain and the single rearranged light chain locus.

In one aspect, the methods of producing a non-human animal as disclosed herein comprises (a) modifying the non-human heavy chain constant region of the non-human animal such that the heavy chain constant region comprises a deletion or an inactivating mutation of a nucleotide sequence encoding a $C_H1$ domain, and either or both (b) replacing at an endogenous immunoglobulin heavy chain locus, one or more, all, or substantially all endogenous non-human heavy chain variable region gene segments with one or more unrearranged light chain V and/or one or more unrearranged light chain J gene segments such that the light chain V and J gene segments are operably linked to the non-human heavy chain constant region comprising a deletion or an inactivating mutation of a nucleotide sequence encoding a $C_H1$ domain, and/or (c) introducing a nucleic acid encoding a genetically engineered single rearranged light chain locus. The steps of the methods disclosed herein may be performed in any order, sequentially or simultaneously.

For example, a method as disclosed herein may comprise (a) modifying the non-human heavy chain constant region of the non-human animal such that the heavy chain constant region comprises a deletion or an inactivating mutation of a nucleotide sequence encoding a $C_H1$ domain, and (b) replacing at an endogenous immunoglobulin heavy chain locus, one or more, all, or substantially all endogenous non-human heavy chain variable region gene segments with one or more unrearranged light chain V and/or one or more unrearranged light chain J gene segments such that the light chain V and J gene segments are operably linked to the non-human heavy chain constant region comprising a deletion or an inactivating mutation of a nucleotide sequence encoding a $C_H1$ domain. In one aspect, a method as disclosed herein comprises (a) modifying the non-human heavy chain constant region of the non-human animal such that the heavy chain constant region comprises a deletion or an inactivating mutation of a nucleotide sequence encoding a $C_H1$ domain, and (b) introducing a nucleic acid encoding a genetically engineered single rearranged light chain locus. In another aspect, the method of producing a non-human animal as disclosed herein comprises (a) modifying the non-human heavy chain constant region of the non-human animal such that the heavy chain constant region comprises a deletion or an inactivating mutation of a nucleotide sequence encoding a $C_H1$ domain, (b) replacing at an endogenous immunoglobulin heavy chain locus, one or more, all, or substantially all endogenous non-human heavy chain variable region gene segments with one or more unrearranged light chain V and/or one or more unrearranged light chain J gene segments such that the light chain V and J gene segments are operably linked to the non-human heavy chain constant region comprising a deletion or an inactivating mutation of a nucleotide sequence encoding a $C_H1$ domain, and (c) introducing a nucleic acid encoding a genetically engineered single rearranged light chain locus. The methods of making a non-human animal as disclosed herein may further comprise introducing an Adam6a gene, an Adam6b gene, or both into the genome of the non-human animal, e.g., into the germline of the animal. In one aspect, the method further comprises causing the animal to express the heavy chain immunoglobulin locus having an inactivated $C_H1$ domain and/or the genetically rearranged light chain locus (single rearranged light chain locus), e.g., by immunizing the animal.

In one aspect, the step of inactivating the $C_H1$ domain(s), and optionally the hinge region(s), of a heavy chain immunoglobulin locus enables the non-human animal to produce a single domain antigen binding protein as disclosed herein. In one embodiment, inactivating the $C_H1$ domain(s), and optionally the hinge region(s) of a heavy chain immunoglobulin locus comprises targeting an endogenous heavy chain immunoglobulin locus with a targeting vector that deletes or introduces an inactivating mutation into the $C_H1$ domain(s), and optionally the hinge region, of a heavy chain locus, e.g., of an IgG heavy chain locus. In one embodiment, inactivating the $C_H1$ domain(s), and optionally, the hinge region(s) of the heavy chain immunoglobulin locus comprises homologous recombination. In another embodiment, the inactivating step may further comprise replacing of one or more, substantially all, or all of the endogenous variable region gene segments of the heavy chain gene locus with any one or more of the following: one or more heavy chain variable region gene segments, one or more light chain variable region gene segments, one or more human variable region gene segments, and one or more unrearranged variable region gene segments. The step of inactivating the $C_H1$ domain(s), and optionally hinge region(s) of the heavy chain gene locus may occur in the germline of the non-human animal.

In one aspect the method comprises introducing a nucleic acid encoding a genetically engineered rearranged light chain locus, e.g., a genetically engineered universal light chain as described herein. In one aspect, the step of introducing the nucleic acid encoding a genetically engineered rearranged light chain locus further comprises replacing all or substantially all endogenous immunoglobulin light chain loci of the non-human animal. In one aspect, the step of introducing the nucleic acid encoding a genetically engineered rearranged light chain locus further comprises functionally inactivating all or substantially all endogenous immunoglobulin light chain loci of the non-human animal. In another aspect the nucleic acid encoding a genetically engineered rearranged light chain is introduced into the germline of the animal.

In one embodiment, the method of making a non-human animal as disclosed herein comprises (a) obtaining a first non-human animal comprising a heavy chain locus having a deleted or inactivated $C_H1$ domain (and optionally a light chain variable region nucleotide sequence operably linked to heavy chain constant region sequence having the deleted or inactivated $C_H1$ domain), and optionally a deleted or inactivated hinge region such that the non-human animal produces single domain antigen binding proteins (such as a $V_L$ single domain binding protein) as disclosed herein, and (b) breeding the first non-human animal of (a) with a second non-human animal, which in one aspect may be a different strain as the first non-human animal, wherein the second non-human animal expresses a universal light chain, and wherein the breeding results in offspring that produce, e.g., comprise, a single domain antigen binding protein and a genetically engineered rearranged light chain (single rearranged light chain; ULC).

In some aspects, the methods of producing a non-human animal as disclosed herein further comprises inactivating or deleting one or more immunoglobulin genes selected from the group consisting of IgD, IgG3, IgG2a, IgG2b, IgG2c, IgE, and IgA. In one embodiment, the IgG2b and IgG2a/IgG2c immunoglobulin genes are deleted. In another embodiment, the IgD, IgG3, IgG2b, IgG2a/IgG2c, IgE, and IgA genes are deleted such that the non-human animal produces immunoglobulin heavy chains having an IgM or IgG1 isotype, wherein the IgG1 isotype has a deletion or inactivating mutation in $C_H1$ domain and optionally a hinge region.

In one aspect, a non-human animal is already capable of producing single domain antigen binding proteins and provided herein is a method of increasing the production of single domain antigen binding proteins by the non-human animal. Such method comprises causing B cells of the non-human animal to express a nucleic acid encoding a genetically engineered single rearranged light chain, e.g., a genetically engineered universal light chain as described herein. Causing the B cells to express such a nucleic acid may also comprise the step of inactivating or preventing expression of endogenous light chain genes by the B cells.

In one aspect a non-human animal as disclosed herein is a rat or a mouse. In another embodiment, a non-human animal as disclosed herein is a mouse. Accordingly, provided herein is a genetically modified mouse, comprising (a) a replacement at a mouse heavy chain locus of all or substantially all endogenous immunoglobulin heavy chain V, D, and J gene segments with one or more human heavy chain V, D, and J gene segments, wherein the one or more human heavy chain V, D, and J gene segments are operably linked to a mouse heavy chain constant region (e.g., endogenous mouse heavy chain constant region), wherein the mouse heavy chain constant region comprises a full-length IgM gene; and an IgG gene comprising a deletion or an inactivating mutation in a nucleotide sequence encoding a $C_H1$ region in an IgG gene selected from the group consisting of an IgG1, IgG2a, IgG2c, IgG2b, and a combination thereof, wherein the mouse expresses a B cell receptor that comprises an IgM with a $C_H1$ region, wherein the IgM comprises a heavy chain associated with a cognate light chain; and (b) a replacement of all or substantially all endogenous immunoglobulin light chain V and J gene segments with a single rearranged variable Vκ:Jκ gene sequence. In some embodiments, the cognate light chain is derived from the single rearranged variable Vκ:Jκ gene sequence. In some embodiments, the single rearranged variable Vκ:Jκ gene sequence is operably linked to a mouse light chain constant sequence, e.g., endogenous mouse light chain constant sequence.

In another aspect, provided herein is a non-human animal, e.g., a rat or a mouse, comprising (a) a deletion or functional inactivation at a mouse heavy chain locus of all or substantially all endogenous immunoglobulin heavy chain V, D, and J gene segments and introduction of one or more human heavy chain V, D, and J gene segments, wherein the one or more human heavy chain V, D, and J gene segments are operably linked to a mouse heavy chain constant region (e.g., endogenous mouse heavy chain constant region), wherein the mouse heavy chain constant region comprises a full-length IgM gene; and an IgG gene comprising a deletion or an inactivating mutation in a nucleotide sequence encoding a $C_H1$ region in an IgG gene selected from the group consisting of an IgG1, IgG2a, IgG2c, IgG2b, and a combination thereof, wherein the mouse expresses a B cell receptor that comprises an IgM with a $C_H1$ region, wherein the IgM comprises a heavy chain associated with a cognate light chain; and/or (b) a deletion or functional inactivation of all or substantially all endogenous immunoglobulin light chain V and J gene segments and introduction of a single rearranged variable Vκ:Jκ gene sequence.

Also provided herein is a genetically modified mouse, comprising (a) a replacement at a mouse heavy chain locus of all or substantially all endogenous immunoglobulin heavy chain V, D, and J gene segments with one or more human light chain V and J gene segments, wherein the one or more human light chain V and J gene segments are operably linked to a mouse heavy chain constant region, wherein the mouse heavy chain constant region comprises a full-length IgM gene; and an IgG gene comprising a deletion or an inactivating mutation in a nucleotide sequence encoding a $C_H1$ region in an IgG gene selected from the group consisting of an IgG1, IgG2a, IgG2c, IgG2b, IgG3, and a combination thereof, wherein the mouse expresses a B cell receptor that comprises an IgM with a $C_H1$ region, wherein the IgM comprises a heavy chain associated with a cognate light chain; and (b) a replacement of all or substantially all endogenous immunoglobulin light chain V and J gene segments with a single variable Vκ:Jκ gene sequence. In some embodiments, the cognate light chain is derived from the single rearranged variable Vκ:Jκ gene sequence.

In one aspect, a method for making an binding protein that lacks a $C_H1$ domain is provided, comprising: (a) isolating from a non-human animal as described herein the binding protein, a cell that makes the binding protein, or a nucleotide sequence that encodes a sequence of the binding protein. In one aspect, the isolating step may comprise one or more of the following steps: (a) immunizing a non-human animal as described herein with an antigen; (b) maintaining the non-human animal under conditions sufficient for the non-human animal to make a binding protein and/or (c) identifying an binding protein made by the non-human animal that lacks a functional $C_H1$ domain and/or that lacks a functional hinge region. In some aspects the binding protein so isolated is a single domain antigen binding protein. In one aspects a single domain antigen binding protein is monomeric.

In one aspect, a method for making an antigen-binding protein is provided, comprising (a) immunizing a non-human animal as described herein with an antigen; (b) maintaining the non-human animal under conditions sufficient to make an binding protein; (c) identifying an binding protein made by the non-human animal, wherein the binding protein lacks a functional $C_H1$ domain or lacks a functional $C_H1$ domain and lacks a hinge region; (d) identifying a variable region sequence encoding a variable domain on an immunoglobulin polypeptide that lacks a $C_H1$ domain, or lacks a hinge region and a $C_H1$ domain, wherein the variable domain specifically binds the antigen; (e) expressing a protein encoded by a sequence identical to or substantially identical to the variable region sequence of (d) in a suitable expression system wherein the variable region sequence of (d) is linked with a nucleic acid sequence of a heavy chain variable sequence that lacks a $C_H1$ region or lacks a $C_H1$ region and a hinge; and/or (f) isolating the expressed protein of (e). In some embodiments, the steps of expressing a protein encoded by the variable region sequence and/or (f) isolating the expressed protein comprises culturing a cell, e.g., a cell transfected with the variable region sequence, a hybridoma formed from a cell isolated from an animal disclosed herein and/or collecting supernatant from a cultured cell.

In one aspect, a method for making an antigen-binding protein is provided, comprising immunizing a non-human animal as described herein with an antigen, identifying a variable region nucleic acid sequence encoding a variable domain that specifically binds the antigen, and employing the variable region nucleic acid sequence in a suitable expression system, wherein the variable region nucleic acid sequence is linked with a heavy chain constant gene that lacks a $C_H1$ or lacks a $C_H1$ and a hinge; wherein the expression system expresses an antigen-binding protein that specifically binds the antigen.

Accordingly, also provided herein are such isolated binding proteins, cells, and nucleic acid sequences.

Other embodiments are described and will become apparent to those skilled in the art from a review of the ensuing detailed description.

BRIEF DESCRIPTION OF THE FIGURES

FIG. 1A illustrates targeting a mouse IgG1 gene, IgG2b and IgG2a genes (not to scale) to make a genetically modified mouse immunoglobulin heavy chain locus that expresses an IgG1 lacking a $C_H1$ domain; human immunoglobulin heavy chain V, D and J segments, represented by empty triangles, are inserted to a mouse constant locus wherein the IgG1 $C_H1$ exon* and IgG2a/2b** are deleted, ovals represent enhancers.

FIG. 1B illustrates a mouse immunoglobulin light chain locus (not to scale) comprising a single rearranged human $V_L/J_L$ gene sequence***.

FIG. 1C illustrates an IgM expressed by a mouse having the Ig loci of FIGS. 1A and 1B, wherein the IgM comprises an intact $C_H1$ domain. FIG. 1C also illustrates that upon class switching, the IgG1 expressed by the mouse having the Ig loci of FIGS. 1A and 1B is a single domain heavy chain antigen binding protein lacking a $C_H1$ domain.

FIG. 4A illustrates targeting a mouse heavy chain sequence (not to scale) to make a genetically modified locus that contains human heavy chain variable gene segments (empty triangles) and lacks a functional IgG1 $C_H1$ domain as well as lacks IgG2a and IgG2b loci (in some embodiments referred to as 1673).

FIG. 4B illustrates targeting a mouse IgG1 gene (all variable gene segments are mouse and indicated by the filled triangles) to make a genetically modified locus (not to scale) that expresses an IgG1 lacking a $C_H1$ domain and a hinge (in some embodiments referred to as 1576).

DETAILED DESCRIPTION

Figure 2:
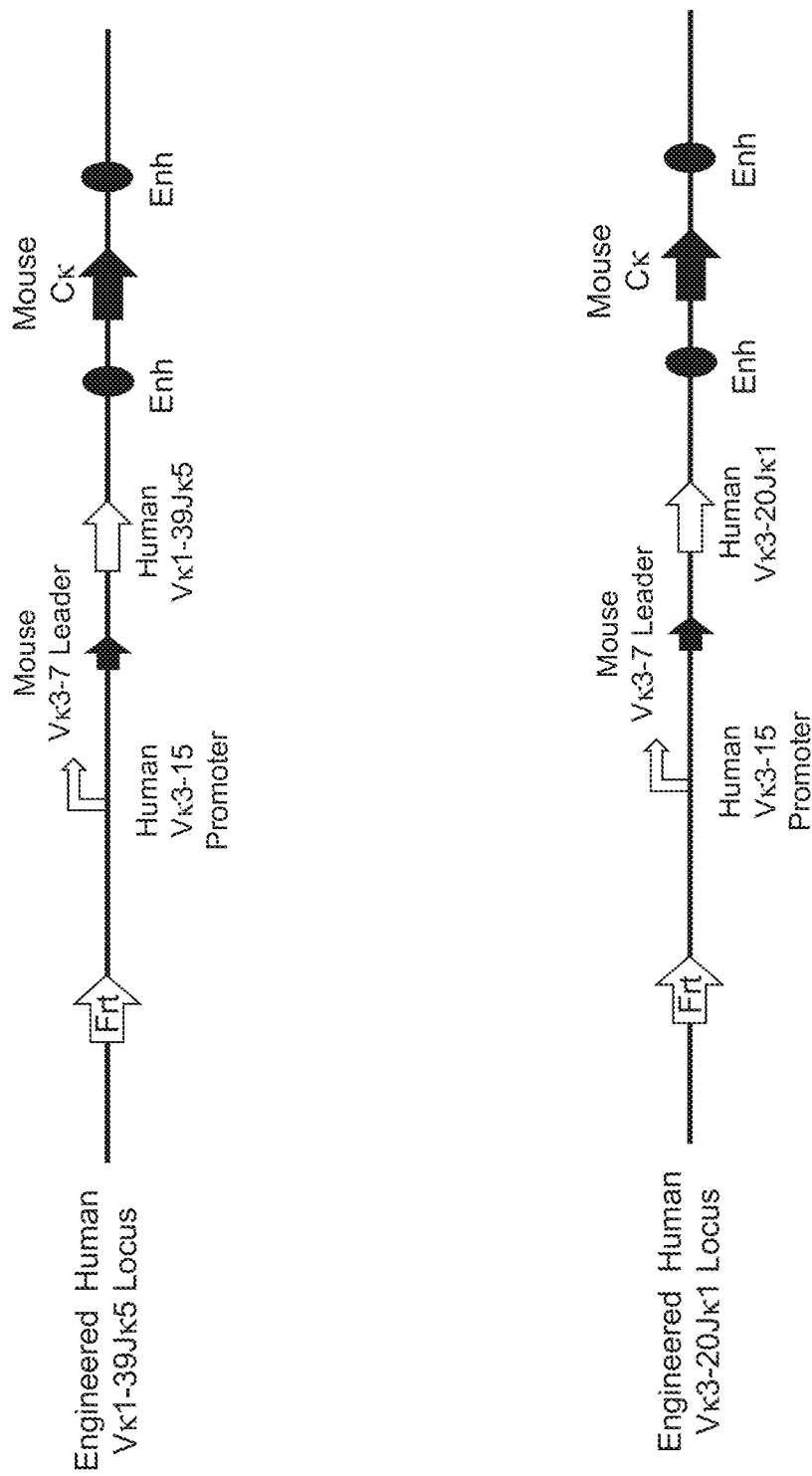
FIG. 2 illustrates the genomic structure (not to scale) of two universal light chains, one of which comprises a single rearranged human variable region comprising Vκ1-39Jκ5 and the other of which comprises a single rearranged human variable region comprising Vκ3-20Jκ1.

The invention is not limited to particular methods, and experimental conditions described, as such methods and conditions may vary. The terminology used herein is for the purpose of describing particular embodiments only, and is not intended to be limiting, since the scope of the present invention will be limited only by the claims.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, particular methods and materials are now described. All publications and patent documents mentioned herein are incorporated herein by reference in their entirety.

The present invention provides genetically modified non-human animals (e.g., mice, rats, rabbits, hamsters, etc.) that comprise in their genome, e.g., in their germline, nucleotide sequence(s) encoding single domain antigen binding proteins, including $V_H$-single domain antigen binding proteins and $V_L$-single domain antigen binding proteins, and/or a single rearranged light chain; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "antibody" includes typical immunoglobulin molecules comprising four polypeptide chains, two heavy (H) chains and two light (L) chains inter-connected by disulfide bonds. The term also includes an immunoglobulin that is reactive to an antigen or fragment thereof. Suitable antibodies include, but are not limited to, human antibodies, primatized antibodies, chimeric antibodies, monoclonal antibodies, monospecific antibodies, polyclonal antibodies, polyspecific antibodies, nonspecific antibodies, bispecific antibodies, multispecific antibodies, humanized antibodies, synthetic antibodies, recombinant antibodies, hybrid antibodies, mutated antibodies, grafted conjugated antibodies (i.e., antibodies conjugated or fused to other proteins, radiolabels, cytotoxins), and in vitro-generated antibodies. A skilled artisan will readily recognize common antibody isotypes, e.g., antibodies having a heavy chain constant region selected from the group consisting of IgG, IgA, IgM, IgD, and IgE, and any subclass thereof (e.g., IgG1, IgG2, IgG3, and IgG4).

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, a $C_H3$ domain, and a $C_H4$ domain (in the context of IgM or IgE). A functional fragment of a heavy chain includes a fragment that is capable of specifically recognizing an epitope (e.g., recognizing the epitope with a KD in the micromolar, nanomolar, or picomolar range), that is capable of expressing and secreting from a cell, and that comprises at least one CDR. A heavy chain variable domain is encoded by a variable region gene sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be viewed at the website of the International Immunogenetics Information System (IMGT) found at www.imgt.org.

The phrase "light chain" includes an immunoglobulin light chain sequence from any organism, and unless otherwise specified includes human kappa and lambda light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region. A light chain variable domain is encoded by a light chain variable region gene sequence, which generally comprises $V_L$ and $J_L$ geen segments, derived from a repertoire of $V_L$ and $J_L$ gene segments present in the germline. Sequences, locations and nomenclature for V and J light chain segments for various organisms can be viewed at the website of the International Immunogenetics Information System (IMGT) found at www.imgt.org. Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear. The phrase light chain includes a "common light chain," also referred to as a "universal light chain" (ULC).

Common or universal light chains (ULCs) include those derived from an immunoglobulin light chain locus comprising a single rearranged immunoglobulin light chain variable region encoding sequence operably linked with a light chain constant region, wherein expression of the immunoglobulin light chain locus produces only a light chain derived from the single rearranged immunoglobulin light chain variable region operably linked to the light chain constant region regardless of the inclusion of other nucleic acid sequences, e.g., other light chain gene segments, in the immunoglobulin light chain locus. Universal light chains include human Vκ1-39Jκ gene (e.g., Vκ1-39Jκ5 gene) or a human Vκ3-20Jκ gene (e.g., Vκ3-20Jκ1 gene), and include somatically mutated (e.g., affinity matured) versions of the same.

The phrase "gene segment," or "segment" includes reference to a V (light or heavy) or D or J (light or heavy) immunoglobulin gene segment, which includes unrearranged sequences at immunoglobulin loci (in e.g., humans and mice) that can participate in a rearrangement (mediated by, e.g., endogenous recombinases) to form a rearranged V/J (light) or V/D/J (heavy) sequence. Unless indicated otherwise, the V, D, and J segments comprise recombination signal sequences (RSS) that allow for V/J recombination or V/D/J recombination according to the 12/23 rule. Unless indicated otherwise, the segments further comprise sequences with which they are associated in nature or functional equivalents thereof (e.g., for V segments, promoter(s) and leader(s)).

The term "unrearranged," with reference to a nucleic acid sequence, includes nucleic acid sequences that exist in the germline of an animal cell, preferably a cell derived from an animal that has not been genetically modified, e.g., comprises a wild-type genome. Generally, in native germline configuration, the heavy chain variable region comprises unrearranged $V_H$ gene segments, unrearranged $D_H$ gene segments and unrearranged $J_H$ gene segments while the light chain variable region comprises unrearranged $V_L$ gene segments and unrearranged $J_L$ gene segments. During the B cell maturation process, these gene segments rearrange to produce a rearranged variable region gene.

The term "germline" in reference to an immunoglobulin nucleic acid sequence includes a nucleic acid sequence that can be passed to progeny.

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "somatically mutated" includes reference to a nucleic acid sequence from a B cell that has undergone class-switching, wherein the nucleic acid sequence of an immunoglobulin variable region (e.g., nucleotide sequence encoding a heavy chain variable domain or including a heavy chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" includes reference to nucleic acid sequences from affinity-matured B cells that are not identical to corresponding immunoglobulin variable region sequences in B cells that are not affinity-matured (i.e., sequences in the genome of germline cells). The phrase "somatically mutated" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The phrase "somatically mutated" refers to sequences from binding proteins that have been generated in an animal, e.g., a mouse having human immunoglobulin variable region nucleic acid sequences, in response to an immunogen challenge, and that result from the selection processes inherently operative in such an animal.

The term "cognate," when used in the sense of "cognate with," e.g., a first $V_L$ domain that is "cognate with" a second $V_L$ domain, is intended to include reference to the relation between two $V_L$ domains from a same binding protein made by a mouse in accordance with the invention. For example, a mouse that is genetically modified in accordance with an embodiment of the invention, e.g., a mouse having a heavy chain locus in which $V_H$, $D_H$, and $J_H$ regions are replaced with $V_L$ and $J_L$ regions, makes antibody-like binding proteins that have two identical polypeptide chains made of the same mouse $C_H$ region (e.g., an IgM isotype fused with a first human $V_L$ domain, and two identical polypeptide chains made of the same mouse $C_L$ region fused with a second human $V_L$ domain. During clonal selection in the mouse, the first and the second human $V_L$ domains were selected by the clonal selection process to appear together in the context of a single antibody-like binding protein. Thus, first and second $V_L$ domains that appear together, as the result of the clonal selection process, in a single antibody-like molecule are referred to as being "cognate." In contrast, a $V_L$ domain that appears in a first antibody-like molecule and a $V_L$ domain that appears in a second antibody-like molecule are not cognate, unless the first and the second antibody-like molecules have identical heavy chains (i.e., unless the $V_L$ domain fused to the first human heavy chain region and the $V_L$ domain fused to the second human heavy chain region are identical).

Early in antibody development, antibody heavy chains undergo a selection process wherein nature chooses, through a variety of selection schemes, suitable heavy chains to undergo further selection to eventually form functional and affinity-matured antibodies. Diversity arising from heavy and light chain variable gene rearrangement occurs in the bone marrow and precedes class switching. Antibody heavy chains expressed from recombined heavy chain gene segments in progenitor B cells (or, pro-B cells) are normally paired with a surrogate light chain for presentation on the surface of the pro-B cell in an IgM isotype to form a structure (which includes other co-receptors) referred to as a pre-B cell receptor, or pre-BCR. Once the pre-BCR is presented on the cell surface, the pre-BCR is believed to signal its appropriate formation of the complex to the cell, effectively instructing the cell that the heavy chain has passed this early selection step. Thus the cell is informed that the heavy chain may undergo further selection. If the heavy chain contains a defect that is deleterious to the formation of a pre-BCR when presented in the context of an IgM and a surrogate light chain, the cell will undergo apoptosis. If the cell undergoes apoptosis, the usefulness, or contribution to diversity, of the heavy chain variable region of the heavy chain will be lost. Thus, a very early step in antibody selection requires presentation of the heavy chain together with a surrogate light chain in the context of an IgM isotype. Normal development of antibody-producing B cells generally requires the presence of a $C_H1$ domain. All heavy chain isotypes, including IgM, comprise a $C_H1$ domain. Both the surrogate light chain and a cognate light chain are believed to interact with a given heavy chain through the heavy chain's $C_H1$ domain in the context of an IgM.

After B-cells exit the bone marrow, engagement with antigen (which requires a low affinity interaction between the rearranged antibody expressed as a cell-surface IgM) stimulates concerted induction of somatic hypermutation and class switching. After class switching, differential antigen recognition by the surface B-cell receptor allows antibodies of increased affinity to be selected from a pool of hyper-mutated derivatives of the original IgM.

The term "heavy chain only antibody," "heavy chain only antigen binding protein," "single domain antigen binding protein," "single domain binding protein" or the like refers to a monomeric or homodimeric immunoglobulin molecule comprising an immunoglobulin-like chain comprising a variable domain operably linked to a heavy chain constant region, that is unable to associate with a light chain because the heavy chain constant region typically lacks a functional $C_H1$ domain. Accordingly, the term "heavy chain only antibody," "heavy chain only antigen binding protein," "single domain antigen binding protein," "single domain binding protein" or the like encompasses a both (i) a monomeric single domain antigen binding protein comprising one of the immunoglobulin-like chain comprising a variable domain operably linked to a heavy chain constant region lacking a functional $C_H1$ domain, or (ii) a homodimeric single domain antigen binding protein comprising two immunoglobulin-like chains, each of which comprising al variable domain operably linked to a heavy chain constant region lacking a functional $C_H1$ domain. In various aspects, a homodimeric single domain antigen binding protein comprises two identical immunoglobulin-like chains, each of which comprising an identical variable domain operably linked to an identical heavy chain constant region lacking a functional $C_H1$ domain. Additionally, each immunoglobulin-like chain of a single domain antigen binding protein comprises a variable domain, which may be derived from heavy chain variable region gene segments (e.g., $V_H$, $D_H$, $J_H$), light chain gene segments (e.g., $V_L$, $J_L$), or a combination thereof, linked to a heavy chain constant region ($C_H$) gene sequence comprising a deletion or inactivating mutation in a $C_H1$ encoding sequence (and, optionally, a hinge region) of a heavy chain constant region gene, e.g., IgG, IgA, IgE, IgD, or a combination thereof. A single domain antigen binding protein comprising a variable domain derived from heavy chain gene segments may be referred to as a "$V_H$-single domain antibody" or "$V_H$-single domain antigen binding protein". A single domain antigen binding protein comprising a variable domain derived from light chain gene segments may be referred to as a or "$V_L$-single domain antigen binding protein".

As disclosed above, the production of single domain antigen binding proteins by non-human animals engineered to do so results in the relatively low expression of antigen-specific single domain antigen binding proteins in response to antigen compared to traditional antibodies. The art suggests that a high titer is possible only when there is little to no expression of a rearranged light chain. Specifically, it has been asserted that animals that do not express a rearranged light chain are capable of producing higher levels of single domain antigen binding proteins that specifically bind antigen. Janssens et al. (2006) *PNAS* 103:15130-15135; Zou et al. (2007) *J. Exp. Med.* 204:3271-32. Contrary to the art, the data provided herein show that animals that express a genetically engineered single rearranged light chain will generate in high titers of antigen-specific single domain antigen binding proteins after challenge. Also shown herein is the ability of light chain variable region gene segments to rearranged and recombine with a heavy chain constant region gene comprising a deletion or inactivating mutation in a $C_H1$ sequence to encode for a $V_L$-single domain antigen binding protein capable of specifically binding antigen. It is possible that the light chain variable domain of such a $V_L$-single domain antigen binding protein compensates for the lack of a cognate light chain by the addition of, e.g., 1, 2, 3, 4, 5, 6, 7, 8, 9, or 10 or more N additions in a rearranged light chain variable region gene sequence, which is not typically seen in light chain variable region gene sequences rearranged from an endogenous and unmodified immunoglobulin light chain locus.

Accordingly, in one aspect, a non-human animal is provided, wherein the animal comprises a single domain antigen binding protein and a genetically engineered single rearranged light chain, e.g., a common light chain, wherein at least one heavy chain of the single domain antigen binding protein lacks a functional $C_H1$ domain. In another aspect, a non-human animal is provided, wherein the animal comprises $V_L$-single domain antigen binding protein that comprises a light chain variable region and a heavy chain constant region lacking a functional $C_H1$ domain. In another aspect, a non-human animal is provided, wherein the animal comprises a $V_L$-single domain antigen binding protein that comprises a light chain variable region and a heavy chain constant region lacking a functional $C_H1$ domain and a genetically engineered single rearranged light chain, e.g., a common light chain. Also provided are methods of making the genetically modified non-human animal, proteins (e.g., single domain antigen binding proteins) cells isolated from the genetically modified non-human animals, and methods of isolating proteins and cells from the genetically modified animals.

The term "high affinity" antibody refers to an antibody that has a $K_D$ with respect to its target epitope about of $10^{-9}$ M or lower (e.g., about $1\times10^{-9}$ M, $1\times10^{-10}$ M, $1\times10^{-11}$ M, or about $1\times10^{-12}$ M). In one embodiment, $K_D$ is measured by surface plasmon resonance, e.g., BIACORE™; in another embodiment, $K_D$ is measured by ELISA.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The phrase "epitope-binding protein" or "antigen binding protein" includes a protein having at least one CDR and that is capable of selectively recognizing an epitope, e.g., is capable of binding an epitope with a $K_D$ that is at about one micromolar or lower (e.g., a $K_D$ that is about $1\times10^{-6}$ M, $1\times10^{-7}$ M, $1\times10^{-9}$ M, $1\times10^{-9}$ M, $1\times10^{-10}$ M, $1\times10^{-11}$ M, or about $1\times10^{-12}$ M). Therapeutic epitope-binding proteins (e.g., therapeutic binding proteins) frequently require a $K_D$ that is in the nanomolar or the picomolar range.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "identity" in connection with a comparison of sequences includes identity as determined by any of a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). The term "identity" includes the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent identity between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Representative algorithms and computer programs useful in determining the percent identity between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined for example using the GAP program in the GCG software package using an NWSgapdna.CMP matrix.

The phrase "micromolar range" is intended to mean 1-999 micromolar; the phrase "nanomolar range" is intended to mean 1-999 nanomolar; the phrase "picomolar range" is intended to mean 1-999 picomolar.

The term "operably linked" refers to a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into a rearranged immunoglobulin heavy or light chain gene sequence.

The term "replacement" in reference to gene replacement refers to placing exogenous genetic material at an endogenous genetic locus, thereby replacing all or a portion of the endogenous gene with an orthologous or homologous nucleic acid sequence.

The term "non-human animals" is intended to include any vertebrate such as cyclostomes, bony fish, cartilaginous fish such as sharks and rays, amphibians, reptiles, mammals, and birds. Suitable non-human animals include mammals. Suitable mammals include non-human primates, goats, sheep, pigs, dogs, cows, and rodents.

In some aspects of the invention, the non-human animal includes a small mammal, e.g., of the superfamily Dipodoidea or Muroidea. In one embodiment, the genetically modified animal is a rodent. In one embodiment, the rodent is selected from a mouse, a rat, a squirrel, a porcupine, or a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, *Malagasy* rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/OIa. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

"Genetically engineered," "genetically modified," and the like, as used herein includes the artificial manipulation, modification and/or recombination of a nucleic acid sequence resulting in the production of a non-native polypeptide, e.g., by an animal.

Genetically Engineered Animals for Production of Single Domain Antigen Binding Proteins Provided herein are genetically modified non-human animals that comprise (a) single domain antigen binding proteins, e.g., $V_H$ or $V_L$-single domain binding proteins, which may be respectively encoded by heavy chain variable region or light chain variable region gene sequences in a modified immunoglobulin heavy chain locus that contains one or more non-IgM immunoglobulin constant regions in which a functional $C_H1$ domain has been inactivated and/or removed while retaining an intact IgM $C_H1$ constant region, and/or (b) a genetically engineered single rearranged light chain, which may be encoded by a single rearranged variable gene sequence in a light chain locus, e.g., a single rearranged Vκ:Jκ gene sequence inserted into an immunoglobulin kappa locus.

Antibodies are useful as human therapeutics. Single domain binding proteins are also useful as human therapeutics. Because single domain binding proteins lack a light chain, they are smaller and thus expected to exhibit better tissue penetration than antibodies that contain light chains, yet have a similar or more favorable pharmacokinetic profile and yet retain similar effector function as compared to a conventional antibody. Because they are smaller, single domain binding proteins are also capable of administration at a higher dose in a given volume. A frequent method of administering binding proteins is by subcutaneous injection, and a reduction in administration volume for a given dosage of antibody can provide benefits to patients and avoid complications and pain due to subcutaneous injections of large volumes.

Another advantage of single domain binding proteins is the ability to make bispecific antibodies by heterodimerizing immunoglobulin chains with specificity for two different epitopes in a single therapeutics. Because single domain binding proteins lack a light chain, they are particularly suited for making bispecific antibodies since there is no light chain rearrangement that would create a light chain that would interfere with binding affinity or specificity of the other chain.

Observations in camelids, in certain fish, and in pathological conditions reveal that under some circumstances a binding protein that lacks a functional $C_H1$ domain in its heavy chain constant region can be expressed in the absence of a cognate light chain. Accordingly, in one embodiment, a binding protein may be referred to a "single domain binding protein," which may also be well-known in the art as an antibody devoid of light chains that comprise a light chain variable region and a light chain constant region, i.e., a "heavy chain only antibody" comprising only one or two immunoglobulin polypeptide chains each comprising heavy chain constant region, wherein at least one of the immunoglobulin polypeptide chains of the heavy chain only antibody lacks a functional $C_H1$ domain. Teachings on heavy chain only antibodies are found in the art, for example, see PCT publications WO02085944, WO02085945, WO2006008548, and WO2007096779. See also U.S. Pat. Nos. 5,840,526; 5,874,541; 6,005,079; 6,765,087; 5,800,988; EP 1589107; WO 9634103; and U.S. Pat. No. 6,015,695, incorporated herein by reference.

Non-human animals genetically modified to produce heavy chain only antigen binding proteins are well-known in the art. See, e.g., Janssens et al. (2006) *PNAS* 103:15130-15135; Zou et al. (2007) *J. Exp. Med.* 204:3271-32. For example, animals, and in particular, rodents (e.g., mice) that have been genetically modified to lack a functional $C_H1$ sequence, e.g., in an immunoglobulin G (IgG) gene, subsequently expressed single domain antigen binding proteins.

Although observations in camelids, certain fish, and in pathological conditions reveal that under some circumstances a binding protein that lacks a $C_H1$ domain of its heavy chain constant region can be expressed in the absence of a cognate light chain, normal development of antibody-producing B cells generally requires the presence of a $C_H1$ domain. All heavy chain isotypes, including IgM, comprise a $C_H1$ domain. Both the surrogate light chain and a cognate light chain are believed to interact with a given heavy chain through the heavy chain's $C_H1$ domain in the context of an IgM. To the extent that development of single domain binding proteins depends upon structural integrity or functionality of an IgM isotype heavy chain, disruption of the IgM's structural integrity or function would be undesirable.

Normal development of antibodies requires that antibodies survive throughout a multiplicity of complex selection schemes that result in the survival and ultimate expression of functional and useful antibodies. Disruptions in antibody structure can prove deleterious to the survival and ultimate expression of an antibody to the extent that the structural disruption results in the inability of the antibody to effectively compete and evolve to the satisfaction of one or more of nature's antibody selection schemes.

Early in antibody development, antibody heavy chains undergo a selection process wherein nature chooses, through a variety of selection schemes, suitable heavy chains to undergo further selection to eventually form functional and affinity-matured antibodies. Antibody heavy chains expressed from recombined heavy chain gene segments in progenitor B cells (or, pro-B cells) are normally paired with a surrogate light chain for presentation on the surface of the pro-B cell in an IgM isotype to form a structure (which includes other co-receptors) referred to as a pre-B cell receptor, or pre-BCR. Once the pre-BCR is presented on the cell surface, the pre-BCR is believed to signal its appropriate formation of the complex to the cell, effectively instructing the cell that the heavy chain has passed this early selection step. Thus the cell is informed that the heavy chain may undergo further selection. If the heavy chain contains a defect that is deleterious to the formation of a pre-BCR when presented in the context of an IgM and a surrogate light chain, the cell will undergo apoptosis. If the cell undergoes apoptosis, the usefulness, or contribution to diversity, of the heavy chain variable region of the heavy chain will be lost. Thus, a very early step in antibody selection requires presentation of the heavy chain together with a surrogate light chain in the context of an IgM isotype. The surrogate light chain is believed to interact with IgM at least in part through IgM's $C_H1$ domain. A failure or disruption in antibody structure at this early juncture (e.g., a nonfunctional $C_H1$ domain) can result in clonal selection failure, loss of the pro-B cell that expresses the heavy chain, and loss of the possibility of employing the particular heavy chain variable domain in a useful antibody.

Once the cell bearing the pre-BCR passes this selection step, the next selection step requires that the heavy chain be paired with a cognate light chain (e.g., either kappa or lambda in mice and humans). The paired heavy chain/cognate light chain structure is again presented on the surface of the cell, now a naive pre-B cell, in the context of an IgM isotype through the IgM's $C_H1$ domain. This complex on the surface results in a functional, membrane-bound, B cell receptor (BCR). This BCR is believed to signal to the cell that the heavy chain is suitable for further selection, and that the cell may now commit to expressing this particular light chain and proceed to further B cell maturation steps, including affinity maturation and class switching. If the heavy chain contains a defect that is deleterious to the formation of a BCR when presented in the context of an IgM and its cognate light chain, the cell will undergo apoptosis. If the cell undergoes apoptosis, the usefulness, or contribution to diversity, of the heavy chain variable region of the heavy chain will be lost. Thus, a very early step in antibody selection requires presentation of the heavy chain together with a cognate light chain in the context of an IgM isotype. Again, a failure or disruption in antibody structure (e.g., a non-functional $C_H1$ domain) at this early juncture can result in clonal selection failure and concomitant loss of the pre-B cell that expresses the heavy chain.

Having survived selection thus far, the pre-B cell that presents the heavy chain paired with its cognate light chain in the IgM context then undergoes a maturation process that ultimately results in class switching and further selection mechanisms in which the heavy chain and cognate light chain are presented on the B cell surface in the context of an IgG isotype. It would be at this step that any selection of IgG heavy chains that lack a $C_H1$ domain or that lack a $C_H1$ domain and a hinge region would occur. In animals according to the invention, it is believed that an increased repertoire of variable regions at a heavy chain locus would be available for selection based upon whether the variable domain would survive to be expressed in an IgG heavy chain that lacks a $C_H1$ domain or that lacks a $C_H1$ domain and a hinge region. In contrast, mice that have impaired IgM would likely not present a full repertoire of heavy chain variable regions, since only those variable regions capable of surviving selection in the context of an impaired IgM would be available for class switching.

Thus, an animal lacking a functional IgM may experience a marked reduction in the ability to make a B cell population following rearrangement of otherwise suitable heavy chain variable gene segments. In such a case, even where an ample supply of variable regions is available (i.e., the animal has a suitable number of variable region gene segments capable of rearranging and operably linking to a heavy chain constant region, e.g., in a heavy chain immunoglobulin locus), a satisfactory population of B cells that display a desirable degree of diversity may not form because of an IgM impairment that mitigates against survival of a heavy chain during the selection process.

A suitable number of rearranged variable regions in a heavy chain immunoglobulin locus that can effectively survive selection when presented during B cell development in the context of an IgM is desirable to be maintained in order to generate sufficient diversity to make antibodies by immunizing a non-human animal with an immunogen of interest. Thus, a genetically modified non-human animal that comprises a nonfunctional $C_H1$ domain or a nonfunctional $C_H1$ domain and, optionally, a nonfunctional hinge region, in an immunoglobulin heavy chain should not comprise a $C_H1$ deletion in either or both IgM alleles. Such animals, disclosed in US 2011/0145937, which is incorporated herein by reference, exhibit class switching to a IgG constant gene region wherein the $C_H1$ domain has been deleted or inactivated and express a single-domain, surface IgG (B-cell receptor) that both 1) folds and expresses at the cell surface without a light-chain partner, and 2) still recognizes antigen in the absence of light chain, in order to be stimulated by antigen and selected.

In various embodiments of the present invention, genetically modified non-human animals are provided that make binding proteins that lack a $C_H1$ domain, including single domain antigen binding proteins, such as but not limited to $V_H$ and $V_L$ single domain binding proteins. The genetically modified non-human animals may comprise a genetic modification that includes a lack of a functional immunoglobulin heavy chain domain (a $C_H1$ domain), e.g., an IgG1 $C_H1$ domain, and in some embodiments a further modification comprising a deletion of a hinge region in the immunoglobulin heavy chain that lacks the functional $C_H1$ domain, wherein the non-human animal expresses a functional IgM. Other modifications include rendering isotypes other than IgG1 and IgM to be nonfunctional, e.g., making deletions in genes, or deletions of genes, or inactivating mutations in genes, for IgD, IgG3, IgG2a, IgG2c, IgG2b, IgA, and IgE, such as deletions or inactivating mutations of CH1 domains or hinge regions of IgD, IgG3, IgG2a, IgG2c, IgG2b, IgA, and IgE. Genetically modified non-human embryos, cells, and targeting constructs for making the non-human animals, non-human embryos, and cells are also provided.

Compositions and methods are also provided for making an animal that makes a binding protein that lacks an immunoglobulin $C_H1$ domain (and optionally a hinge region), including single domain antigen binding proteins, which may comprise $V_H$ domains (e.g., endogenous or human $V_H$ domains) or $V_L$ domains (e.g., human $V_L$ domains). The methods include selectively rendering an endogenous non-IgM $C_H1$ region to be nonfunctional (e.g., by a deletion or inactivation of a sequence of a $C_H1$ domain), and employing either unrearranged endogenous heavy chain variable region (HCVR) gene segments, unrearranged human variable region (hHCVR) gene segments, or unrearranged human light chain variable region (hLCVR) at the endogenous variable region locus to make a chimeric human binding protein in a non-human. The deletion of the $C_H1$ domain is made in one or more immunoglobulin constant region genes (e.g., IgG1, IgD, IgG3, IgG2a, IgG2c, IgG2b, IgA, or IgE genes), but not in an IgM gene. In an embodiment wherein the deletion is in an IgG, this approach selectively renders one or more IgG $C_H1$ domains nonfunctional while retaining a functional IgM. In addition to a deletion of the one or more IgG $C_H1$ domains, a further embodiment provides for deleting or rendering nonfunctional the hinge region(s) of the IgG(s) lacking a functional $C_H1$ domain.

In this particular embodiment, the IgG $C_H1$ deletion approach employs a relatively conservative disruption in natural B cell development in the animal, because not all Ig isotypes of the genetically modified non-human animal will exhibit a nonfunctional $C_H1$ or a deletion of the $C_H1$ domain (and, optionally, hinge). Thus, the $C_H1$ modification does not occur in IgM molecules and thus does not affect those steps, as described above, in early B cell development that depend on an IgM having a functional $C_H1$. Because the IgM is not modified, animals bearing one or more deletions of the $C_H1$ domain of an IgG (and optionally a hinge region of the IgG), but not the $C_H1$ domain of an IgM, should be able to process a satisfactorily large repertoire of variable regions in clonal selection steps prior to presentation of the variable domain in the context of an IgG. Thus in various embodiments, any deleterious effect of the genetic modification(s) on the diversity of variable regions available for use in a single domain binding protein should not negatively impact the pool of variable regions available for selection in an IgG context. Further, where the $C_H1$ sequence that is rendered nonfunctional (e.g., deleted) in the germline is an IgG1, the animal will lack the ability to make any RNA that encodes a $C_H1$ domain.

Genetically modifying a non-human animal to render a $C_H1$ domain or a $C_H1$ domain and, optionally, a hinge region of one or more non-IgM immunoglobulin isotype nonfunctional may result in an animal that is able to select, from a full or substantially full repertoire of V region gene segments, e.g., $V_H$ or $V_L$ regions, a suitable V region to express in a single domain binding protein. Selectively modifying IgG isotypes (but not IgM) avoids a potential reduction in the number of variable regions that survive selection due to a lack of a $C_H1$ domain or a lack of a $C_H1$ domain in IgM. Thus, a fuller repertoire of V regions is available for selection in the context of an IgG (that lacks a $C_H1$ domain or that lacks a $C_H1$ domain and that lacks a hinge region). Thus, selection of a V domain in a genetically modified animal in accordance with the invention does not depend, e.g., on which V domain might help overcome early IgM-dependent B cell developmental hurdles that are due to modified IgM structures. Instead, early IgM-dependent steps should occur as normal, resulting in a large repertoire of heavy chains available for selection as to their suitability to express in the context of an IgG that lacks a $C_H1$ domain or that lacks a $C_H1$ domain and lacks a hinge region.

Thus, in various embodiments, a genetically modified animal in accordance with the invention should maintain functional IgM expression, which should provide an opportunity for a more natural clonal selection process. For example, with a functional IgM (e.g., an IgM that comprises a functional $C_H1$ domain), both surrogate light chain and the cognate light chain will be able to associate through the IgM's $C_H1$ domain and participate in selection processes in early B cell development. In a genetically modified animal in accordance with the invention, it is believed that class switching to an IgG isotype is the first selection step where any selection of heavy chain variable domains that can be expressed in the context of a constant domain lacking a functional $C_H1$ domain or lacking a functional $C_H1$ domain and a functional hinge is encountered.

In various embodiments, the non-IgM heavy chain constant region in the non-human animal that comprises a deletion or an inactivating mutation in the CH1 domain is a non-human, e.g., endogenous non-human heavy chain constant region. In another embodiment, the non-IgM heavy chain constant region in the non-human animal that comprises a deletion or an inactivating mutation in the CH1 domain is a human heavy chain constant region. In yet other embodiments, wherein the animal additionally comprises a single rearranged light chain gene sequence operably linked to a light chain constant region, the light chain constant region is a non-human, e.g., endogenous non-human light chain constant region; or the light chain is a human light chain constant region.

$V_L$-Single Domain Binding Proteins, e.g., Single Domain Antigen Binding Proteins Having a Light Chain Variable Domain Provided herein are genetically modified non-human animals comprising two types of single domain antigen binding proteins: (1) a $V_H$ single domain binding protein, which is encoded by a rearranged heavy chain variable region gene sequence and (2) a $V_L$ single domain binding protein, which is encoded by a rearranged light chain variable region gene sequence, each also encoded by a modified immunoglobulin heavy chain locus that contains one or more non-IgM immunoglobulin constant regions in which a functional $C_H1$ domain has been inactivated and/or removed while retaining an intact IgM $C_H1$ constant region.

Thus, in one embodiment provided herein is a heavy chain locus genetically engineered to comprise light chain variable region gene segments, e.g., Vκ, Jκ, Vλ, and/or Jλ gene segments, operably linked to a heavy chain constant region. The genetic engineering of a heavy chain locus to comprise a light chain variable region has been described. For example, generation of a non-human animal comprising an immunoglobulin heavy chain locus comprising a replacement of one or more, substantially all, or all immunoglobulin heavy chain variable region $V_H$, $D_H$, and/or $J_H$ gene segments with one or more light chain variable region $V_L$ and/or $J_L$ gene segments is described in, e.g., U.S. Patent Application No. 20120096572, which is incorporated herein by reference in its entirety.

A skilled artisan will readily recognize that the replacement $V_L$ and/or $J_L$ gene segments may comprise unrearranged $V_L$ and/or unrearranged $J_L$ gene segments, which are capable of undergoing productive rearrangement. Additionally, the $V_L$ and/or $J_L$ gene segments may be one or more segments selected from Vκ, Jκ, Vλ, Jλ gene segments, and may be a combination thereof. In one embodiment, the one or more heavy chain variable region gene segments are replaced with one or more human light chain variable gene segments, which allows for the production of a variable domain having human idiotypes.

As provided herein, a heavy chain locus genetically engineered to comprise light chain variable region gene segments, e.g., Vκ, Jκ, Vλ, and/or Jλ gene segments, operably linked to a heavy chain constant region may undergo productive gene rearrangement to form an immunoglobulin chain, even when one or more domains or gene segments of the heavy chain constant region is inactivated or deleted. As shown herein, replacement of the heavy chain variable region gene segments with light chain variable region gene segments coupled with deletion of a $C_H1$ domain, e.g., in the IgG1 gene, results in single domain antigen binding proteins having light chain variable regions. Specifically, replacement of endogenous heavy chain variable region gene segments of a heavy chain locus with kappa (κ) V and J gene segments (Vκ and Jκ) results in a kappa variable region operably linked to a heavy chain constant region (KoH). Further modification to the heavy chain locus to delete the $C_H1$ domain(s) ($C_H1$ del) results in an immunoglobulin locus (KoH $C_H1$ del) that encodes for an immunoglobulin polypeptide chain comprising a light chain variable region and a heavy chain constant region that lacks a functional $C_H1$ domain, wherein the immunoglobulin polypeptide chain may form a single domain antigen binding protein, e.g., a $V_L$-single domain antigen binding protein.

Accordingly, in some embodiments, provided are genetically modified non-human animals that comprise a $V_L$ single domain binding protein comprising a light chain variable domain operably linked to a heavy chain constant region that lacks a functional $C_H1$ domain, wherein the immunoglobulin polypeptide chain may form a single domain antigen binding protein, which may be encoded by light chain variable regions gene sequences in a modified immunoglobulin heavy chain locus that contains one or more non-IgM immunoglobulin constant regions in which a functional $C_H1$ domain has been inactivated and/or removed while retaining an intact IgM constant region.

Aspects described herein include $V_L$ binding proteins that comprise a hybrid chain encoded by a hybrid immunoglobulin gene comprising or derived from a, preferably unrearranged and more preferably human, $V_L$ gene segment (or portion thereof) rearranged with a, preferably unrearranged and more preferably human, $J_L$ gene segment (or portion thereof) operably linked to nucleotide sequences that encode one or more heavy chain constant region genes, e.g., IgM, IgD, IgG, IgA or IgE, wherein the IgD, IgG, IgA or IgE gene comprises a deletion or inactivating mutation in a $C_H1$ encoding sequence. $V_L$ binding protein, antigen binding $V_L$ protein, or the like, includes an antigen binding protein comprising an antigen binding site comprising two light chain variable domains. In one embodiment, at least two light chain variable domains of the $V_L$ binding proteins are cognate. In some embodiments, each of the two light chain variable domains are encoded by or derived from a light chain variable region ($V_L$) gene segment and/or a light chain joining region ($J_L$) gene segment. In preferred embodiments, one of the two light chain variable domains may be part of a hybrid immunoglobulin chain, and the other of the two light chain variable domains may be part of an immunoglobulin light chain (L).

The phrase "immunoglobulin hybrid chain," "hybrid chain," "hybrid immunoglobulin chain," or the like as used herein refers to an immunoglobulin protein that includes, from amino terminus to carboxyl, a light chain variable domain (which may or may not be somatically mutated) and a heavy chain constant region. Generally, a hybrid chain is encoded by a rearranged light chain variable region gene sequence operably linked to a heavy chain constant region gene sequence. As disclosed herein, a $V_L$-single domain binding protein comprises a hybrid chain, wherein the hybrid chain is encoded by a rearranged light chain variable region gene sequence operably linked to a heavy chain constant region gene sequence having a deletion or inactivating mutation in a $C_H1$ encoding sequence.

The light chain variable region gene sequence of a hybrid immunoglobulin chain may generally comprise sequences from light chain variable ($V_L$) gene segment (or portion thereof) and a light chain joining ($J_L$) gene segment (or portion thereof). In preferred embodiments, the light chain variable region gene sequence, e.g., the rearranged $V_L$-$J_L$ gene sequence, encoding the hybrid chain variable domain is derived from a repertoire of unrearranged $V_L$ and $J_L$ gene segments, preferably germline unrearranged $V_L$- and $J_L$- gene segments, which are (a) capable of undergoing productive gene rearrangement, e.g., capable of rearranging to form an in-frame light chain variable region gene sequence and (b) operably linked to one or more heavy chain constant region gene segments, e.g., an unrearranged cluster of constant region gene segments or one constant region gene segment.

Upon rearrangement of the light chain gene segments, a rearranged nucleotide sequence is obtained that comprises a sequence encoding a light chain variable region fused with a sequence encoding a heavy chain constant region. This sequence encodes a hybrid immunoglobulin chain that has a light chain variable domain fused with a heavy chain constant domain. Thus, in one embodiment, a hybrid immunoglobulin as disclosed herein consists essentially of, from N-terminal to C-terminal, a $V_L$ domain and a $C_H$ domain. In one embodiment, the $C_H$ domain comprises a functional $C_H1$ region (in the context of IgM), a hinge, a $C_H2$ region, a $C_H3$ region, and optionally a $C_H4$ region. In another embodiment, the $C_H$ domain lacks a functional $C_H1$ region, e.g., lacks a $C_H1$ region in whole or in part, and may additionally lack a hinge region, e.g., in the context of IgG, IgA, IgE and/or IgD. In another embodiment, the $C_H$ domain lacks a functional $C_H1$ region, e.g., lacks a $C_H1$ region in whole or in part, and may additionally lack other non-IgM isotype constant regions.

The modified non-human animals described herein may generate $V_L$ binding proteins having an IgM isotype that also comprise a cognate light chain paired with a hybrid chain to make a $V_L$ binding protein that is antibody-like, e.g., may be tetrameric, but wherein instead of a heavy chain (or pair of heavy chains) the $V_L$ binding protein comprises a hybrid chain (or pair of hybrid chains) that comprises $V_L$ domain—not a $V_H$ domain—fused to a IgM $C_H$ domain.

Since the non-human animals disclosed herein preferably comprise an IgM constant region gene having a functional $C_H1$ domain, the non-human animals disclosed herein also encompasses the humanization of immunoglobulin loci resulting in expression of $V_L$ binding proteins that resemble some conventional antibodies' tetrameric structure yet differ in binding characteristics, and resulting in expression of said $V_L$ binding proteins on the membrane surface of cells of the non-human animal. In some embodiments, non-human animals of the present invention are capable of generating human $V_L$ domains, on either or both the hybrid and light chains of the $V_L$ binding protein, that bind to antigen; in some embodiments, such non-human mammals develop and/or have a B cell population that express binding proteins comprising variable domains that are not encoded by or derived from any $V_H$, $D_H$ and/or $J_H$ gene segment sequences. In some embodiments, $V_L$ binding proteins expressed by such non-human animals are characterized in that the antigen-binding portion is comprised exclusively of human $V_L$ domains. In some embodiments, non-human animals of the present invention comprise at an endogenous immunoglobulin heavy chain locus genetic material from the non-human animal and a heterologous species (e.g., a human) and comprise at an endogenous immunoglobulin light chain locus genetic material from the non-human animal and a heterologous species (e.g., human).

In various embodiments, the modified non-human animals make $V_L$ single domain binding proteins, wherein the $V_L$ domain of a hybrid chain exhibits an enhanced degree of somatic hypermutation over a $V_L$ domain of a light chain. In some embodiments, a $V_L$ region of a hybrid chain exhibits about 1.5-fold, 2-fold, 2.5-fold, 3-fold, 3.5-fold, 4-fold, 4.5-fold, or 5-fold or more somatic hypermutations than a $V_L$ region fused with a $C_L$ region. In some embodiments, the modified non-human animal, e.g., mouse, in response to an antigen exhibits a population of $V_L$ single domain binding proteins that comprise a $V_L$ domain of a hybrid chain, wherein the population of $V_L$ single domain binding proteins exhibits an average of about 1.5-fold, 2-fold, 2.5-fold, 3-fold, 3.5-fold, 4-fold, 4.5-fold, 5-fold or more somatic hypermutations in the $V_L$ domain of the hybrid chain than is observed in a population of light chains, e.g., a $V_L$ domain of a light chain, exhibited by a wild-type mouse in response to the same antigen.

In one embodiment, the somatic hypermutations in the $V_L$ domain of the hybrid chain comprises one or more or two or more N additions in a CDR3. In various embodiments, the $V_L$ binding proteins, e.g., $V_L$ single domain binding proteins, comprise hybrid chains comprising variable domains encoded by immunoglobulin light chain sequences that comprise a larger number of N additions than observed in nature for light chains rearranged from an endogenous light chain locus, e.g., the $V_L$ and human $J_L$ gene segments rearrange to form a rearranged variable region gene operably linked with a heavy chain constant region gene, wherein the rearranged light chain variable region comprises 1, 2, 3, 4, 5, 6, 7, 8, 9, or 10 or more N additions.

In various embodiments, $V_L$ binding proteins, e.g., $V_L$ single domain binding proteins, as disclosed herein, e.g., those produced by the genetically modified non-human animals, e.g., mice, disclosed herein, may be on average smaller than conventional antibodies or heavy chain only antibodies, respectively and possess advantages associated with smaller size. Smaller size is realized at least in part through the absence of an amino acid sequence encoded by a $D_H$ region, normally present in a $V_H$ domain. Smaller size can also be realized in the formation of a CDR3 that is derived, e.g., from a Vκ region and a Jκ region.

In one aspect, a non-human animal, e.g., a mouse, is provided, comprising an immunoglobulin hybrid chain locus. In one embodiment, the hybrid chain locus is created within an endogenous heavy chain locus, wherein one or more immunoglobulin heavy chain variable region ($V_H$) gene segments, heavy chain diversity ($D_H$) gene segments, and heavy chain joining ($J_H$) gene segments at an endogenous mouse immunoglobulin heavy chain locus are replaced with one or more light chain variable region ($V_L$) gene segments and one or more light chain joining region ($J_L$) gene segments that rearrange to form a rearranged variable region $V_L/J_L$ gene sequence recombining with an endogenous mouse $C_H$ gene to form a rearranged gene that is derived from a $V_L$ gene segment, a $J_L$ gene segment, and an endogenous mouse $C_H$ gene, wherein the $C_H$ gene is IgM, IgD, IgG, IgA, IgE, and wherein the IgD, IgG, IgA, or IgE lack a functional $C_H1$ domain. In one aspect, a non-human animal is provided, comprising a hybrid chain locus that replaces the endogenous immunoglobulin heavy chain locus, e.g., all or substantially all endogenous $V_H$, $D_H$, and $J_H$ gene segments of one or both heavy chain loci are replaced with one or more $V_L$ gene segments and one or more $J_L$ gene segments that form a rearranged variable region $V_L/J_L$ gene sequence recombining with an endogenous mouse $C_H$ gene to form a rearranged gene that is derived from a $V_L$ gene segment, a $J_L$ gene segment, and an endogenous mouse $C_H$ gene, wherein the $C_H$ gene is IgM, IgD, IgG, IgA, IgE, and wherein the IgD, IgG, IgA, or IgE lack a functional $C_H1$ domain.

In some embodiments, non-human animals of the present invention comprise an immunoglobulin hybrid chain locus that includes unrearranged human $V_L$ gene segments and/or human $J_L$ gene segments and an immunoglobulin light chain locus that includes unrearranged human $V_L$ gene segments and/or human $J_L$ gene segments. In some embodiments, non-human animals of the present invention comprise an immunoglobulin hybrid chain locus that includes unrearranged human $V_L$ gene segments and/or human $J_L$ gene segments and, preferably, an immunoglobulin light chain locus that includes a single rearranged human $V_L/J_L$ variable region gene sequence operably linked to a light chain constant region gene sequence, e.g., and that encodes a common light chain.

Genetically Engineered Non-Human Animals Expressing Single Domain Binding Proteins and a Rearranged Light Chain In additional embodiments, provided herein are non-human animals comprising (a) a deletion or inactivating mutation in a nucleotide sequence encoding a $C_H1$ domain of at least one endogenous immunoglobulin heavy chain constant region gene at an endogenous immunoglobulin heavy chain locus, wherein the at least one endogenous immunoglobulin heavy chain constant region gene is IgG, IgA, IgE, IgD, or a combination thereof, (b) an immunoglobulin light chain locus that comprises a single rearranged immunoglobulin light chain variable region $V_L/J_L$ gene sequence comprising $V_L$ and $J_L$ gene segment sequences, wherein the single rearranged immunoglobulin light chain variable region gene sequence is operably linked to an immunoglobulin light chain constant region gene sequence, and, e.g., encodes a single light chain, and optionally also (c) a replacement of endogenous $V_H$, $D_H$, $J_H$ gene segments at the endogenous immunoglobulin heavy chain locus with a nucleic acid sequence comprising at least one unrearranged immunoglobulin light chain variable region ($V_L$) gene segment and at least one unrearranged immunoglobulin light chain joining ($J_L$) gene segment, wherein each of the unrearranged $V_L$ and $J_L$ gene segments are capable of recombining to form a rearranged immunoglobulin light chain variable region ($V_L/J_L$) nucleotide sequence operably linked to the immunoglobulin heavy chain constant region gene comprising the deletion or inactivating mutation in the nucleotide sequence encoding the $C_H1$ domain.

The genetic engineering of a single rearranged light chain, e.g., a light chain comprising a rearranged light chain variable region has been described. For example, generation of a universal light chain mouse (ULC) comprising a single rearranged variable gene sequence $V_L$:$J_L$ and generation of antigen-specific antibodies in those mice is described in, e.g., U.S. patent application Ser. Nos. 13/022,759, 13/093, 156, 13/412,936, 13/488,628, 13/798,310, and 13/948,818 (Publication Nos. 2011/0195454, 2012/0021409, 2012/0192300, 2013/0045492, US20130185821, and US20130302836 respectively), each of which is incorporated herein by reference in its entirety. The expression of a genetically engineered single rearranged light chain, e.g., a universal light chain, causes expansion of antibodies at the early IgM stage, where the bulk of the diversity and thus antigen recognition occurs on the heavy chain. Without limitation as to the invention, it is proposed that expansion at the early IgM stage with a genetically engineered single rearranged light chain will result in more cells that bear the heavy or light chain variable regions capable of surviving to undergo class-switching to an IgG isotype and selection in the context of an IgG that lacks a functional $C_H1$ domain or that lacks a functional $C_H1$ domain and lacks a functional hinge region.

Accordingly, a genetically modified non-human animal is provided, along with methods and compositions for making the animal, wherein the genetic modification results in lack of a functional $C_H1$ domain (in a further embodiment lack of a functional hinge region) in an Ig domain that is not an IgM domain, and wherein the animal further expresses a genetically engineered single rearranged light chain, e.g., an engineered common light chain (ULC), which may associate with an intact IgM.

The engineered common light chain mouse described in U.S. Application Publication Nos. 2011/0195454, 2012/0021409, 2012/0192300 and 2013/0045492 comprised nucleic acid sequence encoding a limited repertoire of light chain options, e.g., common or universal light chain "ULC" that comprised no more than two $V_L$ gene segments or a single rearranged human immunoglobulin light chain variable region sequence. To achieve such limited repertoire, a mouse was engineered to render nonfunctional or substantially nonfunctional its ability to make, or rearrange, a native mouse light chain variable domain. In one aspect, this was achieved, e.g., by deleting the mouse's light chain variable region gene segments. As previously described, the endogenous mouse locus can then be modified by exogenous suitable light chain variable region gene segments of choice, preferably human light chain variable region gene segments, operably linked to the endogenous mouse light chain constant domain, in a manner such that the exogenous variable region gene segments can combine with the endogenous mouse light chain constant region gene and form a rearranged reverse chimeric light chain gene (human variable, mouse constant). In various embodiments, the light chain variable region is capable of being somatically mutated. In various embodiments, to maximize ability of the light chain variable region to acquire somatic mutations, the appropriate enhancer(s) is retained in the mouse. In one aspect, in modifying a mouse κ light chain locus to replace endogenous mouse κ light chain gene segments with human κ light chain gene segments, the mouse κ intronic enhancer and mouse κ 3' enhancer are functionally maintained, or undisrupted.

Thus, provided was a genetically engineered mouse that expresses a limited repertoire of reverse chimeric (human variable, mouse constant) light chains associated with a diversity of reverse chimeric (human variable, mouse constant) heavy chains. In various embodiments, the endogenous mouse κ light chain gene segments are deleted and replaced with a single (or two) rearranged human light chain region, operably linked to the endogenous mouse Cκ gene. In embodiments for maximizing somatic hypermutation of the rearranged human light chain region, the mouse κ intronic enhancer and the mouse κ 3' enhancer are maintained. In various embodiments, the mouse also comprises a nonfunctional λ light chain locus, or a deletion thereof or a deletion that renders the locus unable to make a λ light chain.

Thus, in one embodiment, provided herein is a non-human animal (e.g., a rodent, e.g., a mouse or a rat) that comprises in its genome, e.g., in its germline, a limited repertoire of preferably human light chain variable regions, or a single rearranged human light chain variable region, from a limited repertoire of preferably human light chain variable gene segments, wherein the non-human animal also comprises in its genome, e.g., in its germline, a deletion or inactivating mutation in a nucleotide sequence encoding a $C_H1$ domain.

Genetically engineered animals are provided that express a limited repertoire of human light chain variable domains, or a single human light chain variable domain, from a limited repertoire of human light chain variable region gene sequences. In one embodiment, the single rearranged V/J human light chain sequence is selected from Vκ1-39Jκ and Vκ3-20Jκ, e.g., Vκ1-39Jκ5 and Vκ3-20Jκ1. In some embodiments, a non-human animal as disclosed herein comprises a modified light chain locus comprising a replacement all endogenous $V_L$ and all endogenous $J_L$ gene segments with the single rearranged V/J light chain sequence, wherein the single rearranged V/J light chain sequence is operably linked to an endogenous light chain constant region gene. In some embodiments, the modified light chain locus is in the germline genome of the non-human animal. In one embodiment, the non-human animal comprises in its germline genome a single rearranged light chain variable gene sequence operably linked to a light chain constant region gene sequence, wherein the single rearranged light chain variable region gene sequence comprises human germline $V_L$ and human germline $J_L$ gene segments, e.g., human germline Vκ1-39 and human germline Jκ5 or human germline Vκ3-20 and Jκ1. In some embodiments, a non-human animal as disclosed herein comprises a B cell, e.g., a B cell that has not undergone class switching, comprising in its genome a single rearranged V/J light chain sequence operably linked to an endogenous light chain constant region gene, wherein the single rearranged V/J light chain does not comprise somatic mutations compared to a single rearranged V/J light chain sequence operably linked to an endogenous light chain constant region gene found in the germline genome of the non-human animal. In other embodiments, a non-human animal as disclosed herein comprises a B cell, e.g., a B cell that has undergone class switching, comprising in its genome a single rearranged V/J light chain sequence operably linked to an endogenous light chain constant region gene, wherein the single rearranged V/J light chain comprises somatic mutations compared to a single rearranged V/J light chain sequence operably linked to an endogenous light chain constant region gene found in the germline genome of the non-human animal.

Making Genetically Modified Animals

Methods of producing a non-human animal as disclosed herein are also provided. Such methods comprise (a) inactivating or deleting the $C_H1$ domain, and optionally the hinge region(s), of a heavy chain immunoglobulin locus of the non-human animal, such as the IgG1 heavy chain locus, introducing a nucleic acid encoding a genetically engineered rearranged light chain locus, and causing the animal to express the heavy chain immunoglobulin locus having an inactivated $C_H1$ domain and the genetically rearranged light chain locus (ULC).

Genetic modifications for making an animal that expresses a single domain binding protein are conveniently described herein by using the mouse as an illustration, although such modifications may be easily adapted and applied to other animals. A genetically modified animal according to the invention can be made in a variety of ways, particular embodiments of which are discussed below.

An exemplary schematic illustration (not to scale) of an IgG1 locus is provided in FIG. 1 (top) to show $C_H$ domain arrangement at the IgG1 locus. As illustrated, domains $C_H1$, $C_H2$, and $C_H3$ and the hinge region are present in readily identifiable spans of nucleotide downstream of a switch region.

A genetically modified non-human animal, e.g., mouse, lacking a functional nucleotide sequence encoding a $C_H1$ domain of an IgG1 but containing a hinge region can be made by any method known in the art. For example, a targeting vector can be made that replaces the IgG1 gene with a truncated IgG1 lacking a $C_H1$ domain but containing the hinge. In one example, a mouse genome is targeted by a targeting construct having a 5' (with respect to the direction of transcription of the genomic IgG1 gene) homology arm containing sequence upstream of the endogenous $C_H1$ domain, followed by nucleotide sequences that encode an IgG1 hinge, an IgG1 $C_H2$ domain, an IgG1 $C_H3$ domain, a drug selection cassette (e.g., a loxed resistance gene), and an IgG1 transmembrane domain, and a 3' homology arm containing sequences downstream with respect to the transmembrane domain. Upon homologous recombination at the locus and removal of the drug selection cassette (e.g., by Cre treatment), the endogenous IgG1 is replaced by an IgG1 that lacks a $C_H1$ domain (FIG. 3) (IgG1$\Delta C_H1$; I). In some embodiments, the structure of the resulting locus, which will express an IgG1 has a J region sequence fused to the hinge sequence.

A genetically modified non-human animal, e.g., mouse, lacking a nucleotide sequence encoding a $C_H1$ domain of an IgG1 and lacking a nucleotide sequence encoding a hinge region can be made by any method known in the art. For example, a targeting vector can be made that replaces the IgG1 gene with a truncated IgG1 lacking a sequence encoding a $C_H1$ domain and lacking a sequence encoding the hinge region. In another embodiment, a mouse genome is targeted by a targeting construct having a 5' (with respect to the direction of transcription of the genomic IgG1 gene) homology arm containing sequence upstream of the endogenous $C_H1$ domain, followed by nucleotide sequences that encode an IgG1 $C_H2$ domain, an IgG1 $C_H3$ domain, a drug selection cassette (e.g., a loxed resistance gene), and an IgG1 transmembrane domain, and a 3' homology arm containing sequences downstream with respect to the transmembrane domain. Upon homologous recombination at the locus and removal of the drug selection cassette (e.g., by Cre treatment), the endogenous IgG1 gene is replaced by an IgG1 gene that lacks a sequence encoding a $C_H1$ domain (FIG. 3) (IgG1$\Delta C_H1$ & hinge; II). In some embodiments, the structure of the resulting locus will express an IgG1 having a J region sequence fused to the $C_H2$ domain.

A genetically modified non-human animal, e.g., mouse, lacking an IgG1 $C_H1$ sequence (IgG1$\Delta C_H1$), or lacking an IgG1 $C_H1$ sequence and lacking a hinge (IgG1$\Delta C_H1$ & hinge), can be further modified to favor usage of the modified IgG1 isotype by deleting one or more other IgG isotypes, e.g., IgG2b and IgG2a/IgG2c, and or one or more other Ig isotypes, e.g., IgD, IgA, and/or IgE, by deleting or functionally disabling sequences encoding these isotypes. For example, a targeting construct is made having a 5' homology arm containing sequence upstream of the endogenous hinge region sequence (or upstream of the endogenous $C_H1$ domain sequence), sequences that encode the IgG1 $C_H2$ and $C_H3$ domains, a drug selection cassette followed by a sequence encoding the IgG1 transmembrane domain, followed by another drug selection cassette if desired, and a 3' homology arm containing sequences downstream with respect to the IgG2a/c gene. Upon homologous recombination at the locus and removal of the drug selection cassette(s) (e.g., by Cre treatment), the endogenous heavy chain constant locus contains only two IgG genes: an endogenous IgG3 and the IgG1$\Delta C_H1$ or IgG1$\Delta C_H1$ & hinge. (FIG. 3) (IgG1$\Delta C_H1 \Delta$IgG2b/2a; III or IgG1 $\Delta C_H1$ & hinge $\Delta$IgG2b/2a; IV).

Figure 3:
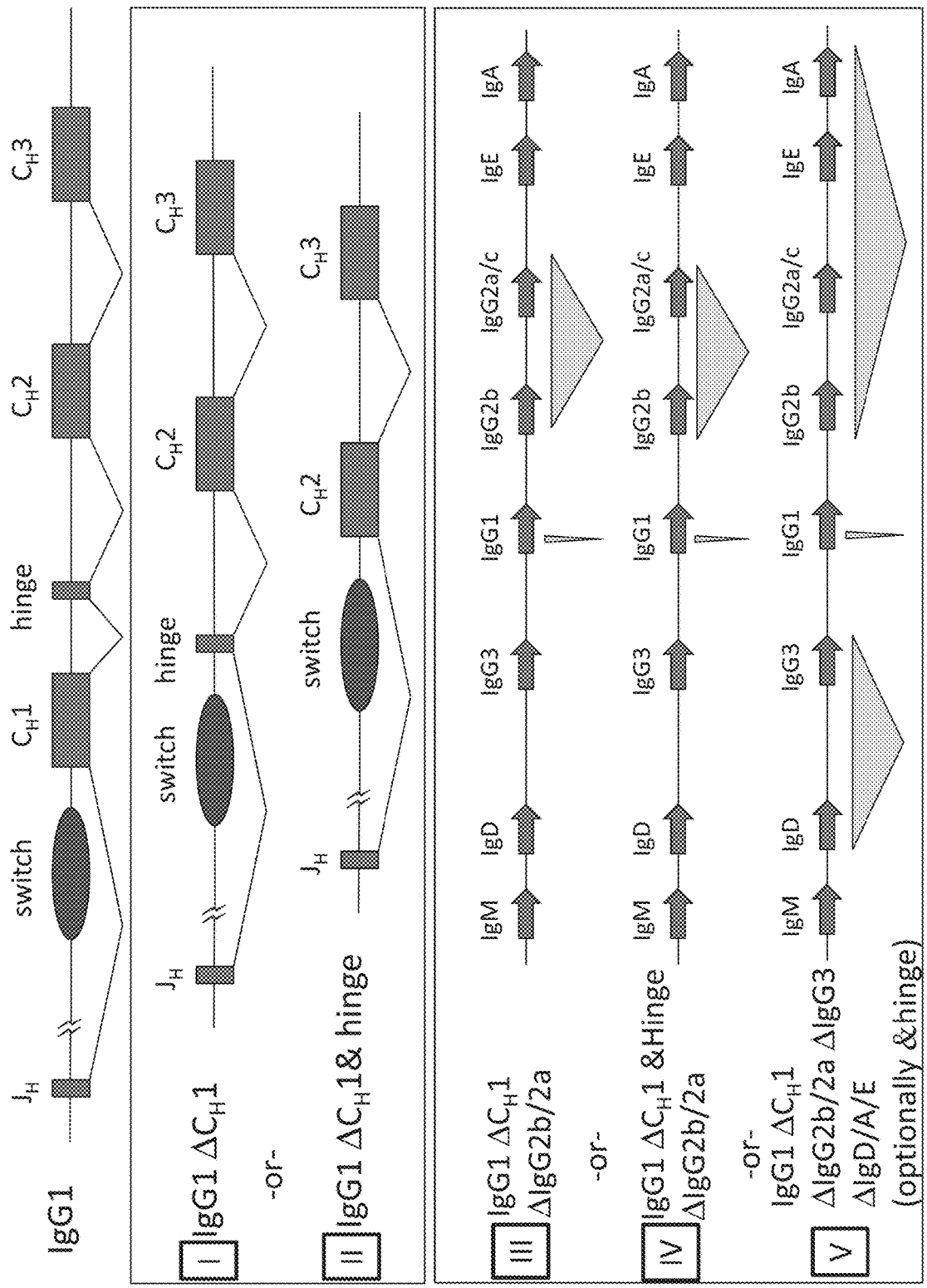
FIG. 3 illustrates a wild-type IgG1 locus in a mouse (IgG1, top), showing the $J_H$ region gene segment fused to a $C_H1$ gene segment, followed by a hinge region, a $C_H2$ gene segment, and a $C_H3$ gene segment; an IgG1 locus targeted with a construct that deletes a $C_H1$ domain (IgG1Δ$C_H1$; I); an IgG1 locus targeted with a construct that deletes both a $C_H1$ domain and a hinge region (IgG1Δ$C_H1$-Δhinge; II); a constant region locus targeted with a construct that deletes an IgG1 $C_H1$ domain, IgG2b and IgG2a (IgG1Δ$C_H1$ΔIgG2b/2a; III); a constant region locus targeted with a construct that deletes an IgG1 $C_H1$ domain, a hinge region, IgG2b and IgG2a (IgG1Δ$C_H1$ &Δhinge ΔIgG2b/2a; IV); or constant region locus targeted with a construct that deletes an IgG1 $C_H1$ domain, IgG2b, IgG2a, IgG3, IgD, IgA, and IgE, and optionally a hinge region (IgG1Δ$C_H1$ΔIgG2b/2a ΔIgG3 ΔIgD/A/E (optionally Δhinge); V). The schematic illustrations of the loci are not presented to scale. IgG2a/c designates either an IgG2a or IgG2c locus, as a mouse may have either an IgG2a allele or an IgG2c allele depending on its strain.
Figure 4C:
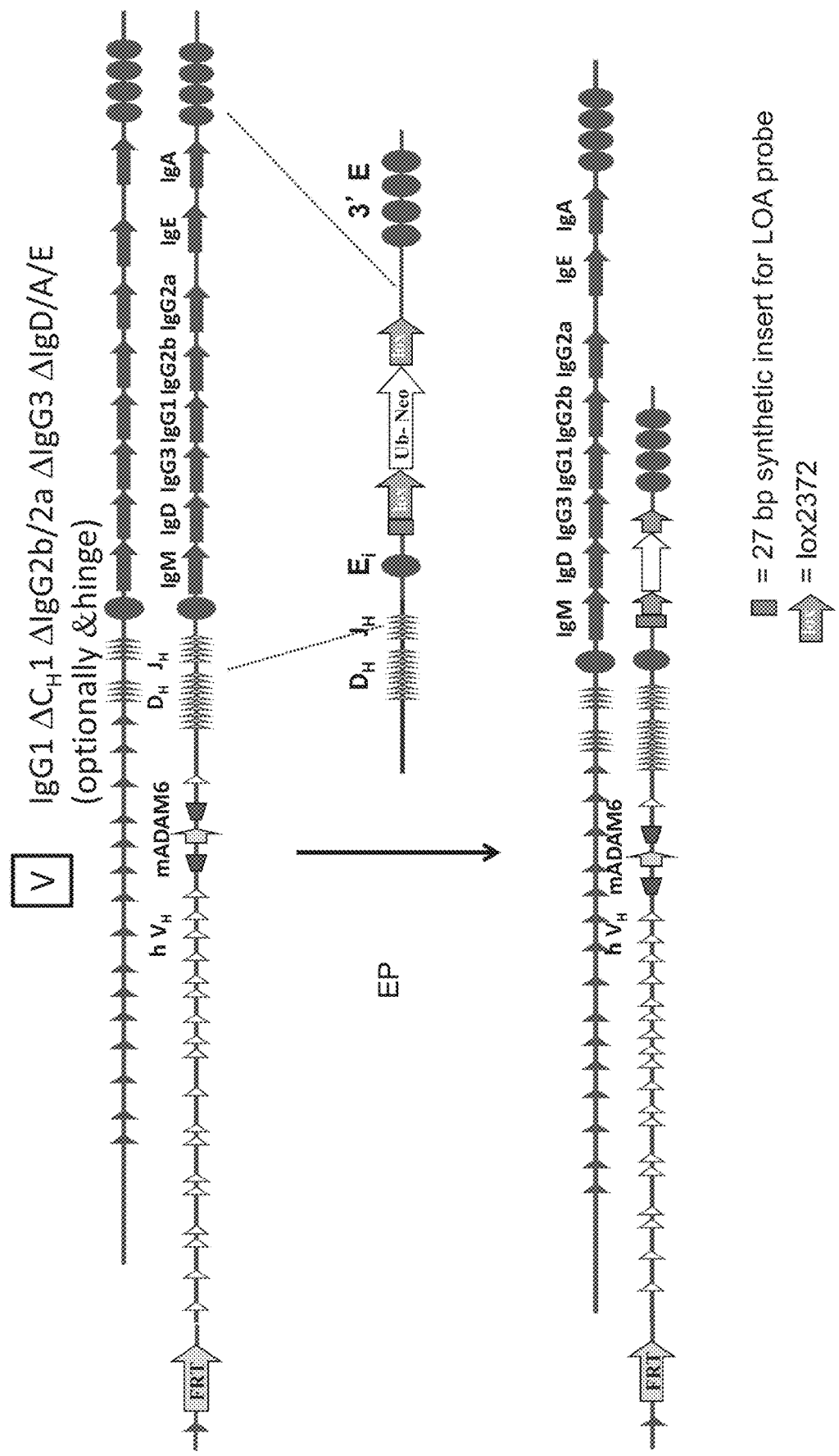
FIG. 4C illustrates targeting a mouse heavy chain constant region (not to scale) to make a genetically modified locus region lacking the IgM, IgD, IgG3, IgG1, IgG2b, IgG2a, IgE and IgA gene segments (first part of cloning IgG1Δ$C_H1$ΔIgG2b/IgG2a, ΔIgG3, ΔIgD/A/E continued in FIG. 4D). Human variable gene segments are indicated by empty triangles.
Figure 4D:
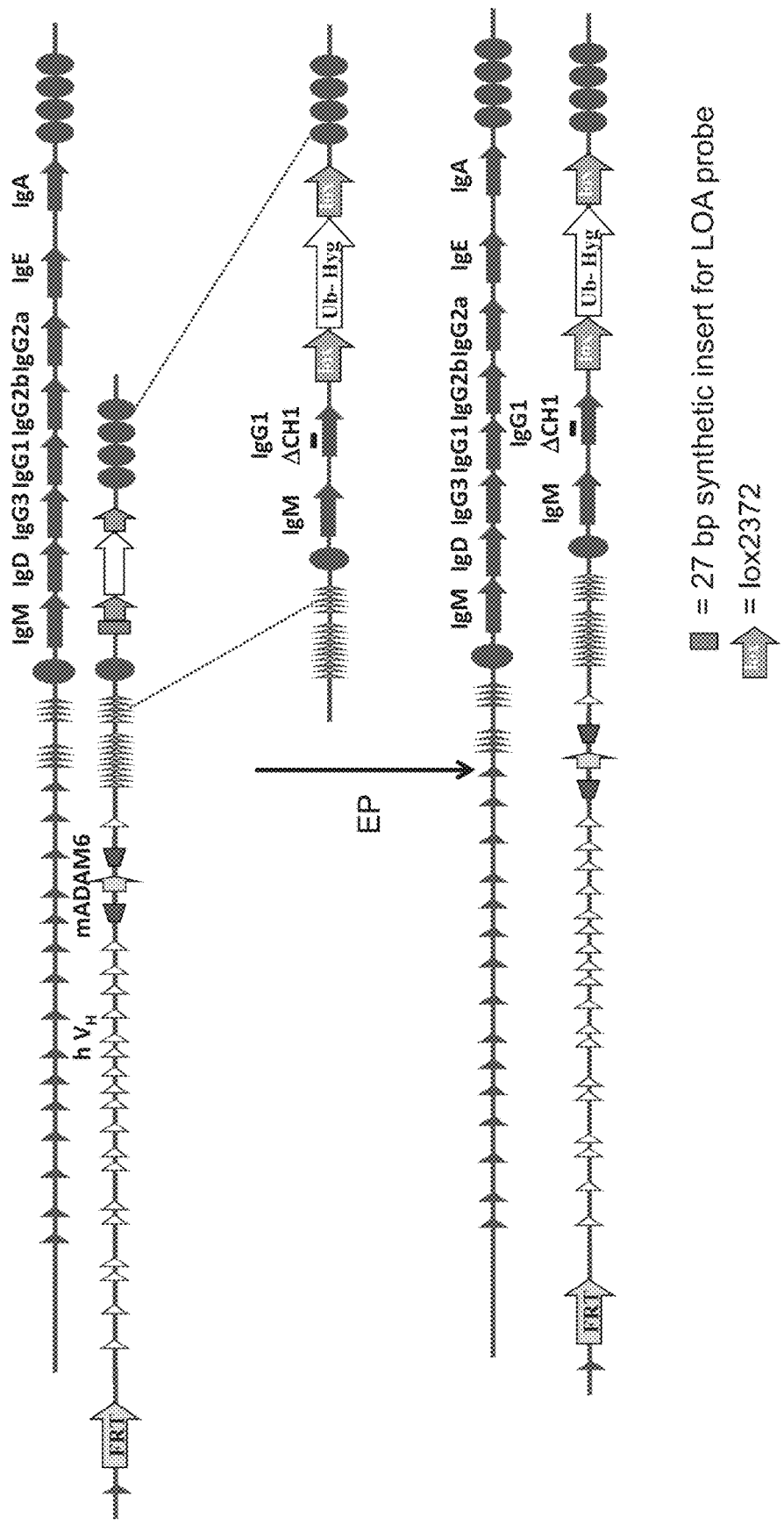
FIG. 4D illustrates targeting the mouse constant region of FIG. 4C to make a genetically modified locus (not to scale) that comprises human heavy chain variable gene segments, a complete and functional murine IgM gene region, and an IgG1 gene region lacking a functional $C_H1$ domain, and optionally, lacking a functional hinge region (the mouse also lacks IgG2b/IgG2a, IgG3, and IgD/A/E; in some embodiments referred to as 6180). Human variable gene segments are indicated by empty triangles.

An animal engineered as described above may be further modified to comprise a deletion or inactivating mutation in the IgG2a, IgG2b, IgG2c, IgG3, IgD, IgA, and/or IgE gene segments of a heavy chain locus. For example, a targeting vector can be made that deletes the constant region gene sequence of the heavy chain locus. In one example, a mouse genome is targeted by a targeting construct having a 5' (with respect to the direction of transcription of the genomic constant region gene sequence) homology arm containing sequence upstream of the endogenous IgM domain, followed by nucleotide sequences that encode a drug selection cassette (e.g., a loxed resistance gene) and a 3' homology arm containing sequence downstream of the IgA gene segment. Upon homologous recombination at the locus and removal of the drug selection cassette (e.g., by Cre treatment), the endogenous constant region is deleted and/or replaced with a selectable marker. (FIG. 4C). The animal may be further modified with a targeting vector can be made that reintroduces an IgM gene segment and an IgG1 gene that lacks a functional $C_H1$ domain sequence and optionally lacks a functional hinge region. (FIG. 4D). In one example, a genome of an animal is targeted by a targeting construct having a 5' homology arm containing sequence upstream of the selectable marker gene, followed by nucleotide sequences that encode a complete IgM constant region and an IgG1 constant region lacking a functional $C_H1$ domain, and optionally lacking a functional hinge, a drug selection cassette (e.g., a loxed resistance gene), and a 3' homology arm containing sequence downstream with respect to the selectable marker. Upon homologous recombination at the locus and removal of the drug selection cassette (e.g., by Cre treatment), an IgM gene segment and an IgG1 gene that lacks a functional $C_H1$ domain sequence and optionally lacks a functional hinge region is reintroduced. (FIG. 3) (IgG1 $\Delta C_H1$ $\Delta$IgG2b/2a$\Delta$IgG3$\Delta$IgD/A/E (optionally $\Delta$hinge); V). Other manipulations of endogenous immunoglobulin loci, e.g., deletions or inactivating mutations of CH1 region(s) of various non-IgM immunoglobulin isotypes are also provided.

In addition to genetic manipulation that introduces a deletion or inactivation into a $C_H1$ domain and, optionally a hinge, of a non-IgM immunoglobulin constant region by designing an appropriate constant region construct and introducing said construct into the locus by homologous recombination as described above, a deletion or an inactivation in a non-IgM $C_H1$ may be made by other methods known in the art, e.g., a conditional non-IgM $C_H1$ deletion that is induced in a mouse only upon antigen immunization, etc. Methods for conditional inactivation of loci are known in the art.

Genetic modification of the heavy chain locus as described above may further comprise replacement of one or more, substantially all, or all of the endogenous heavy chain variable gene segments, e.g., the $V_H$ gene segments, $D_H$ gene segments and/or $J_H$ gene segments with (a) human $V_H$ gene segments, $D_H$ gene segments and/or $J_H$ gene segments, which may be rearranged or capable of undergoing rearrangement to encode for binding proteins having human idiotypes, (b) light chain variable gene segments, e.g., light chain V gene segments and/or light chain J gene segments, which may be rearranged or capable of undergoing rearrangement to encode for immunoglobulin polypeptide chains having a light chain variable region linked to a heavy chain constant region lacking a functional $C_H1$ domain, e.g., $V_L$ single domain binding proteins, e.g., a single domain antigen binding protein comprising a light chain variable region, or (c) human light chain variable gene segments, e.g., human light chain V gene segments and/or human light chain J gene segments, which may be rearranged or capable of undergoing rearrangement to encode for immunoglobulin polypeptide chains having a human light chain variable region linked to a heavy chain constant region lacking a functional $C_H1$ domain, e.g., $V_L$ single domain binding proteins, e.g., a single domain antigen binding protein comprising a human light chain variable region having human idiotypes.

Figure 14A:
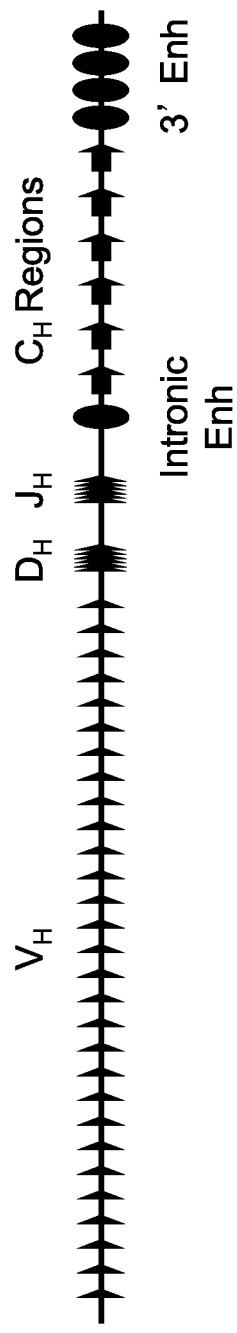
FIG. 14A illustrates a schematic of the mouse heavy chain locus (not to scale). The mouse heavy chain locus is about 3 Mb in length and contains approximately 200 heavy chain variable (V$_H$) gene segments, 13 heavy chain diversity (D$_H$) gene segments and 4 heavy chain joining (J$_H$) gene segments as well as enhancers (Enh) and heavy chain constant (CH) regions.

A schematic illustration (not to scale) of a mouse heavy chain and a human κ light chain loci is provided in FIG. 14 to show the approximately 200 heavy chain variable ($V_H$) gene segments, 13 heavy chain diversity ($D_H$) gene segments and 4 heavy chain joining ($J_H$) gene segments as well as enhancers (Enh) and heavy chain constant ($C_H$) regions of the mouse locus, and the about 76 Vκ gene segments, 5 Jκ gene segments, an intronic enhancer (Enh) and a single constant region (Cκ) of the human κ locus.

Figure 15:
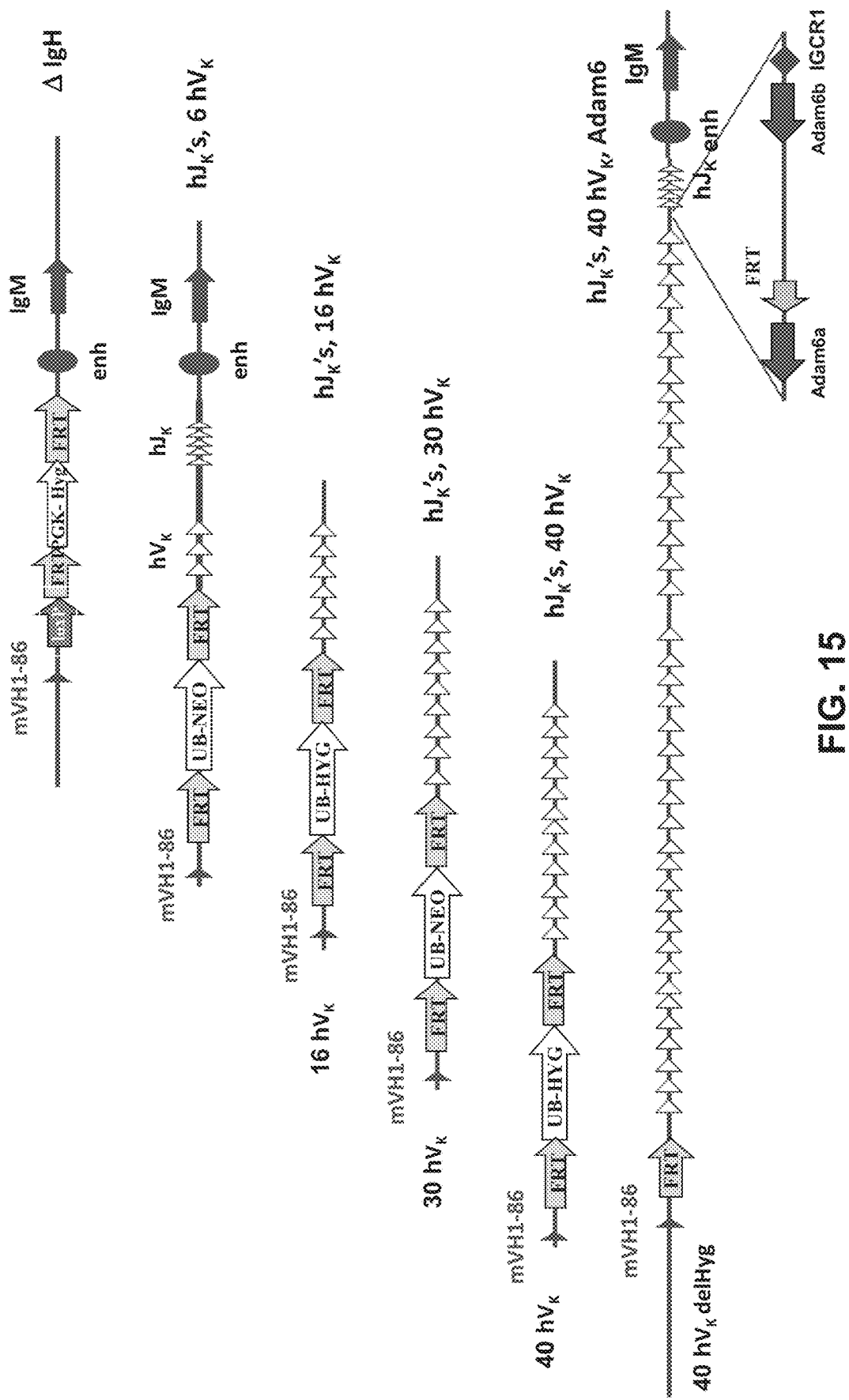
FIG. 15 shows a targeting strategy (not to scale) for progressive insertion of 40 human Vκ and 5 human Jκ gene segments into a mouse heavy chain locus in which endogenous heavy chain variable region gene segments have been deleted. Hygromycin (HYG) and Neomycin (NEO) selection cassettes are shown with recombinase recognition sites (FRT). Also shown is a targeting strategy (not to scale) for the insertion of the Adam6a, Adam6b and IGCR1 genes. Human variable gene segments are indicated by empty triangles.

Shown in FIG. 15 is a schematic illustration (not to scale) for inserting human κ gene segments into a murine heavy chain locus, which was modified by homologous recombination to inactivate the endogenous mouse heavy chain locus through targeted deletion of $mV_H$, $mD_H$ and $mJ_H$ gene segments. As shown in FIG. 15, four separate targeting vectors may be used to progressively insert human Vκ gene segments and human Jκ gene segments into the inactivated mouse heavy chain locus using standard molecular techniques recognized in the art. The human κ gene segments used for engineering the four targeting constructs may be naturally found in proximal contig of the germline human κ light chain locus.

A genetically modified mouse comprising a genetically engineered rearranged light chain can be made by any method known in the art. For example, a targeting vector can be made that replaces either the endogenous unrearranged light chain variable V and J gene segments of an endogenous light chain locus with a single rearranged V:J gene, or the entire unrearranged light chain locus with a genetically engineered light chain locus comprising a single rearranged V:J gene operably linked to a light chain constant region.

In another aspect, a non-human animal as described herein is further engineered to comprise an ectopic nucleotide sequence encoding ADAM 6 (ADAM6a and/or ADAM6b), a functional fragment, homolog or ortholog thereof. In some embodiments, a heavy chain locus of a non-human animal described herein is further engineered to comprise an ectopic nucleotide sequence encoding a mouse ADAM6 (ADAM6a and/or ADAM6b), a functional fragment, homolog or ortholog thereof. In various embodiments, the ADAM6 protein is functional in a non-human male animal. Methods and compositions for engineering such non-human animals are described, e.g., in U.S. Pat. No. 8,642,835, which is incorporated herein by reference.

In some embodiments, genetically modified animal as described above, and others, are made by introducing a suitable targeting construct into a suitable ES cell (in one or more independent targetings), and positive clones comprising a marker or selection cassette of the targeting construct are identified and grown. Clones are then employed as donor ES cells in a host embryo under conditions suitable for making a chimeric animal or a fully ES cell-derived animal. The marker or selection cassette can be optionally removed, either at the ES cell stage or in the chimeric or ES cell-derived mouse, e.g., by employing a loxed cassette and breeding to a Cre-containing strain, or by electroporating the ES cell with a Cre expression vector. Accordingly, in some embodiments, the genetic modification occurs in the germline of the animal.

In some embodiments, the method of making an animal as disclosed herein comprises crossing a first animal capable of producing a single domain antigen binding protein, e.g. a first animal comprising in its germline an IgG heavy chain locus lacking a functional $C_H1$ domain, with a second animal capable of producing a genetically engineered rearranged light chain, e.g., a second animal comprising in its germline a genetically engineered light chain locus having a single rearranged V:J variable region operably linked to a light chain constant region, to produce an F1 genetically engineered animal, wherein the F1 animal comprises the IgG heavy chain locus of the first animal and the light chain locus of the second animal. The crossing may be done by animal breeding or by otherwise combining gametes, including in vitro manipulations.

For the non-human animals where suitable genetically modifiable ES cells are not readily available, methods distinct from those described herein are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

Making Single Domain Antigen Binding Proteins

Once a genetically engineered animal capable of producing single domain antigen binding proteins and/or a genetically engineered single rearranged light chain is obtained, immunoglobulins and binding protein preparations against an antigen can be readily obtained by immunizing the animal with the antigen. "Polyclonal antisera composition" as used herein includes affinity purified polyclonal binding protein preparations.

In one aspect, a method for making a binding protein that lacks a $C_H1$ domain is provided, comprising: (a) immunizing a non-human animal as described herein with an antigen; (b) maintaining the non-human animal under conditions sufficient for the non-human animal to make a binding protein; (c) identifying a binding protein made by the mouse that lacks a functional $C_H1$ domain and/or that lacks a functional hinge region; and, (d) isolating from the non-human animal the binding protein, a cell that makes the binding protein, or a nucleotide sequence that encodes a sequence of the binding protein.

A variety of antigens can be used to immunize a transgenic animal. Such antigens include but are not limited to, cellular proteins, microorganisms, e.g. viruses and unicellular organisms (such as bacteria and fungi), alive, attenuated or dead, fragments of the microorganisms, or antigenic molecules isolated from the microorganisms.

The antigens can be administered to a transgenic animal in any convenient manner, with or without an adjuvant, and can be administered in accordance with a predetermined schedule.

For making a monoclonal binding protein, spleen cells are isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", J Immunol Methods 242:159 (2000), and by Burton, D. R., "Phage display", Immunotechnology 1:87 (1995).

Once monoclonal single domain antigen binding proteins have been generated, such binding proteins can be easily converted into fully human binding proteins using standard molecular biology techniques, if desired. Fully human monoclonal binding proteins are not immunogenic in humans and are appropriate for use in the therapeutic treatment of human subjects.

Thus, in one embodiment, wherein the single domain antigen binding protein comprises a human $V_H$ or a human $V_L$ region and a mouse heavy chain constant region comprising a deletion or an inactivating mutation in a non-IgM $C_H1$ domain, the sequence of $V_H$ or $V_L$ domain of the single domain antigen binding protein can be cloned upstream of a human constant region, optionally lacking a $C_H1$ domain in a suitable expression vector resulting in an expression construct encoding fully human single domain antigen binding protein that can be expressed in a suitable cell, e.g., cell typically for antibody expression, e.g., eukaryotic cell, e.g., a CHO cell.

Accordingly, also provided herein are monoclonal binding protein producing cells derived from animals genetically modified as disclosed herein, as well as nucleic acids derived therefrom. Also provided are hybridomas derived therefrom. Also provided are fully human single domain binding proteins, as well as encoding nucleic acids, derived therefrom.

Single domain antigen binding proteins described herein may also be used to make bispecific antibodies. An advantage of single domain antigen binding proteins described herein is the ability to make bispecific antibodies by heterodimerizing heavy chains with specificity for two different epitopes in a single therapeutics.

EXAMPLES

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. The Examples do not include detailed descriptions of conventional methods that would be well known to those of ordinary skill in the art (molecular cloning techniques, etc.).

Example 1

Mice Encoding a $V_H$ Single Domain Binding Protein: Mice Comprising Immunoglobulin Chain Having a Heavy Chain Variable Region and a Heavy Chain Constant Region Lacking a Functional $C_H1$ Domain, and Comprising a Single Rearranged Light Chain (ULC)

Example 1.1

Generation of Animals

Mice genetically modified to comprise a heavy chain locus comprising a complete and functional IgM gene sequence and an IgG1 gene sequence that lacks a functional $C_H1$ gene sequence, and optionally lacks a functional hinge region (FIG. 1A), were made according to the methods described in US2011/0145937, Macdonald et al., which is incorporated herein by reference. Several versions of mice that lacked various combinations of heavy chain constant gene sequences and contained deletion of $C_H1$ domain(s) but comprised a complete and functional IgM were made (FIG. 3). For example, mice homozygous for a heavy chain locus comprising mouse heavy chain variable gene segments and a complete and functional IgM gene sequence and an IgG1 gene sequence that lacks a functional $C_H1$ gene sequence and hinge region (m$V_H$IgG1Δ$C_H1$ & hinge; 1576 HO, "II" in FIGS. 3 and 4B) were made. Additionally, mice homozygous for a heavy chain locus comprising human heavy chain variable gene segments and a complete and functional IgM gene sequence, an IgG1 gene sequence that lacks a functional $C_H1$ gene sequence and hinge region, and lacking the IgG2b and IgG2a gene sequences (h$V_H$IgG1Δ$C_H1$ & hingeΔIgG2b/2a; 1859 HO, see, e.g., "IV" in FIG. 3) were made. Additionally, mice homozygous for a heavy chain locus comprising human heavy chain variable gene segments and a complete and functional IgM gene sequence, an IgG1 gene sequence that lacks a functional $C_H1$ gene sequence, and lacking the IgG2b and IgG2a gene sequences (h$V_H$IgG1Δ$C_H1$ΔIgG2b/2a; 1673 HO, see, e.g., "III" in FIGS. 3 and 4A) were made. Additionally, mice homozygous for a heavy chain locus comprising human heavy chain variable gene segments and a complete and functional IgM gene sequence, an IgG1 gene sequence that lacks a functional $C_H1$, and lacking IgD, IgG2a, IgG2b, IgG3, IgE, and IgA gene sequences (h$V_H$IgG1Δ$C_H1$ΔIgG2b/2aΔIgG3ΔIgD/A/E; 6180 HO, see "V" in FIGS. 3 and 4C-D) were made. Additional exemplary versions of modification in the heavy chain constant region are presented in FIG. 3. Other variations of combinations of $C_H1$ deletions/inactivations and/or immunoglobulin constant gene deletions/inactivations are made, e.g., a mouse is made wherein both IgG1 and IgG2a comprise $C_H1$ domain deletions, and the mouse also comprises a deletion of IgD, IgE, IgG3, and IgG2b. As shown in FIG. 4, heavy chain loci may also be modified to comprise human variable regions, which may be human heavy chain variable regions [or human light chain variable regions (FIG. 16, see Examples 2 and 3 below)]. Heavy chain loci may also be modified to comprise an Adam 6a gene, an Adam 6b gene, or both, or a fragment of the gene, wherein the gene or the fragment thereof is functional in a male mouse (see, e.g., U.S. 2012/0322108, incorporated herein by reference).

Generation of a common light chain mouse (also referred to as universal light chain or ULC mice) comprising a single rearranged variable gene sequence V:J (e.g., Vκ1-39Jκ5 or Vκ3-20Jκ1 common light chain mouse) and generation of antigen-specific antibodies in those mice is described in, e.g., U.S. patent application Ser. Nos. 13/022,759, 13/093, 156, 13/412,936, 13/488,628, 13/798,310, and 13/948,818 (Publication Nos. 2011/0195454, 2012/0021409, 2012/ 0192300, 2013/0045492, US20130185821, and US20130302836 respectively), each of which is incorporated herein by reference in its entirety. Specifically, mice that express the genetically engineered Vκ1-39Jκ5 kappa light chain (1633 HO or 1634 HO) or the genetically engineered Vκ3-20Jκ1 kappa light chain (1635 HO or 1636 HO) in their germline were made.

VELOCIMMUNE® mice containing a single rearranged human germline light chain region (ULC Vκ1-39Jκ5; 1633 or 1634) or (ULC Vκ3-20Jκ1; 1635 or 1636) are bred to mice carrying a modified IgG constant region. Specifically, such ULC mice were bred to mice having a murine heavy chain variable region operably linked to a murine heavy chain constant region wherein the IgG1 $C_H1$ and IgG1 hinge regions were deleted or inactivated (mV$_H$IgG1ΔC$_H$1 & hinge, 1576), mice having a human heavy chain variable region operably linked to a murine heavy chain constant region wherein the IgG1 $C_H1$ and IgG1 hinge regions, and the IgG2a and IgG2b genes were deleted or inactivated (hV$_H$ IgG1ΔC$_H$1 & hingeΔIgG2b/2a; 1859), mice having a human heavy chain variable region operably linked to a murine heavy chain constant region wherein the IgG1 $C_H1$ regions, and the IgG2a and IgG2b genes were deleted or inactivated (hV$_H$ IgG1ΔC$_H$1ΔIgG2b/2a; 1673), or mice having a human heavy chain variable region operably linked to a murine heavy chain constant region wherein the IgG1 $C_H1$ regions, and the IgG2a and IgG2b, IgD, IgG3, IgA, and IgE genes were deleted or inactivated (hV$_H$ IgG1ΔC$_H$1ΔIgG2b/ 2aΔIgG3ΔIgD/A/E; 6180), to obtain the following progeny mice:

mV$_H$IgG1ΔC$_H$1 & hingexVκ3-20Jκ1 ULC or mV$_H$IgG1ΔC$_H$1 & hingexVκ1-39Jκ5 ULC homozygous mice (1576HO 1635HO or 1576 HO 1633 HO), hV$_H$ IgG1ΔC$_H$1 & hingeΔIgG2b/2axVκ3-20Jκ1 ULC or hV$_H$ IgG1ΔC$_H$1 & hingeΔIgG2b/2axVκ1-39Jκ5 ULC homozygous mice (1859 HO 1635 HO or 1859HO 1633HO), hV$_H$ IgG1ΔC$_H$1ΔIgG2b/2axVκ3-20Jκ1 ULC or hV$_H$ IgG1ΔC$_H$1ΔIgG2b/2axVκ1-39Jκ5 ULC homozygous mice (1673HO 1635 HO or 1673 HO 1633 HO), and hV$_H$IgG1ΔC$_H$1 & hingeΔIgG2a/2bΔIgG3ΔIgD/A/Ex Vκ3-20Jκ1 ULC or hV$_H$IgG1ΔC$_H$1 & hingeΔIgG2a/ 2bΔIgG3ΔIgD/A/ExVκ1-39Jκ5 ULC homozygous mice (6180 HO 1635 HO or 6180 HO 1634 HO).

Other versions of the mice comprising a deletion or inactivating mutation in a $C_H1$ domain and a deletion or inactivating mutation in an immunoglobulin constant region gene are bred to mice containing a single rearranged human germline light chain region as described above.

Example 1.2

Immunization of Mice with Antigen and Expression of Single Domain Binding Proteins Mice homozygous for modifications were immunized with different antigens and boosted by various routes using a variety of adjuvants. Titers for IgG1 specific responses were evaluated by ELISA or western blot.

Figures 5A, 5B:
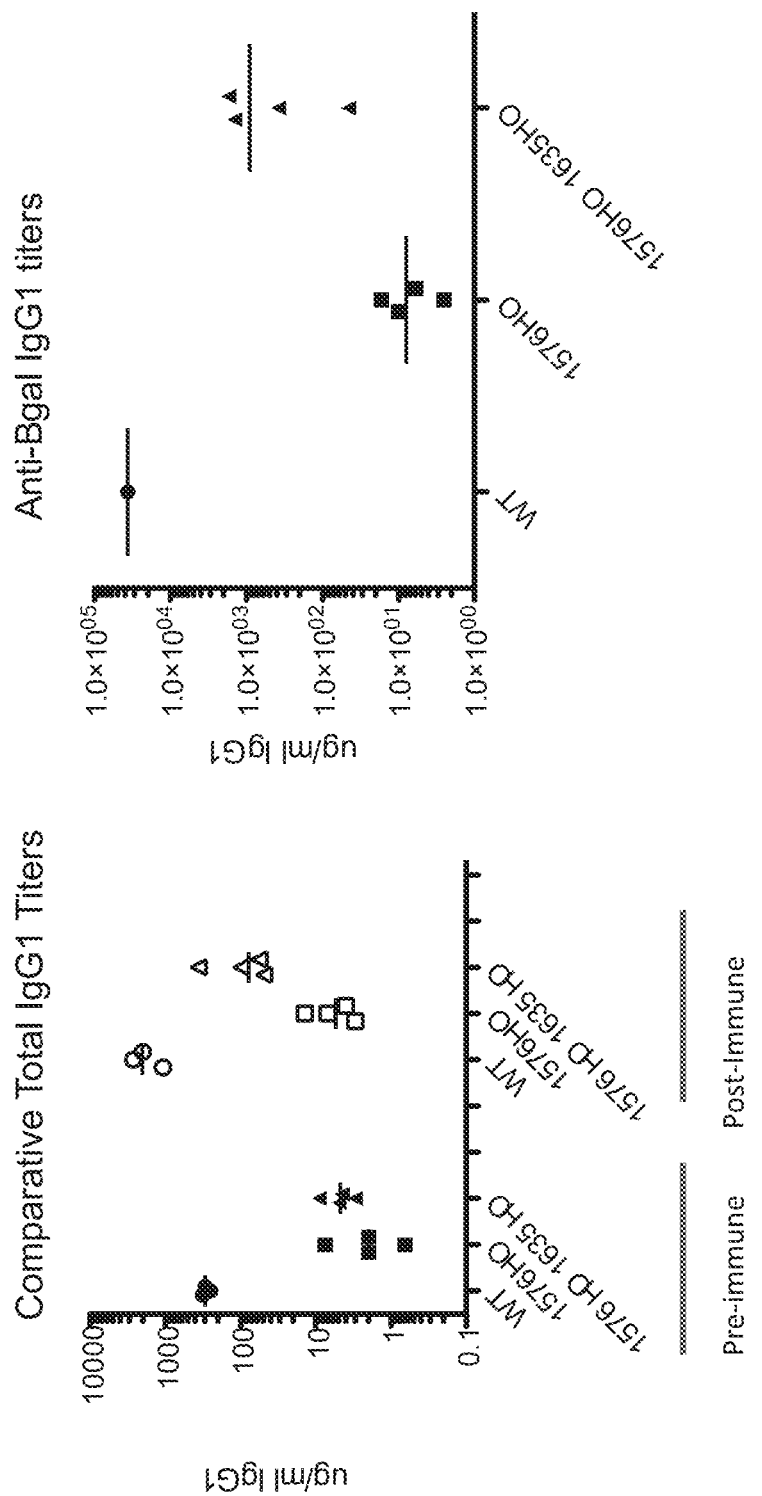
FIG. 5A shows comparative total serum IgG1 titers between various single domain IgG1 mice, before and after immunization with β-galactosidase (βgal): mice homozygous for mV$_H$IgG1Δ$C_H1$ & hinge with mouse kappa chain (1576); mice homozygous for mV$_H$IgG1Δ$C_H1$ & hinge with a kappa chain that is a single rearranged light chain Vκ3-20Jκ1 ULC (1576/1635); or wild-type (WT) mouse with same genetic background. HO is homozygous for genetic modification.
FIG. 5B illustrates antigen specific IgG1 serum titers in immunized WT mice compared to mV$_H$IgG1Δ$C_H1$ & hinge homozygous mice (1576HO) or mV$_H$IgG1Δ$C_H1$-hinge× Vκ3-20Jκ1 ULC1 homozygous mice (1576HO 1635HO). Mice were immunized with β-galactosidase (βgal) as a model antigen, antigen specific IgG1 titers were measured by ELISA.

As shown in FIG. 5A, mice homozygous for both IgG1 ΔC$_H$1/hinge and ULC modifications exhibit increased expression of total amount of IgG1 in the serum both before and after immunization, compared to a mouse having IgG1 ΔC$_H$1 alone. The higher titers in ΔC$_H$1/hingexULC mice suggest that presence of universal light chain increases the likelihood of generating an antigen specific single domain antigen binding protein. FIG. 5B.

Figure 7:
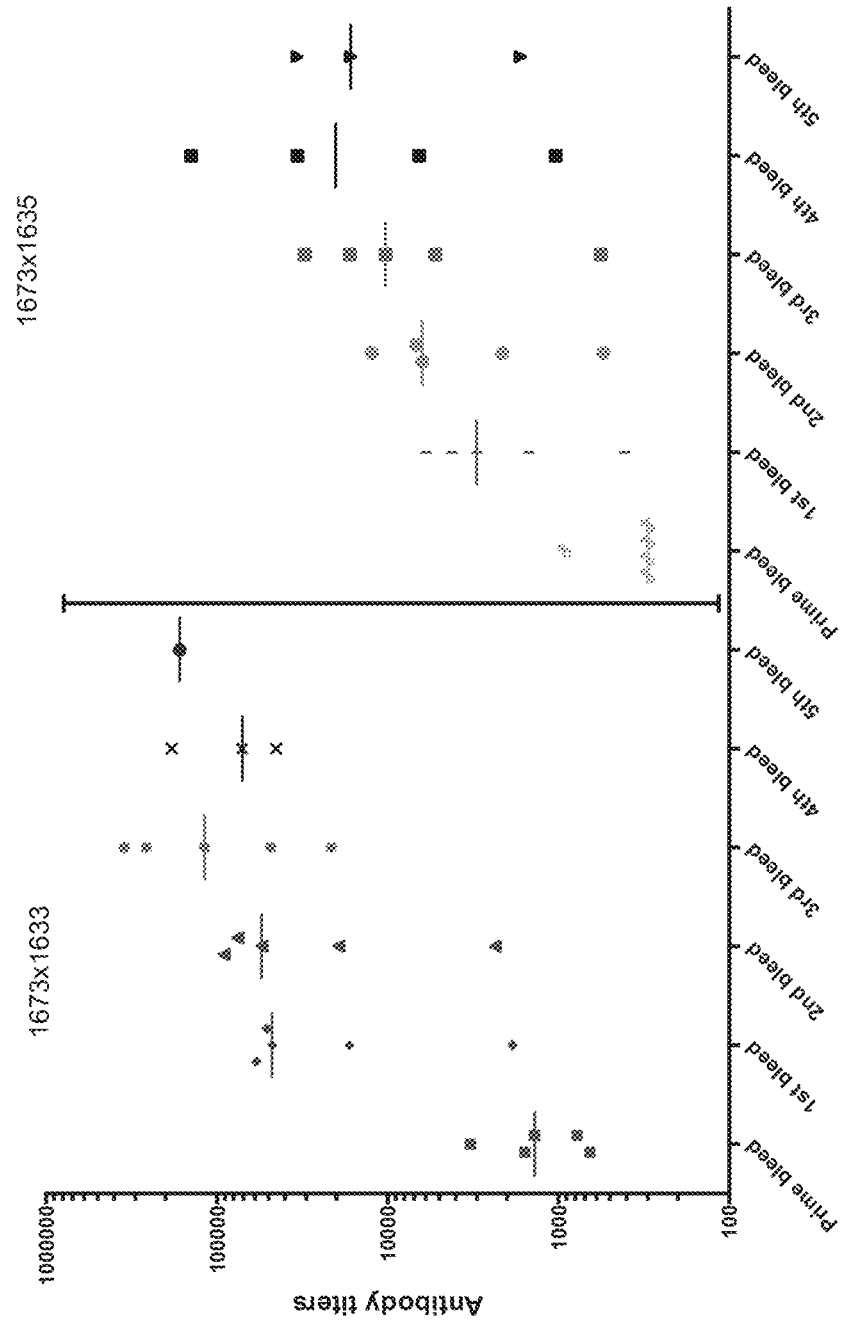
FIG. 7 shows IgG1 titers (y-axis) found in the plasma of animals at different timepoints (x-axis) after intraperitoneal immunization with Antigen X, a cell surface protein, of hV$_H$IgG1ΔC$_H$1ΔIgG2b/2a×Vκ1-39Jκ5 homozygous mice (1673×1633) or hV$_H$IgG1ΔC$_H$1ΔIgG2b/2a×Vκ3-20Jκ1 homozygous mice (1673×1635).

FIG. 7 demonstrates that high titers may be obtained with various versions of mice genetically engineered to comprise ΔC$_H$1 and ULC modifications.

Figure 6:
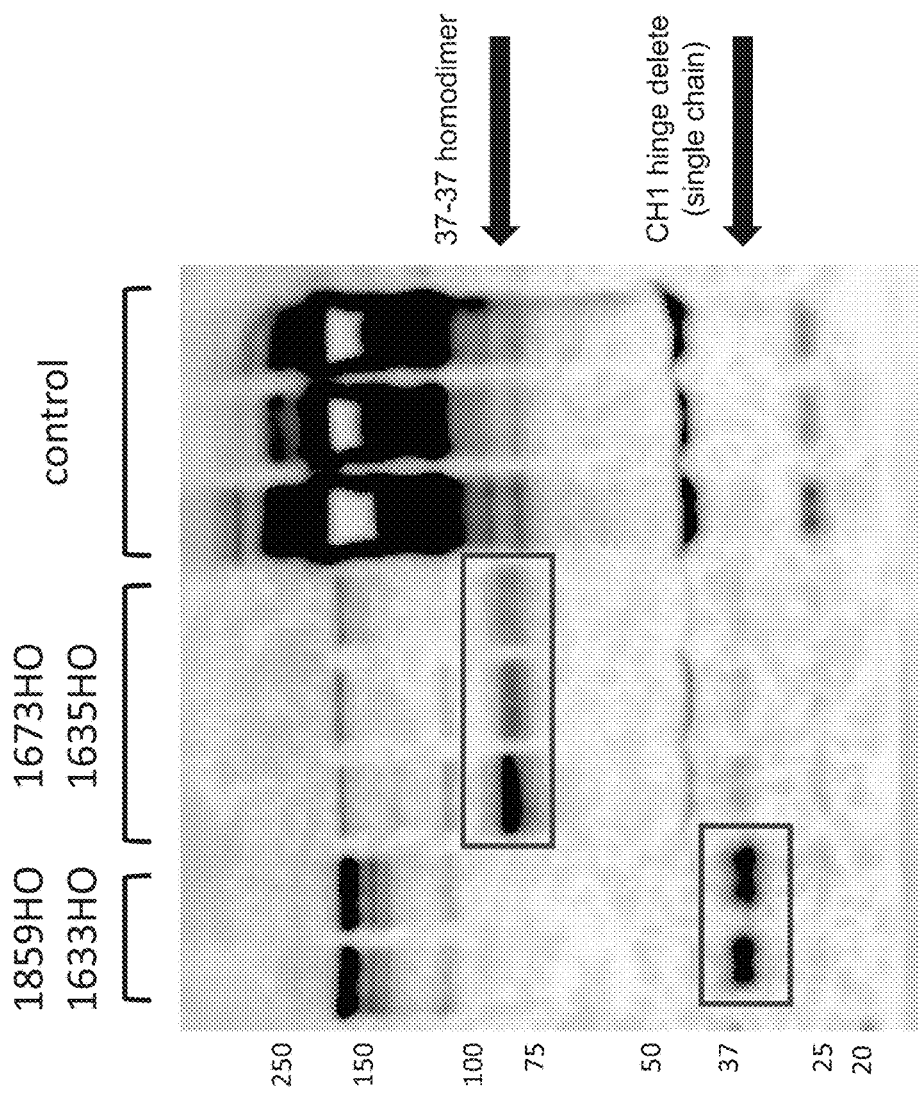
FIG. 6 provides an image of a Western blot, prepared under non-reducing conditions and visualized with anti-mouse IgG, of mouse sera from two hV$_H$IgG1Δ$C_H$1 & hingeΔIgG2b/2a×Vκ1-39Jκ5 ULC homozygous mice (1859HO 1633HO), three hV$_H$IgG1Δ$C_H$1ΔIgG2b/2a×Vκ3-20Jκ1 ULC homozygous mice (1673HO 1635 HO) and three VELOCIMMUNE® control mice (VI3 IgG1) having human variable regions ($V_H$ and Vκ) with mouse constant regions of dimeric single domain antigen binding proteins (37-37 homodimer) or monomeric Δ$C_H$1 single domain binding proteins ($C_H$1 hinge delete single chain).
Figure 8:
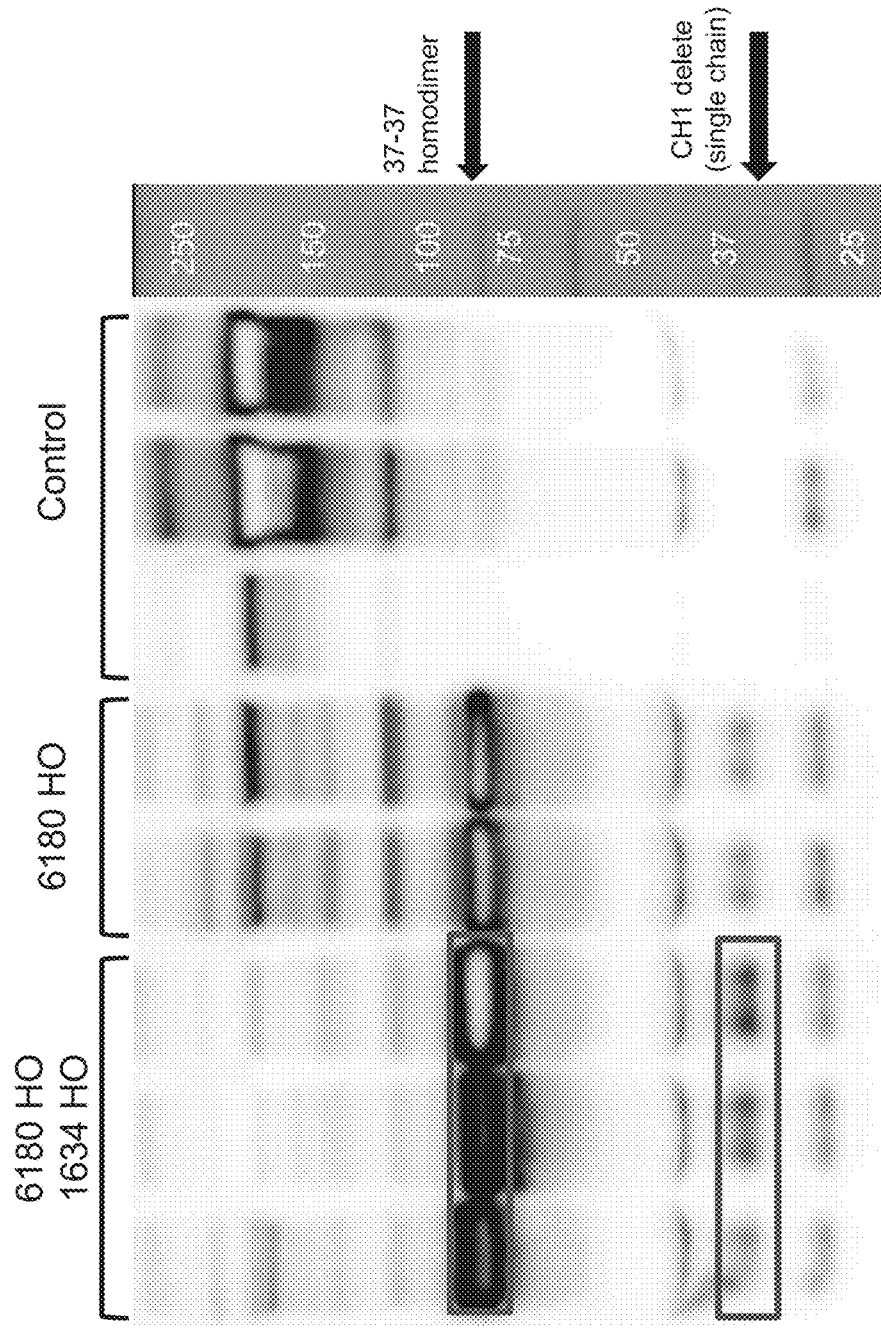
FIG. 8 provides an image of a Western blot, prepared under non-reducing conditions and visualized with anti-mouse IgG, of mouse sera from three hV$_H$IgG1ΔC$_H$1ΔIgG2b/2a ΔIgG3 ΔIgD/A/E×Vκ1-39Jκ5 ULC homozygous mice (6180HO 1634 HO), two hV$_H$IgG1ΔC$_H$1ΔIgG2b/2a ΔIgG3 ΔIgD/A/E homozygous mice (6180 HO) and three VI3 control mice having human variable regions (V$_H$ and Vκ) with mouse constant regions of dimeric single domain antigen binding proteins (37-37 homodimer) or monomeric ΔC$_H$1 single domain binding proteins (C$_H$1 delete single chain).

Additionally, FIGS. 6 and 8 show that single domain antigen-binding proteins are present and may be isolated from mice comprising both human heavy chain variable region with a deletion in a $C_H1$ region and a single rearranged light chain (universal light chain).

Example 1.3

B Cell Development and Maturation in Mice Expressing Single Domain Binding Proteins and a Single Rearranged Light Chain (ULC)

B cell contents of the spleen, blood and bone marrow compartments from mice homozygous for a modified $C_H1$ domain and a single rearranged light chain (ULC) (see FIG. 2) were analyzed for progression through B cell development and B cell maturation using flow cytometry of various cell surface markers as indicated herein.

Briefly, ULC mice and mice homozygous a modified $C_H1$ domain and a rearranged light chain were sacrificed and blood, spleens and bone marrow were harvested. Blood was collected into microtainer tubes with EDTA (BD Biosciences). Bone marrow was collected from femurs by flushing with complete RPMI medium (RPMI medium supplemented with fetal calf serum, sodium pyruvate, Hepes, 2-mercaptoethanol, non-essential amino acids, and gentamycin). RBCs from spleen and bone marrow preparations were lysed with ACK lysis buffer (Lonza Walkersville), followed by washing with complete RPMI medium.

Cells ($1\times10^6$) were incubated with anti-mouse CD16/ CD32 (2.4G2, BD) on ice for ten minutes, followed by labeling with the following antibodies for thirty minutes on ice: APC-H7 conjugated anti-mouse CD19 (clone 1 D3, BD), Pacific Blue conjugated anti-mouse CD3 (clone 17A2, BIOLEGEND®), PeCy7-IgM (II/41, EBIOSCIENCE®), PerCP-Cy5.5-IgD (11-26c.2a, BIOLEGEND®), APC-eFluor 780-B220 (RA3-6B2, EBIOSCIENCE®), APC-CD19 (MB19-1, EBIOSCIENCE®), PE-CD93 (AA4.1, BIOLEGEND®), FITC-CD23 (B3B4, BD), APC-CD21/ CD35 (7G6, BD). Bone marrow: immature B cells (B220$^{int}$IgM$^+$), mature B cells (B220$^{hi}$IgM$^+$). Blood and spleen: B cells (CD19$^+$), mature B cells (CD19$^+$IgM$^{int}$Ig-D$^{hi}$), transitional/immature B cells (CD19$^+$IgM$^{hi}$IgD$^{int}$).

Figure 9:
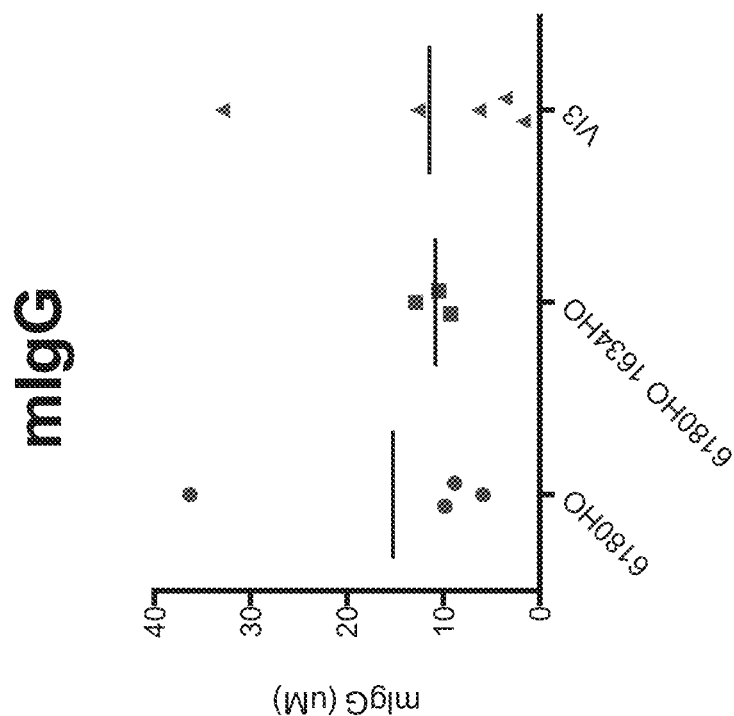
FIG. 9 shows the concentration of steady state IgM and IgG in the plasma of hV$_H$IgG1ΔC$_H$1ΔIgG2a/2bΔIgG3ΔIgD/A/E×Vκ1-39Jκ5 (6180 HO×1634 HO) mice and hV$_H$IgG1ΔC$_H$1ΔIgG2a/2bΔIgG3ΔIgD/A/E (6180 HO) and VI3 control animals.
Figure 9:
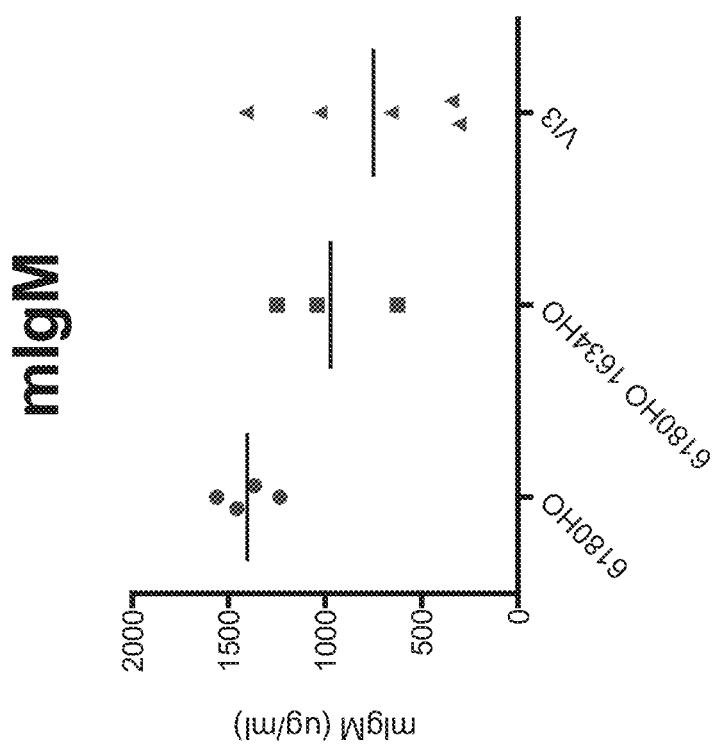
Figure 10B:
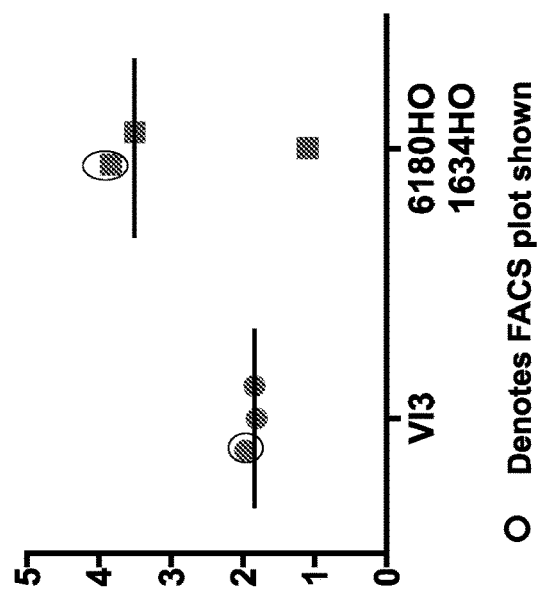
FIG. 10A, FIG. 10B, and FIG. 10C shows contour plots of splenocytes gated on singlets stained for CD19 and CD3 from a representative homozygous control VI3 and hV$_H$IgG1ΔC$_H$1ΔIgG2a/2bΔIgG3ΔIgD/A/E (6180 HO)× Vκ1-39Jκ5 (6180 HO 1634 HO) mouse (FIG. 10A). Also shown are contour plots of splenocytes gated on CD19+ B cells stained for immunoglobulin D (IgD) and immunoglobulin M (IgM) from a representative control VI3 mouse and a representative homozygous hV$_H$IgG1ΔC$_H$1ΔIgG2a/2bΔIgG3ΔIgD/A/E×Vκ1-39Jκ5 (6180 HO×1634 HO) mouse (FIG. 10C). Notably, the B cells are IgD− as the IgD constant domain was deleted. Therefore, the term "mature" in this plot is merely an indication of the absence of IgD and not other non-IgM immunoglobulins. Also provided is a graph showing the total number of CD19$^+$ B cells (y-axis; cells/spleen×10$^7$) of three representative mice from each group (FIG. 10B). The animal for which the contour plots are included is encircled.
Figure 10A:
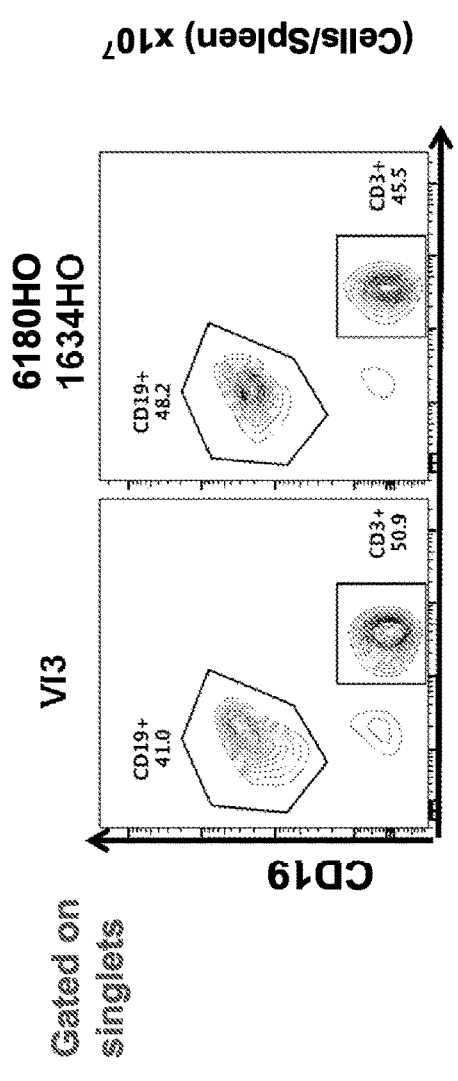
Figure 10C:
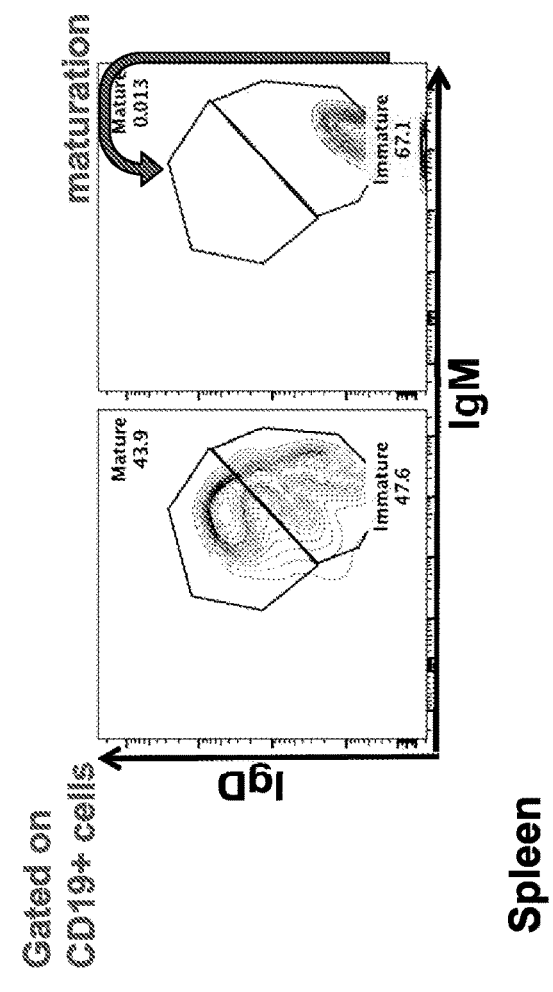
Figures 11A, 11B, 11C:
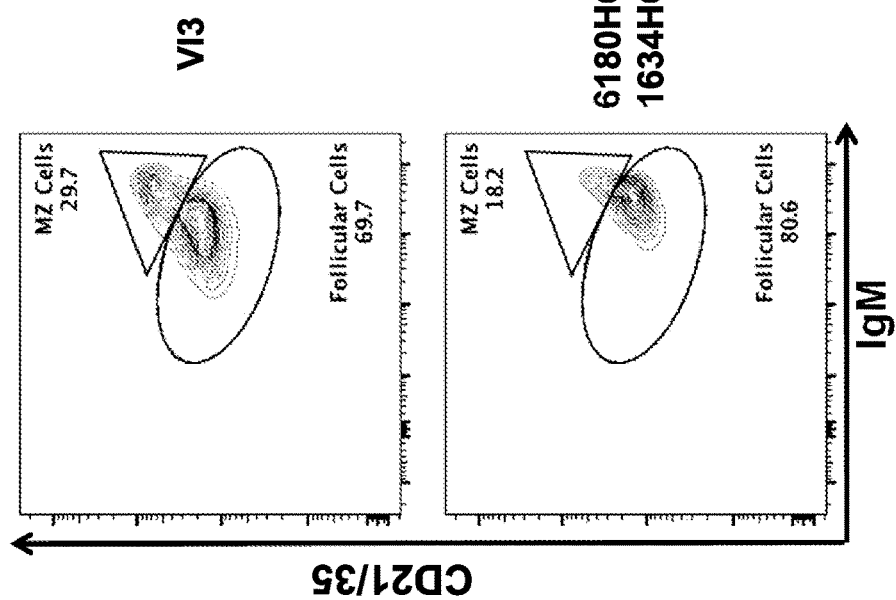
FIG. 11A, FIG. 11B, and FIG. 11C shows contour plots of (FIG. 11A) CD19+ gated B cells isolated from the spleen stained for CD93 and B220, (FIG. 11B) immature or mature gated B cells stained for IgM and CD23, or (FIG. 11C) immature or mature gated B cells stained for CD21/35 and IgM from a representative control VI3 mouse and a representative homozygous hV$_H$IgG1ΔC$_H$1ΔIgG2a/2bΔIgG3ΔIgD/A/E×Vκ1-39Jκ5 (6180 HO×1634 HO) mouse.
Figure 12:
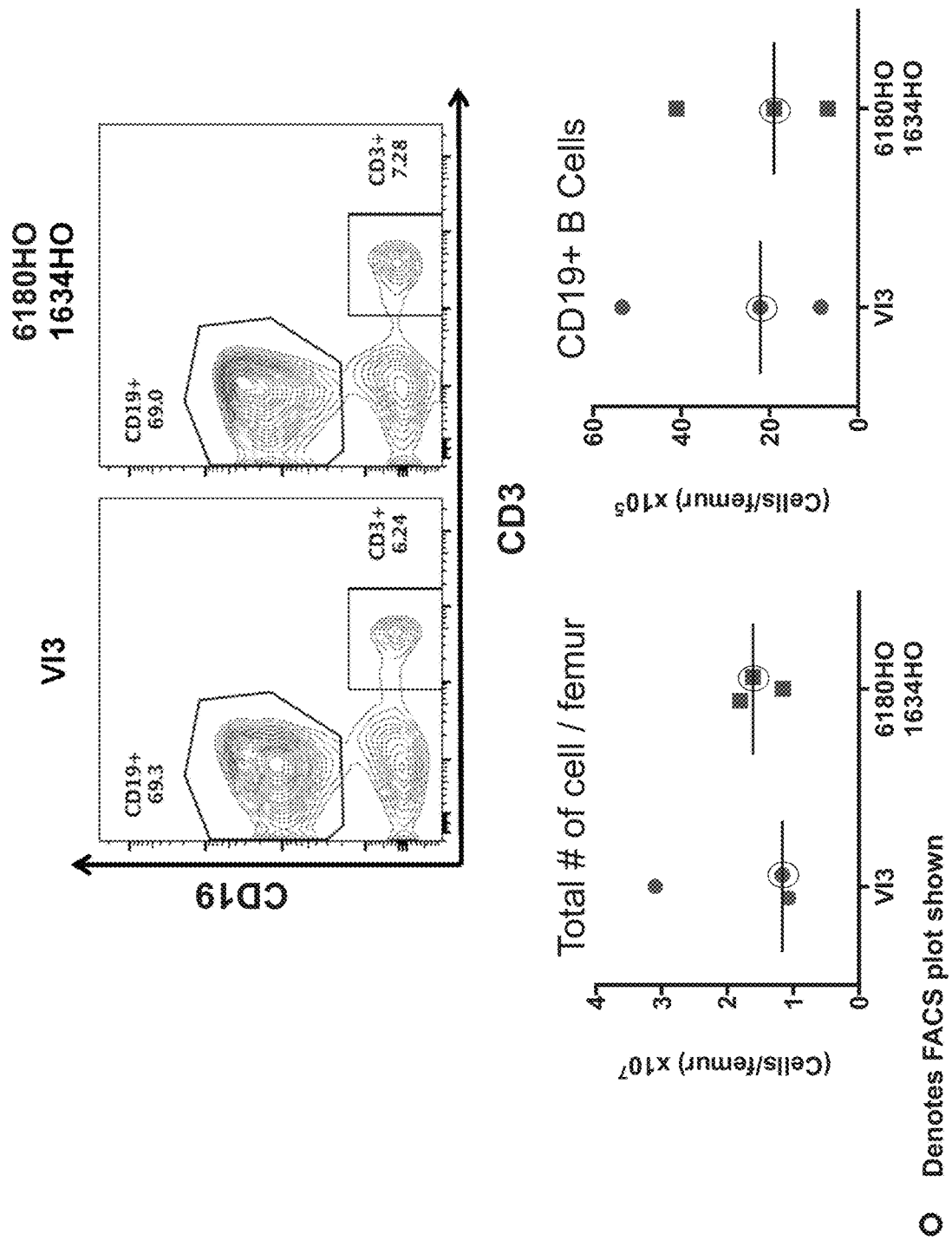
FIG. 12 shows contour plots of bone marrow isolated from the femurs of a representative control VI3 mouse and a representative homozygous hV$_H$IgG1ΔC$_H$1 & IgG2a/2bΔIgG3ΔIgD/A/E×Vκ1-39Jκ5 (6180 HO×1634 HO) mouse, stained with CD19 and CD3. Also shown are the total number of cells or CD19$^+$ B cells per femur (y-axis; Cells/femur×10$^7$) of three representative mice from each group. The animal for which the contour plots are included is encircled.
Figure 13:
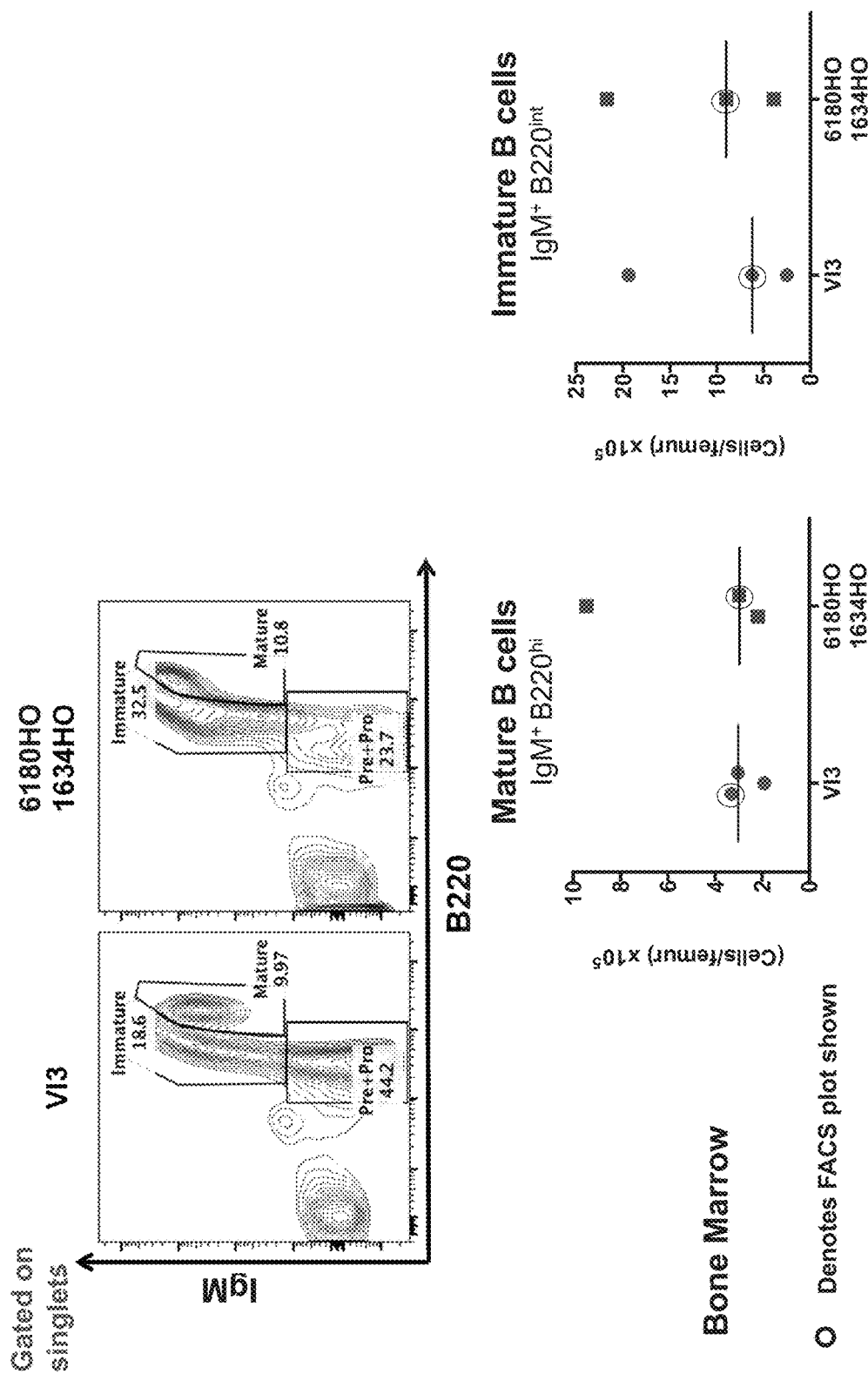
FIG. 13 shows contour plots of bone marrow isolated from femurs of a representative control VI3 mouse and a representative homozygous hV$_H$IgG1ΔC$_H$1ΔIgG2a/2bΔIgG3ΔIgD/A/E×Vκ1-39Jκ5 (6180 HO×1634 HO) mouse stained with IgM and B220. Also shown is the total number of mature (IgM$^+$ B220$^{hi}$) and immature (IgM$^+$ B220$^{int}$) B cells per femur (y-axis; Cells/femur×10$^7$) of three representative mice from each group. The animal for which the contour plots are included is encircled.

Following staining, cells were washed and fixed in 2% formaldehyde. Data acquisition was performed on a LSRII flow cytometer and analyzed with FLOWJO™ software (Tree Star, Inc.). FIG. 9 shows that these mice have normal serum steady state IgM and IgG levels. FIGS. 10 and 11 show the results for the splenic compartment, demonstrating nearly normal B cell numbers and nearly normal B cell maturation in the spleen. FIGS. 12 and 13 show the results for the bone marrow compartment, demonstrating normal B cell numbers and nearly normal B cell development in the bone marrow.

Example 2

Mice Encoding a $V_L$ Single Domain Binding Protein: Mice Comprising an Immunoglobulin Chain Having a Light Chain Variable Region and a Heavy Chain Constant Region Lacking a Functional $C_H1$ Domain

Example 2.1

Generation of Animals

A mouse having light chain gene segments introduced into a heavy chain locus was generated as described in U.S. Patent Publication No. 2012/0096572. Specifically, various targeting constructs were made using VELOCIGENE® genetic engineering technology to modify mouse genomic Bacterial Artificial Chromosome (BAC) libraries (see, e.g., U.S. Pat. No. 6,586,251 and Valenzuela, D. M., Murphy, A. J., Frendewey, D., Gale, N. W., Economides, A. N., Auerbach, W., Poueymirou, W. T., Adams, N. C., Rojas, J., Yasenchak, J., Chernomorsky, R., Boucher, M., Elsasser, A. L., Esau, L., Zheng, J., Griffiths, J. A., Wang, X., Su, H., Xue, Y., Dominguez, M. G., Noguera, I., Torres, R., Macdonald, L. E., Stewart, A. F., DeChiara, T. M., Yancopoulos, G. D. (2003). High-throughput engineering of the mouse genome coupled with high-resolution expression analysis. Nat Biotechnol 21, 652-659). Mouse BAC DNA was modified by homologous recombination to inactivate the endogenous mouse heavy chain locus through targeted deletion of $V_H$, $D_H$ and $J_H$ gene segments for the ensuing insertion of unrearranged human germline κ light chain gene sequences (top of FIG. 15).

Briefly, the mouse heavy chain locus was deleted in two successive targeting events using recombinase-mediated recombination. The first targeting event included a targeting at the 5' end of the mouse heavy chain locus using a targeting vector comprising from 5' to 3' a 5' mouse homology arm, a recombinase recognition site, a neomycin cassette and a 3' homology arm. The 5' and 3' homology arms contained sequence 5' of the mouse heavy chain locus. The second targeting event included a targeting at the 3' end of the mouse heavy chain locus in the region of the $J_H$ gene segments using a second targeting vector that contained from 5' to 3' a 5' mouse homology arm, a 5' recombinase recognition site, a second recombinase recognition site, a hygromycin cassette, a third recombinase recognition site, and a 3' mouse homology arm. The 5' and 3' homology arms contained sequence flanking the mouse $J_H$ gene segments and 5' of the intronic enhancer and constant regions. Positive ES cells containing a modified heavy chain locus targeted with both targeting vectors (as described above) were confirmed by karyotyping. DNA was then isolated from the double-targeted ES cells and subjected to treatment with a recombinase thereby mediating the deletion of genomic DNA of the mouse heavy chain locus between the 5' recombinase recognition site in the first targeting vector and the 5' recombinase recognition site in the second targeting vector, leaving a single recombinase recognition site and the hygromycin cassette flanked by two recombinase recognition sites (see top of FIG. 15). Thus a modified mouse heavy chain locus containing intact $C_H$ genes was created for progressively inserting human κ germline gene segments in a precise manner using targeting vectors as outlined in FIG. 15.

Figure 14B:
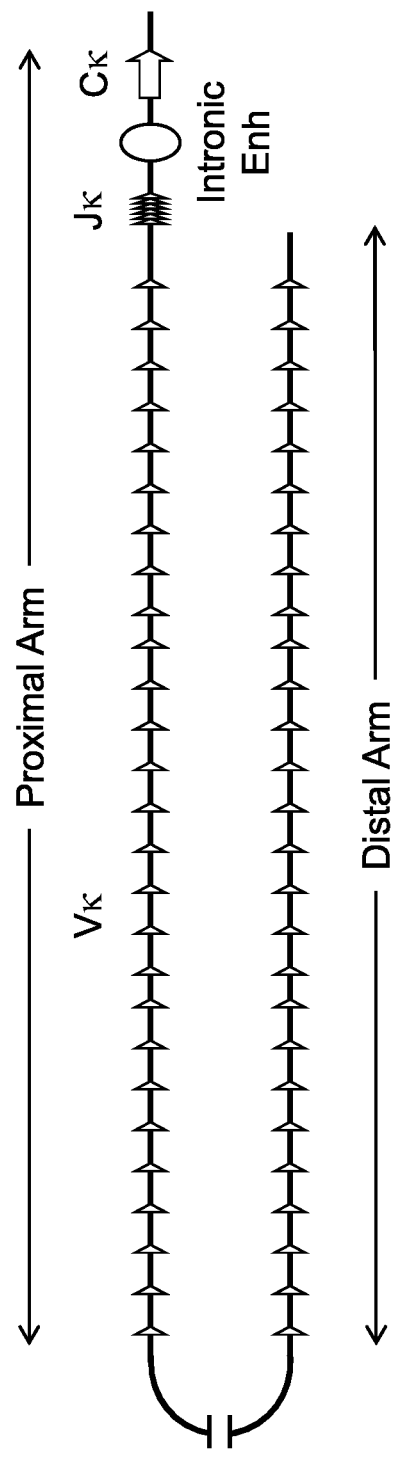
FIG. 14B illustrates a schematic of the human κ light chain locus (not to scale). The human κ light chain locus is duplicated into distal and proximal contigs of opposite polarity spanning about 440 kb and 600 kb, respectively. Between the two contigs is about 800 kb of DNA that is believed to be free of Vκ gene segments. The human κ light chain locus contains about 76 Vκ gene segments, 5 Jκ gene segments, an intronic enhancer (Enh) and a single constant region (Cκ).

Four separate targeting vectors were engineered to progressively insert 40 human Vκ gene segments and five human Jκ gene segments into the inactivated mouse heavy chain locus (described above) (FIG. 15). The human κ gene segments used for engineering the four targeting constructs are naturally found in proximal contig of the germline human κ light chain locus (FIG. 14B).

Mice heterozygous for such modified heavy chain loci were bred to obtain a mouse homozygous for the heavy chain locus as described above. Embryonic stem cells comprising such modified heavy chain loci comprising light chain variable region gene segments were targeted according to the scheme provided in FIG. 16 and using the methods described in U.S. Patent Publication No. US2011/0145937, Macdonald et al., which is incorporated herein by reference, to produce mice homozygous for a heavy chain locus comprising a light chain variable region and a heavy chain constant region that lacks a functional $C_H1$ domain in the IgG1 gene, and further lacks the IgG2b and IgG2a genes.

Figure 16:
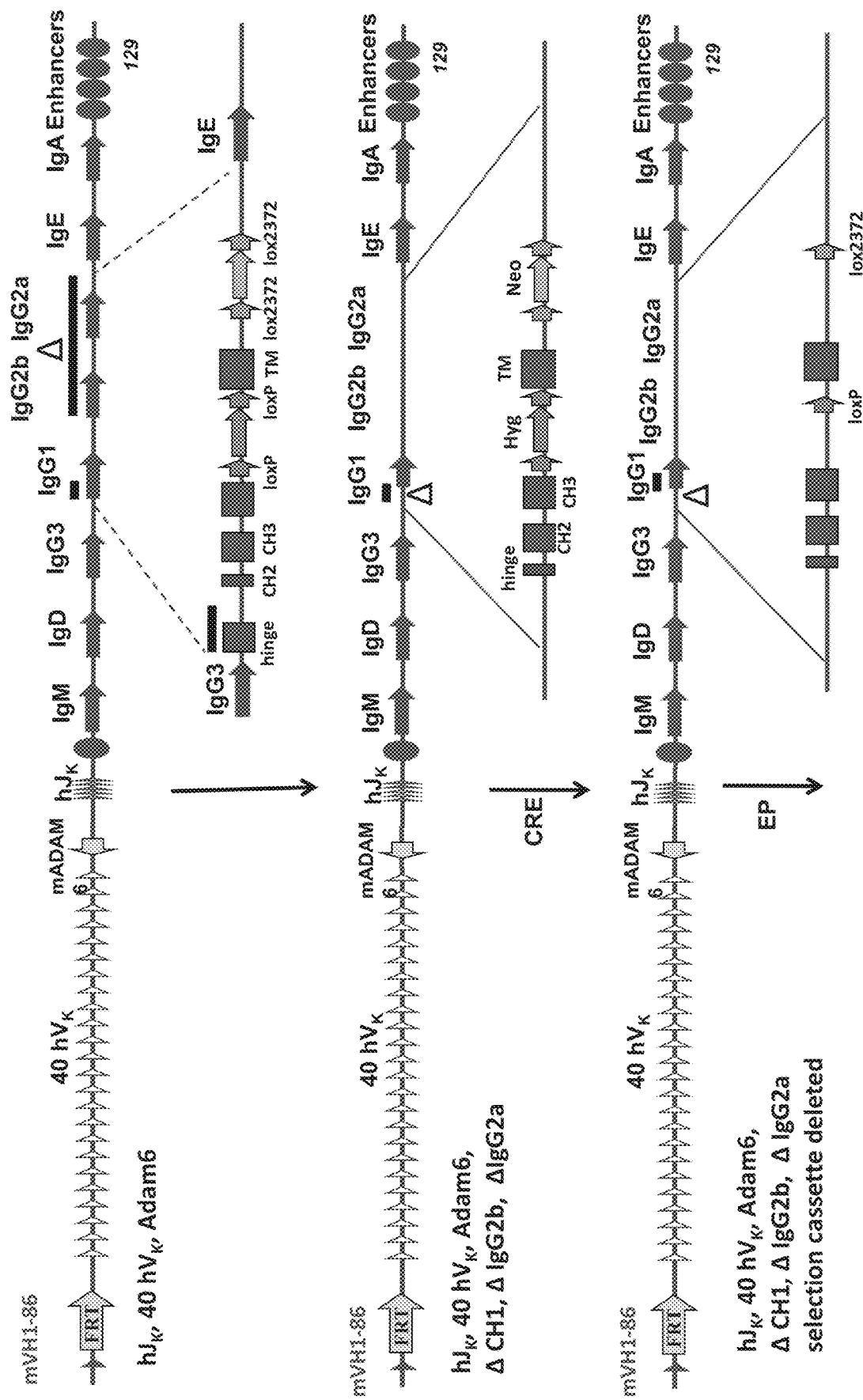
FIG. 16 shows the modified mouse heavy chain locus of FIG. 15 (hJκ, 40hVκ, Adam6; top); a targeting strategy that results in the deletion and/or inactivation of the C$_H$1 domain of the IgG1 gene sequence, the IgG2b gene sequence, and the IgG2a gene sequence from the modified mouse heavy chain locus of FIG. 15 (hJκ, 40hVκ, Adam6, ΔC$_H$1, ΔIgG2b, ΔIgG2a; middle), and a targeting strategy that results in the deletion of the selection cassette from a modified mouse heavy chain locus comprising unrearranged human Jκ gene segments and 40 human Vκ gene segments, wherein the modified mouse heavy chain locus lacks a functional C$_H$1 domain in the IgG1 gene and also lacks functional IgG2b and IgG2a genes (hJκ, 40hVκ, Adam6, ΔC$_H$1, ΔIgG2b, ΔIgG2a selection cassette deleted; also termed 6082, bottom). Human variable gene segments are indicated by empty triangles.

Thus, the germline of the modified heavy chain loci mice comprising light chain variable region gene segments described, e.g., in US 2012/0096572, were further modified using targeting vectors as described in FIG. 16 to engineer the heavy chain locus such that the IgG1 gene segment lacks a functional $C_H1$ domain and the IgG2a and IgG2b genes are deleted to obtain mice homozygous for a single domain antigen binding protein comprising a human kappa variable domain and a murine IgG1 constant region, wherein the IgG1 constant domain lacks a functional $C_H1$ region (hVκIgG1ΔC$_H$1ΔIgG2a ΔIgG2b; 6082 HO). Additional variations of combinations of CH1 deletions and/or immunoglobulin constant gene deletions are made, e.g., a mouse is made that comprises a heavy chain locus comprising a human light chain kappa variable region wherein both IgG1 and IgG2a comprise CH1 domain deletions, and the mouse also comprises a deletion of IgD, IgE, IgG3, and IgG2b.

Western blotting has confirmed that light chain only single domain binding proteins are present and may be isolated from mice genetically modified to comprise a human kappa variable domain and a murine IgG1 constant region, wherein the IgG1 constant domain lacks a functional $C_H1$ region (6082 HO, data not shown).

Example 2.2

Confirmation of Productive Rearrangement of Gene Sequences Encoding VL Single Domain Binding Proteins The mRNA of B cells was isolated from the spleen and bone marrow of (a) mice homozygous for a heavy chain locus comprising a light chain variable region and a heavy chain constant gene sequence that lacks a functional $C_H1$ domain in the IgG1 gene, and further lacks the IgG2b and IgG2a genes, (b) control wild type and (c) control $C_H1$ delxULC mice homozygous for both a modified mouse heavy chain locus that expresses human heavy chain V, D and J segments, lacks a functional $C_H1$ domain in the IgG1 genes, and also lacks functional IgG2b and IgG2a genes, and comprises a single rearranged light chain locus also referred to as a common or universal light chain, see, e.g., U.S. Patent Publication No. 2011/0195454. The isolated mRNA was analyzed for productive rearrangement using the following probes and primers in a TAQMAN assay:

hJk/mIgG1 Hinge-Set 71 (Ordered from Biosearch Technologies)

(sense)  
(SEQ ID NO: 1)  
5'-GGACCAAGCTGGAGATCAAAC-3', (anti-sense)  
(SEQ ID NO: 2)  
5'-CTTCTGGGACTGTACATATGCAA-3', (probe)  
(SEQ ID NO: 3)  
5'-FAM-CCCAGGGATTGTGGTTGTAAGCC-BHQ1-3';

hJH/mIgG1 Hinge-Set 72 (Ordered from Applied Biosystems)

(sense)  
(SEQ ID NO: 4)  
5'-TGGTCACCGTCTCCTCAGTG-3', (anti-sense)  
(SEQ ID NO: 5)  
5'-CACACGTGACCTTAGGAGTCAGAG-3', (probe)  
(SEQ ID NO: 6)  
5'-FAM-TGGTTGTAAGCCTTGC-MGB-3';

mHPRT1-Set 51 (Ordered from Biosearch Technologies)

Figure 17A:
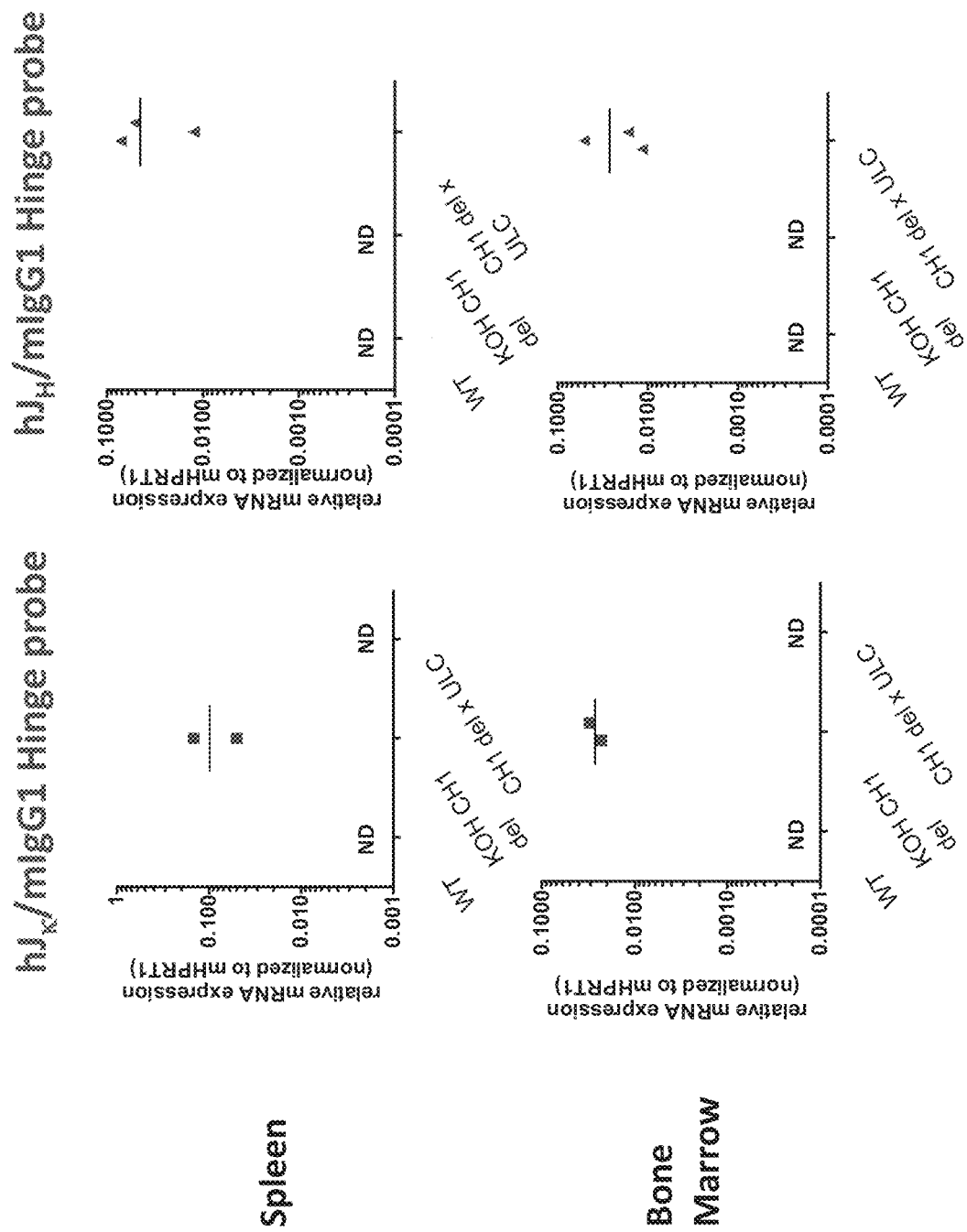
FIG. 17A shows the relative mRNA expression (normalized to HPRT1 mRNA; y-axis) by B cells isolated from the spleen and bone marrow of three different groups of animals (x-axis): wild type (WT) mice, mice homozygous for the modified heavy chain locus of FIG. 16 (hJκ, 40hVκ, Adam6, Δ C$_H$1 ΔIgG2b ΔIgG2a selection cassette deleted; KoH C$_H$1 del), and mice homozygous for both a modified mouse heavy chain locus that expresses human heavy chain V, D and J segments, lacks a functional C$_H$1 domain in the IgG1 genes, and also lacks functional IgG2b and IgG2a genes and comprises a single rearranged light chain locus (C$_H$1 del× ULC). Probes were designed to detect productive rearrangement, and consisted of a probe that detected recombination between a human Jκ segment and murine IgG1 hinge (hJk/mIgG1 hinge probe; left panels) or a probe that detected recombination between a human J$_H$ segment and murine IgG1 hinge (hJ$_H$/mIgG1 hinge probe; right panels). ND: not detected (Ct≥35). n=2 for WT, 2 for KoH C$_H$1 del, and 3 for C$_H$1 del×ULC.
Figure 17B:
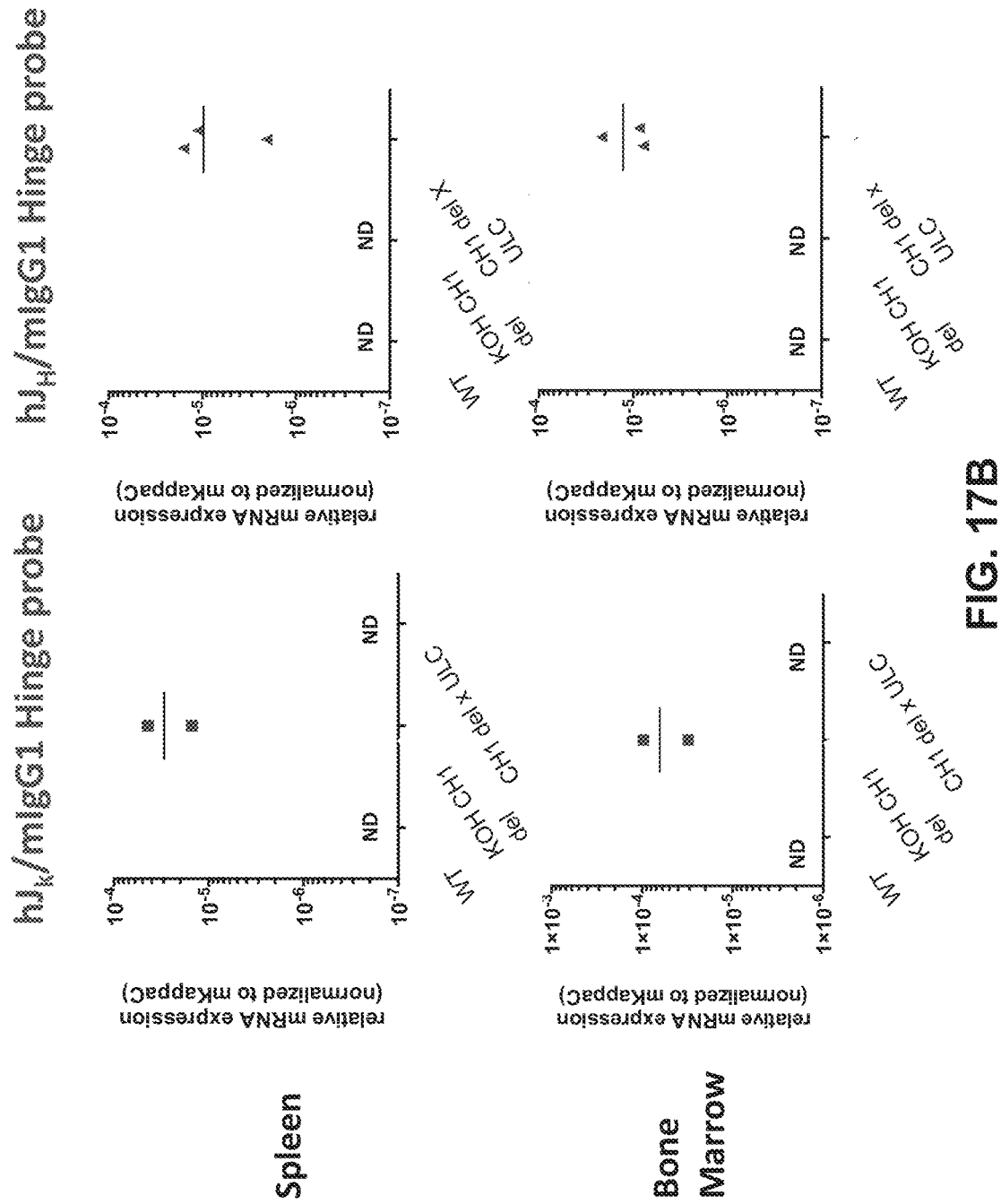
FIG. 17B shows the relative mRNA expression (normalized to mKappaC mRNA; y-axis) by B cells isolated from the spleen and bone marrow of three different groups of animals (x-axis): wild type (WT) mice, mice homozygous for the modified heavy chain locus of FIG. 16 (hJκ, 40hVκ, Adam6, Δ C$_H$1 ΔIgG2b ΔIgG2a selection cassette deleted; KoH C$_H$1 del), and mice homozygous for both a modified mouse heavy chain locus that expresses human heavy chain V, D and J segments, lacks a functional C$_H$1 domain in the IgG1 gene sequence, and also lacks functional IgG2b and IgG2a gene sequences and comprises a single rearranged light chain locus ($C_H1$ del×ULC). Probes were designed to detect productive rearrangement, and consisted of a probe that detected recombination between a human vκ segment and murine IgG1 hinge (hJκ/mIgG1 Hinge probe; left panels) or a probe that detected human $J_H$ segment and murine IgG1 hinge (hJ$_H$/m IgG1 hinge probe; right panels). ND: not detected (Ct≥35). n=2 for WT, 2 for KoH $C_H1$ del, and 3 for $C_H1$ del×ULC.

(sense)  
(SEQ ID NO: 7)  
5'-CGAGTCTGAAGCTCTCGATTTCCT-3', (anti-sense)  
(SEQ ID NO: 8)  
5'-CAGCCAACACTGCTGAAACATG-3', (probe)  
(SEQ ID NO: 9)  
5'-FAM-CAGCATCTAAGAGGTTTTGCTCAGTGGA-BHQ-3';

As shown in FIGS. 17A and 17B, unrearranged light chain variable region gene segments that replace endogenous heavy chain variable region gene segments are capable of undergoing productive rearrangement with the endogenous heavy chain constant IgG1 gene lacking a functional $C_H1$ domain.

Example 3

Mice Encoding a VL Single Domain Binding Protein: Mice Comprising an Immunoglobulin Chain Having a Light Chain Variable Region and a Heavy Chain Constant Region Lacking a Functional $C_H1$ Domain, and Comprising a Single Rearranged Light Chain (ULC)

Figure 18:
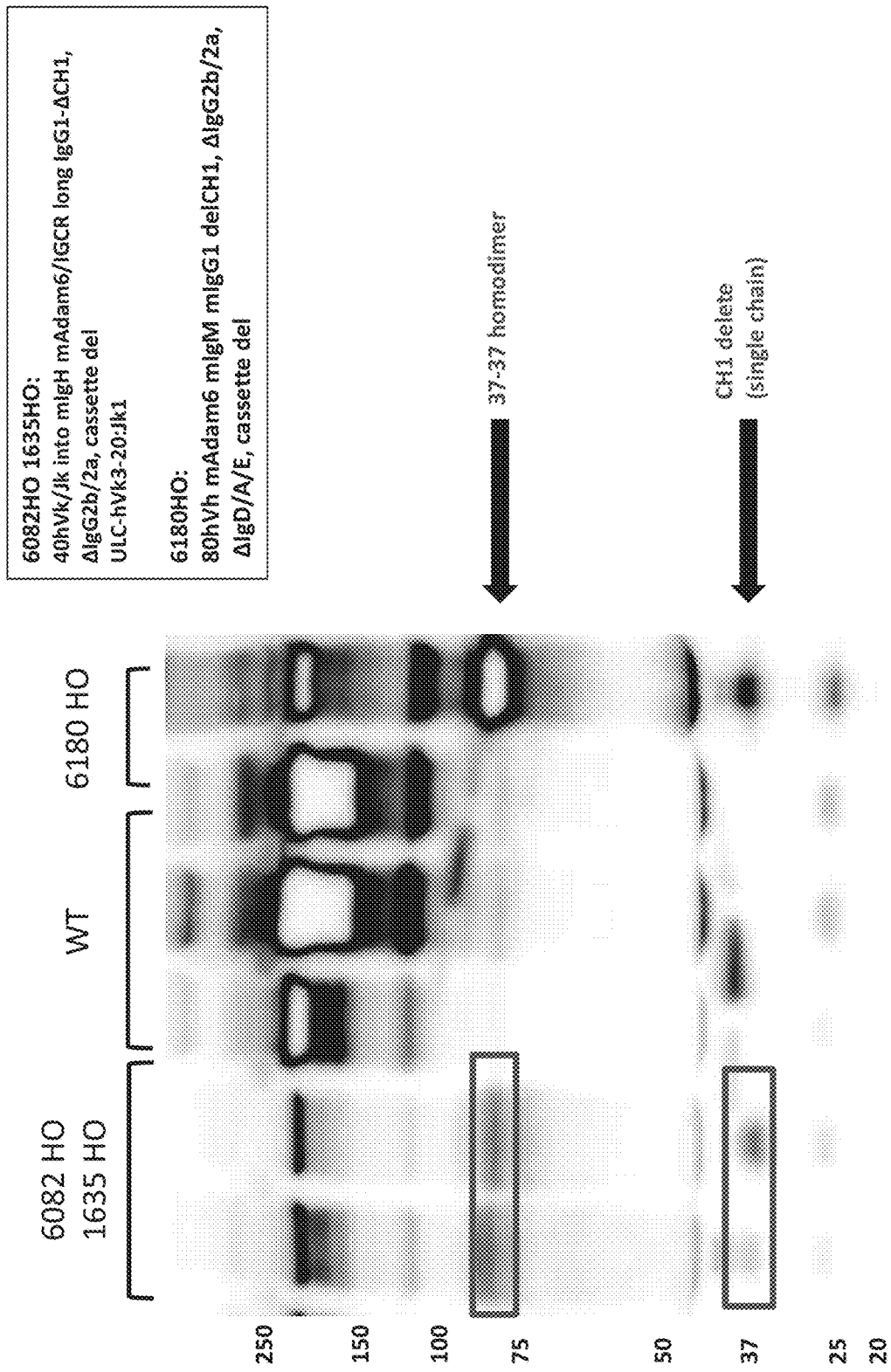
FIG. 18 provides an image of a Western blot, prepared under non-reducing conditions and visualized with antimouse IgG, of mouse sera from three hVκIgG1Δ$C_H1$ ΔIgG2a/2b×Vκ3-20Jκ1 ULC homozygous mice (6082HO 1635 HO), three VELOCIMMUNE® mice (VI3 IgG1) having human variable region ($V_H$ and Vκ) with mouse constant regions (WT), and two hV$_H$IgG1Δ$C_H1$ΔIgG2a/2bΔIgG3ΔIgD/A/E mice (6180 HO) demonstrating presence or absence of dimeric single domain antigen binding proteins (37-37 homodimer) or monomeric Δ$C_H1$ single domain binding proteins ($C_H1$ delete single chain).

VELOCIMMUNE® humanized mice containing a single rearranged human germline light chain region (ULC Vκ3-20Jκ1; 1635, alternatively ULC Vκ1-39Jκ5; 1633 is also used) were bred to mice carrying a modified heavy chain locus comprising a human light chain kappa variable region operably linked to a murine constant region wherein the IgG1 $C_H1$ domain, and the IgG2a and IgG2b genes, were deleted or inactivated (hVκIgG1Δ$C_H$1ΔIgG2a/2b; 6082) to obtain the following progeny mice: hVκIgG1Δ$C_H$1 ΔIgG2a/2b×Vκ3-20Jκ1 ULC homozygous mice (6082HO 1635 HO). These mice expressed $V_L$ single domain binding proteins (FIG. 18).

We claim:

1. A genetically modified mouse whose germline has a genome comprising a replacement of:
   (i) a plurality of unrearranged endogenous variable heavy chain ($V_H$) gene segments,
   (ii) all unrearranged endogenous diversity heavy chain ($D_H$) gene segments, and
   (iii) all unrearranged endogenous joining heavy chain ($J_H$) gene segments, with:
   (a) a plurality of unrearranged human light chain variable kappa (Vκ) gene segments, and
   (b) all unrearranged human light chain joining kappa (Jκ) gene segments, such that the unrearranged human light chain Vκ and Jκ gene segments are operably linked to a modified endogenous heavy chain constant region that lacks an IgG2 gene, comprises endogenous full-length IgM, IgD, IgA, and IgE genes, and comprises an endogenous IgG1 gene that comprises a deleted or inactivated nucleotide sequence encoding its $C_H1$ domain,
   wherein the unrearranged human light chain Vκ and Jκ gene segments rearrange in a B cell such that the mouse functionally expresses:
   a hybrid IgM antibody comprising a human κ light chain variable domain operably linked to an endogenous full-length IgM; and
   a hybrid IgG1 antibody comprising a human κ light chain variable domain operably linked to an endogenous IgG1 with a deleted or inactivated CH1 domain.

2. The genetically modified mouse of claim 1, wherein the hybrid IgG1 antibody has an inactivated hinge region.

3. The genetically modified mouse of claim 1, wherein the genome comprises a nucleic acid sequence encoding an Adam6a and/or an Adam6b gene.

* * * * *

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: sense probe

<400> SEQUENCE: 1
ggaccaagct ggagatcaaa c                                        21

<210> SEQ ID NO 2
<211> LENGTH: 23
<212> TYPE: DNA
<213> ORGANISM: Artificial Sequence
<220> FEATURE:
<223> OTHER INFORMATION: anti-sense probe

<400> SEQUENCE: 2
cttctgggac tgtacatatg caa                                      23

<210> SEQ ID NO 3
<211> LENGTH: 23
<212> TYPE: DNA
<213> ORGANISM: Artificial Sequence
<220> FEATURE:
<223> OTHER INFORMATION: probe

<400> SEQUENCE: 3
```

```
cccagggatt gtggttgtaa gcc                                              23
```

<210> SEQ ID NO 4
<211> LENGTH: 20
<212> TYPE: DNA
<213> ORGANISM: Artificial Sequence
<220> FEATURE:
<223> OTHER INFORMATION: sense probe

<400> SEQUENCE: 4

```
tggtcaccgt ctcctcagtg                                                  20
```

<210> SEQ ID NO 5
<211> LENGTH: 24
<212> TYPE: DNA
<213> ORGANISM: Artificial Sequence
<220> FEATURE:
<223> OTHER INFORMATION: anti-sense probe

<400> SEQUENCE: 5

```
cacacgtgac cttaggagtc agag                                             24
```

<210> SEQ ID NO 6
<211> LENGTH: 16
<212> TYPE: DNA
<213> ORGANISM: Artificial Sequence
<220> FEATURE:
<223> OTHER INFORMATION: probe

<400> SEQUENCE: 6

```
tggttgtaag ccttgc                                                      16
```

<210> SEQ ID NO 7
<211> LENGTH: 24
<212> TYPE: DNA
<213> ORGANISM: Artificial Sequence
<220> FEATURE:
<223> OTHER INFORMATION: sense probe

<400> SEQUENCE: 7

```
cgagtctgaa gctctcgatt tcct                                             24
```

<210> SEQ ID NO 8
<211> LENGTH: 22
<212> TYPE: DNA
<213> ORGANISM: Artificial Sequence
<220> FEATURE:
<223> OTHER INFORMATION: sense probe

<400> SEQUENCE: 8

```
cagccaacac tgctgaaaca tg                                               22
```

<210> SEQ ID NO 9
<211> LENGTH: 28
<212> TYPE: DNA
<213> ORGANISM: Artificial Sequence
<220> FEATURE:
<223> OTHER INFORMATION: Probe

<400> SEQUENCE: 9

```
cagcatctaa gaggttttgc tcagtgga                                         28
```